(12) United States Patent
Bae et al.

(10) Patent No.: US 10,236,451 B2
(45) Date of Patent: Mar. 19, 2019

(54) COMPOUND AND ORGANIC ELECTROLUMINESCENT DEVICE COMPRISING THE SAME

(71) Applicant: DOOSAN CORPORATION, Seoul (KR)

(72) Inventors: Hyung Chan Bae, Yongin-si (KR); Young Mi Beak, Yongin-si (KR); Tae Hyung Kim, Yongin-si (KR); Ho Cheol Park, Suwon-si (KR); Chang Jun Lee, Ansan-si (KR); Jin Young Shin, Yongin-si (KR)

(73) Assignee: DOOSAN CORPORATION, Seoul (KR)

( * ) Notice: Subject to any disclaimer, the term of this patent is extended or adjusted under 35 U.S.C. 154(b) by 639 days.

(21) Appl. No.: 14/413,575

(22) PCT Filed: Mar. 6, 2013

(86) PCT No.: PCT/KR2013/001819
§ 371 (c)(1),
(2) Date: Jan. 8, 2015

(87) PCT Pub. No.: WO2014/010810
PCT Pub. Date: Jan. 16, 2014

(65) Prior Publication Data
US 2015/0171344 A1  Jun. 18, 2015

(30) Foreign Application Priority Data

Jul. 9, 2012  (KR) .................. 10-2012-0074723

(51) Int. Cl.
*H01L 51/54* (2006.01)
*C09K 11/06* (2006.01)
*H01L 51/00* (2006.01)
*C07D 487/04* (2006.01)
*C07D 235/06* (2006.01)
*C07D 235/18* (2006.01)
*C07D 249/18* (2006.01)
*C07D 261/20* (2006.01)
*C07D 498/04* (2006.01)
*C07D 277/64* (2006.01)
*C07D 277/66* (2006.01)
*C07D 513/04* (2006.01)
*H01L 51/50* (2006.01)

(52) U.S. Cl.
CPC ........ *H01L 51/0072* (2013.01); *C07D 235/06* (2013.01); *C07D 235/18* (2013.01); *C07D 249/18* (2013.01); *C07D 261/20* (2013.01); *C07D 277/64* (2013.01); *C07D 277/66* (2013.01); *C07D 487/04* (2013.01); *C07D 498/04* (2013.01); *C07D 513/04* (2013.01); *C09K 11/06* (2013.01); *H01L 51/0067* (2013.01); *H01L 51/0071* (2013.01); *C09K 2211/1007* (2013.01); *C09K 2211/1029* (2013.01); *C09K 2211/1033* (2013.01); *C09K 2211/1037* (2013.01); *C09K 2211/1044* (2013.01); *C09K 2211/1048* (2013.01); *C09K 2211/1051* (2013.01); *C09K 2211/1059* (2013.01); *C09K 2211/1074* (2013.01); *H01L 51/0085* (2013.01); *H01L 51/5012* (2013.01); *H01L 51/5016* (2013.01); *H01L 51/5056* (2013.01); *H01L 51/5088* (2013.01)

(58) Field of Classification Search
CPC .. C07D 235/00; C07D 235/06; C07D 235/18; C07D 249/00; C07D 249/16; C07D 249/18; C07D 261/00; C07D 261/20; C07D 277/00; C07D 277/60; C07D 277/64; C07D 277/66; C07D 487/00; C07D 487/02; C07D 487/04; C07D 498/00; C07D 498/02; C07D 498/04; C07D 513/00; C07D 513/02; C07D 513/04; C09K 11/06; C09K 2211/00; C09K 2211/10; C09K 2211/1007; C09K 2211/1033; C09K 2211/1029; C09K 2211/1037; C09K 2211/1044; C09K 2211/1048; C09K 2211/1051; C09K 2211/1059; C09K 2211/1074; H01L 51/0032; H01L 51/005; H01L 51/0067; H01L 51/0071; H01L 51/0072; H01L 51/0073; H01L 51/0074; H01L 51/0085; H01L 51/50; H01L 51/5012; H01L 51/5016; H01L 51/5056; H01L 51/5088
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

FOREIGN PATENT DOCUMENTS

CN  102146077 A  8/2011
DE  676196 C  5/1939
(Continued)

OTHER PUBLICATIONS

Farcasan et al. Journal für Praktische Chemie 1970, 312, 1007-1010. Year of publication: 1970.*
(Continued)

*Primary Examiner* — Andrew K Bohaty
(74) *Attorney, Agent, or Firm* — Sughrue Mion, PLLC

(57) ABSTRACT

Disclosed is a novel benzimidazole compound having excellent hole injection and transport capabilities, light-emitting capabilities, and the like, and an organic electroluminescent device which comprises the benzimidazole compound in one or more organic material layers thereof so as to thereby achieve enhanced characteristics, such as light-emitting efficiency, driving voltage, and lifespan.

10 Claims, No Drawings

(56) References Cited

FOREIGN PATENT DOCUMENTS

| JP | 2000273331 A | * 10/2000 | ............ C09B 23/02 |
|---|---|---|---|
| JP | 2000273331 A | 10/2000 | |
| JP | 2001222086 A | 8/2001 | |
| JP | 2008526708 A | 7/2008 | |
| JP | 201064968 A | 3/2010 | |
| KR | 1020100131271 A | 12/2010 | |
| KR | 1020110002156 A | 1/2011 | |
| KR | 1020110117549 A | 10/2011 | |
| WO | 2011126225 A1 | 10/2011 | |

OTHER PUBLICATIONS

Maisuradze et al. J. Chem. Chem. Eng. 2012, 6, 378-382. (Year: 2012).*

Machine translation of JP2000-273331. (Year: 2000).*

Nakagawa et al. Organic Letters 2009, 11, 1475-1478. (Year: 2009).*

International Searching Authority, International Search Report dated Aug. 30, 2013, issued in corresponding International Application No. PCT/KR2013/001819.

Jian-Guang Guo et al., "New fluorene derivatives based on 3,9-dihydrofluoreno[3,2-d]imidazole (FI): Characterization and influence of substituents on photoluminescence", Journal of Photochemistry and Photobiology A: Chemistry, 2011, vol. 219, pp. 42-49 (8 pgs. total).

Mayavan Viji et al., "RuCl3/SnCl2 mediated synthesis of pyrrolo[2,3-c]carbazoles and consequent preparation of indolo[2,3-c]carbazoles", Tetrahedron, 2012, vol. 68, pp. 2453-2458.

Japan Patent Office, Communication dated Feb. 2, 2016, issued in corresponding Japanese Application No. 2015-521527.

Henry Gilman et al., "Dibenzorfuran. XIII. Orientation and Substituted Amines", Journal of the American Chemical Society, Oct. 1939, vol. 61, pp. 2836-2845 (11 pgs. total).

Eugene Sawicki, "Preparation and Absorption Spectra of 1,2- and 2,3-Disubstituted Dibenzothiophene Derivatives", Journal of Organic Chemistry, 1954, vol. 19, pp. 608-614 (8 pgs. total).

Yuji Oikawa et al., "A New Synthetic Method for Condensed Heterocycles, Carbazoles, Indoles, and Benzothiophenes, Based on Acid-Catalyzed Cyclization of β-Keto Sulfoxides", Journal of Organic Chemistry, 1976, vol. 41, No. 7, pp. 1118-1124 (8 pgs. total).

Hadjila Chabane et al., "Synthesis of novel 2-cyanothiazolocarbazoles analogues of ellipticine", Tetrahedron Letters, Feb. 2002, vol. 43, pp. 2483-2486 (5 pgs. total).

Takahiro Itoh et al., "A Novel Practical Synthesis of Benzothiazoles via Pd-Catalyzed Thiol Cross-Coupling", Organic Letters, Jul. 4, 2007, vol. 9, No. 18, pp. 3687-3689 (4 pgs. total).

* cited by examiner

COMPOUND AND ORGANIC ELECTROLUMINESCENT DEVICE COMPRISING THE SAME

CROSS REFERENCE TO RELATED APPLICATIONS

This application is a National Stage of International Application No. PCT/KR2013/001819 filed Mar. 6, 2013, claiming priority based on Korean Patent Application No. 10-2012-0074723 filed Jul. 9, 2012, the contents of all of which are incorporated herein by reference in their entirety.

TECHNICAL FIELD

The present invention relates to a novel compound and an organic electroluminescent device including the same, and more particularly, to a novel compound having excellent hole injection and transport capabilities, light-emitting capabilities, and the like, and an organic electroluminescent device which comprises the compound as a material for an organic material layer to improve characteristics, such as light-emitting efficiency, driving voltage, and lifespan.

BACKGROUND ART

Studies on an organic electroluminescent (EL) device (hereinafter, simply referred to as 'organic EL device') have continued from the start point of observing an organic thin film light emission by Bernanose in the 1950s to blue electroluminescence using an anthracene single crystal in 1965, and then an organic EL device having a laminated structure including functional layers of a hole layer and a light emitting layer was proposed by Tang in 1987. Since then, the organic EL device has been developed in a form in which a specific organic material layer is introduced into the device and a specific material used therein has been developed in order to enhance the efficiency and lifespan of an organic EL device.

When voltage is applied between two electrodes of the organic EL device, holes are injected into the organic material layer at the anode, and electrons are injected into the organic material layer at the cathode. When the injected holes and electrons meet each other, an exciton is formed, and then exciton falls down to a bottom state to emit light. Materials used as the organic material layer may be classified into a light-emitting material, a hole injection material, a hole transporting material, an electron transporting material, an electron injection material, and the like according to the function.

Light-emitting materials of the organic EL device may be divided into blue, green, and red light-emitting materials according to the light-emitting color. In addition, the light-emitting materials may be classified into yellow and orange light-emitting materials which are necessary for implementing a more natural color. Furthermore, a host/dopant system may be used as a light-emitting material for the purpose of enhancing color purity and light-emitting efficiency through energy transfer. Dopant materials may be divided into a fluorescent dopant using an organic material and a phosphorescent dopant using a metal complex compound including heavy atoms such as Ir and Pt. Since the development of the phosphorescent material may theoretically can enhance light-emitting efficiency by up to 4 times compared to the fluorescent material, interests in not only phosphorescent dopants, but also phosphorescent host materials have been focused.

As materials used as a hole injection layer, a hole transporting layer, a hole blocking layer, and an electron transporting layer, NPB, BCP, $Alq_3$ and the like represented by the following Formulae have been widely known until now, and for a light-emitting material, anthracene derivatives have been reported as a fluorescent dopant/host material In particular, for the phosphorescent material having a great advantage in terms of enhancing the efficiency among the light-emitting materials, there are metal complex compounds including Ir, such as Firpic, $Ir(ppy)_3$ and $(acac)Ir(btp)_2$, and these materials are used as blue, green and red dopant materials. Until now, CBP exhibits excellent characteristics as a phosphorescent host material.

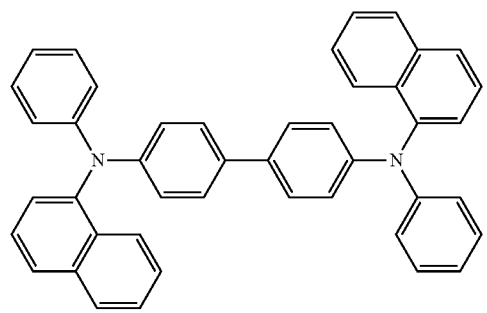

NPB

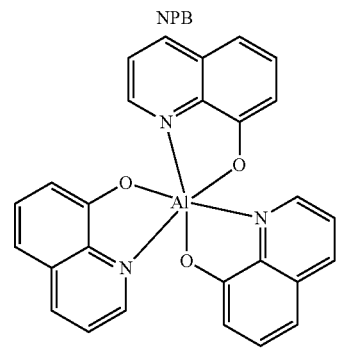

Alq3

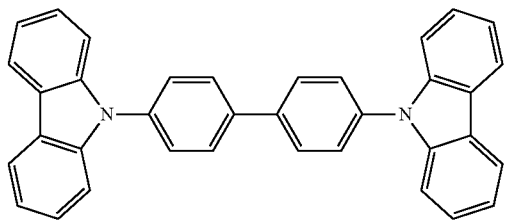

CBP

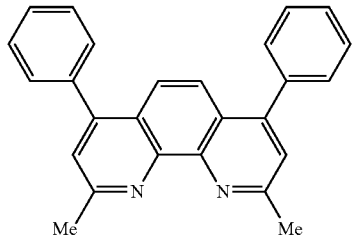

BCP

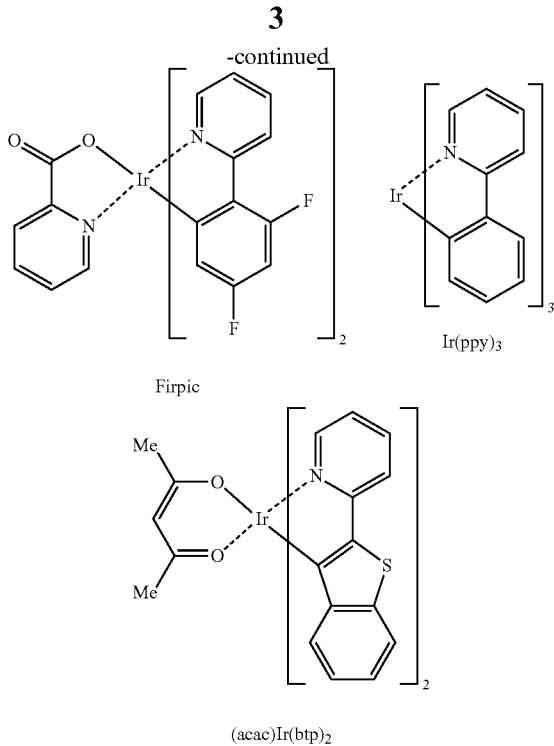

Firpic (acac)Ir(btp)₂

However, since the light-emitting materials according to the prior art are good in terms of light-emitting characteristics, but have a low glass transition temperature and thus are very poor in thermal stability, these materials fail to reach a level which is satisfactory in terms of lifespan for an organic EL device. Accordingly, there is a need for developing a light-emitting material having excellent performance.

INVENTION

Technical Problem

An object of the present invention is to provide a novel compound which has excellent hole injection capabilities, hole transport capabilities, light-emitting capabilities and the like, and thus may be used as a light-emitting layer material, a hole transporting layer material, and a hole injection layer material.

Further, another object of the present invention is to provide an organic electroluminescent device which includes the novel compound to have a low driving voltage, high light-emitting efficiency, and enhanced lifespan.

Technical Solution

In order to achieve the above-described objects, the present invention provides a compound represented by the following Formula 1.

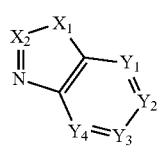

[Formula 1]

In Formula 1, $X_1$ is selected from the group consisting of $NR_1$, O, S, Se, $SiR_2R_3$, and $CR_4R_5$;

$X_2$ is N or $CR_6$;

$Y_1$ to $Y_4$ are each independently N or $CR_7$, and in this case, a plurality of $CR_7$'s is the same as or different from each other, provided that at least one of $Y_1$ to $Y_4$ is $CR_7$, and is fused with an adjacent group to form a fused ring represented by the following Formula 2;

$R_1$ to $R_7$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_1$ to $R_7$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group;

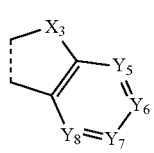

[Formula 2]

In Formula 2, a dotted line means a site where fusion with the compound of Formula 1 occurs;

$X_3$ is selected from the group consisting of O, S, Se, $N(Ar_1)$, $C(Ar_2)(Ar_3)$, and $Si(Ar_4)(Ar_5)$;

$Ar_1$ to $Ar_5$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group and a substituted or unsubstituted $C_6$ to $C_{60}$ arylamine group, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group;

$Y_5$ to $Y_8$ are each independently N or $CR_8$, and in this case, a plurality of $CR_8$'s is the same as or different from each other;

$R_8$ is selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_8$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

Further, the present invention provides an organic EL device including an anode, a cathode, and one or more organic material layers interposed between the anode and the cathode, in which at least one of the one or more organic material layers includes the above-described compound.

The one or more organic material layers including the compound are selected from the group consisting of a hole transporting layer, a hole injection layer, and a light-emitting layer, and is preferably a light-emitting layer. In particular, when the compound is included in the light-emitting layer, the compound is used as a phosphorescent host material.

Advantageous Effects

The compound according to the present invention has excellent heat resistance, hole injection capabilities, hole transport capabilities, light-emitting capabilities and the like, and thus may be used as an organic material layer material, preferably, a hole injection layer material, a hole transporting layer material, or a light-emitting layer material for an organic electroluminescent device.

In addition, an organic electroluminescent device including the compound according to the present invention in a hole injection layer, a hole transporting layer, and/or a light-emitting layer may be greatly enhanced in terms of light-emitting performance, driving voltage, lifespan, efficiency, and the like, and furthermore, may be effectively applied to a full-color display panel, and the like.

BEST MODE

Hereinafter, the present invention will be described.

A novel compound according to the present invention is a compound in which an indole-based moiety and the like are fused with an indole-based moiety, an indazole-based moiety, or a benzimidazole-based moiety, and the like to form a basic structure, and various substituents are bonded to the basic structure, and is represented by Formula 1. The compound represented by Formula 1 has a larger molecular weight than that of a material for an organic EL device [for example: 4,4-dicarbazolybiphenyl (hereinafter, represented by CBP)] according to the prior art, and thus has not only high thermal stability, but also excellent hole injection capabilities, hole transport capabilities, light-emitting capabilities, and the like. Accordingly, when the compound of Formula 1 is included in an organic electroluminescent device, driving voltage, efficiency, and the like of the device may be enhanced.

In the organic electroluminescent device, the compound represented by Formula 1 needs to have an energy level larger than that of a dopant molecule in order to have high light-emitting efficiency, and in the compound represented by Formula 1, various substituents such as an alkyl group, an aryl group, and a heteroallyl group are bonded to a basic structure in which an indole moiety, an indazole moiety or a benzimidazole moiety is fused with an indole moiety and the like, and an aromatic ring or a heteroaromatic ring, preferably a heteroaromatic ring is also fused with the basic structure, and thus, the compound may control the energy level to have a wide band-gap (sky blue to red). Accordingly, the compound of Formula 1 may minimize energy loss during the light-emitting process, thereby exhibiting an effect of improving light-emitting efficiency. Furthermore, these characteristics of the compound may improve hole injection and transport capabilities, light-emitting efficiency, driving voltage, lifespan characteristics, and the like as well as phosphorescent characteristics of the device. Further, the compound of Formula 1 may be applied to the hole transporting layer, the electron transporting layer, and the like as well as the light-emitting layer according to the type of substituent to be introduced into the basic structure. In particular, due to the indole moiety, the compound of Formula 1 may exhibit excellent characteristics as a light-emitting host compared to the CBP according to the prior art.

In addition, various substituents, particularly, an aryl group and/or a heteroaryl group are introduced into the basic structure, in which an indole moiety, an indazole moiety or a benzimidazole moiety is fused with an indole moiety and the like, to significantly increase the molecular weight of the compound, so that the glass transition temperature is enhanced, and accordingly, the compound represented by Formula 1 may have higher thermal stability than that of the CBP in the related art. Therefore, an organic electroluminescent device including the compound represented by Formula 1 of the present invention may greatly enhance durability and lifespan characteristics.

Furthermore, when the compound represented by Formula 1 is adopted as a material for a hole injection/transporting layer and a blue, green, and/or red phosphorescent host of an organic electroluminescent device, remarkably excellent effects may be exhibited in terms of efficiency and lifespan compared to the CBP in the related art. Therefore, the compound according to the present invention may greatly contribute to the improvement of performance and the enhancement of lifespan of the organic electroluminescent device, and furthermore, the enhancement of lifespan of the organic electroluminescent device may maximize performance of a full-color organic light-emitting panel.

In the compound represented by Formula 1 according to the present invention, $X_1$ is selected from the group consisting of $NR_1$, O, S, Se, $SiR_2R_3$, and $CR_4R_5$, and preferably, $X_1$ may be $NR_1$.

It is preferred that $R_1$ to $R_5$ are each independently selected from the group consisting of hydrogen, a substituted or unsubstituted $C_1$ to $C_{40}$ alkyl group, a substituted or unsubstituted $C_6$ to $C_{60}$ aryl group, a substituted or unsubstituted heteroaryl group having 5 to 60 nuclear atoms, and a substituted or unsubstituted $C_6$ to $C_{60}$ arylamine group.

In this case, the alkyl group, the aryl group, the heteroaryl group, and the arylamine group of $R_1$ to $R_5$ may be substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

In particular, it is further preferred that $R_1$ to $R_4$ are each independently hydrogen, a $C_6$ to $C_{60}$ aryl group (for example: phenyl, naphthyl, and bisphenyl), and a heteroaryl group having 5 to 60 nuclear atoms (for example: pyridine) in consideration of band-gap and thermal stability.

Further, it is preferred that $X_2$ is N or $CR_6$, and $R_6$ is selected from the group consisting of hydrogen, a substituted or unsubstituted $C_1$ to $C_{40}$ alkyl group, a substituted or unsubstituted $C_6$ to $C_{60}$ aryl group, a substituted or unsubstituted heteroaryl group having 5 to 60 nuclear atoms, and a substituted or unsubstituted $C_6$ to $C_{60}$ arylamine group.

In this case, the alkyl group, the aryl group, the heteroaryl group, and the arylamine group of $R_6$ may be substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

Further, in Formula 1, $Y_1$ to $Y_4$ are each independently N or $CR_7$, and in this case, a plurality of $CR_7$'s is the same as or different from each other.

Provided that at least one of $Y_1$ to $Y_4$ is $CR_7$, and is fused with an adjacent group to form the fused ring represented by Formula 2. Preferably, $Y_1$ to $Y_4$ may be all $CR_7$, and at least one of $Y_1$ to $Y_4$ is fused with an adjacent group to form the fused ring represented by Formula 2. For example, $Y_1$ of $Y_1$ to $Y_4$ may be $CR_7$, and $Y_1$ may be fused with $Y_2$ to form the fused ring represented by Formula 2. Alternatively, $Y_1$ and $Y_3$ of $Y_1$ to $Y_4$ may be each $CR_7$, and $Y_1$ and $Y_3$ may be fused with $Y_2$ and $Y_4$, respectively, to form the fused ring represented by Formula 2.

It is preferred that $R_7$ is selected from the group consisting of hydrogen, a substituted or unsubstituted $C_1$ to $C_{40}$ alkyl group, a substituted or unsubstituted $C_6$ to $C_{60}$ aryl group, a substituted or unsubstituted heteroaryl group having 5 to 60 nuclear atoms, and a substituted or unsubstituted $C_6$ to $C_{60}$ arylamine group, and in this case, may be fused with an adjacent group to form a fused aromatic ring or a fused heteroaromatic ring.

In this case, the alkyl group, the aryl group, the heteroaryl group, and the arylamine group of $R_7$ may be substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

In the fused ring represented by Formula 2, $X_3$ is selected from the group consisting of O, S, Se, $N(Ar_1)$, $C(Ar_2)(Ar_3)$, and $Si(Ar_4)(Ar_5)$, and preferably, $X_3$ may be $N(Ar_1)$.

It is preferred that $Ar_1$ to $Ar_5$ are selected from the group consisting of hydrogen, a substituted or unsubstituted $C_1$ to $C_{40}$ alkyl group, a substituted or unsubstituted $C_6$ to $C_{60}$ aryl group, a substituted or unsubstituted heteroaryl group having 5 to 60 nuclear atoms, and a substituted or unsubstituted $C_6$ to $C_{60}$ arylamine group.

In this case, the alkyl group, the aryl group, the heteroaryl group, and the arylamine group of $Ar_1$ to $Ar_5$ may be substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

Preferably, $Ar_1$ to $Ar_5$ may be each independently selected from the group consisting of a substituted or unsubstituted $C_6$ to $C_{60}$ aryl group, a substituted or unsubstituted heteroaryl group having 5 to 60 nuclear atoms, and a substituted or unsubstituted $C_6$ to $C_{60}$ arylamine group.

In this case, the aryl group, the heteroaryl group, and the arylamine group of $Ar_1$ to $Ar_5$ may be substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

Further, in Formula 2, $Y_5$ to $Y_8$ are each independently N or $CR_8$, and preferably, $Y_5$ to $Y_8$ may be all $CR_8$. In this case, a plurality of $CR_8$'s is the same as or different from each other.

It is preferred that $R_8$ is selected from the group consisting of hydrogen, a substituted or unsubstituted $C_1$ to $C_{40}$ alkyl group, a substituted or unsubstituted $C_6$ to $C_{60}$ aryl group, a substituted or unsubstituted heteroaryl group having 5 to 60 nuclear atoms, and a substituted or unsubstituted $C_6$ to $C_{60}$ arylamine group, and in this case, may be fused with an adjacent group to form a fused aromatic ring or a fused heteroaromatic ring.

In this case, the alkyl group, the aryl group, the heteroaryl group, and the arylamine group of $R_8$ may be substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

In the compound of Formula 1 according to the present invention, $R_1$ to $R_8$ and $Ar_1$ to $Ar_5$ may be each independently selected from the group consisting of hydrogen, and the following substituents S1 to S169, but are not limited thereto.

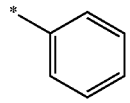

S1

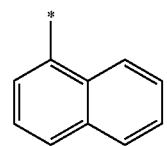

S2

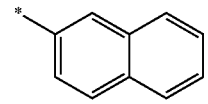

S3

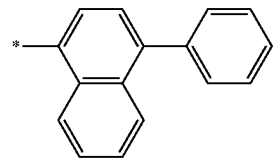

S4

-continued

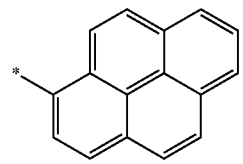

S5

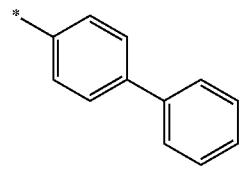

S6

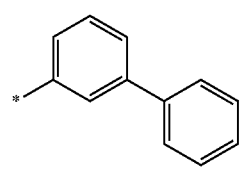

S7

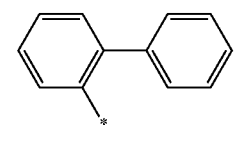

S8

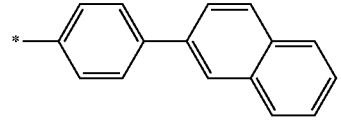

S9

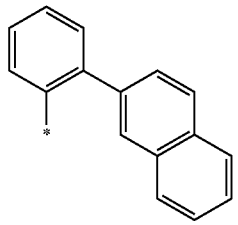

S10

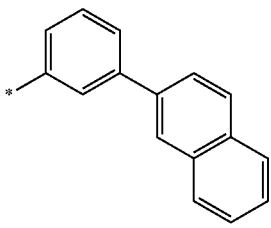

S11

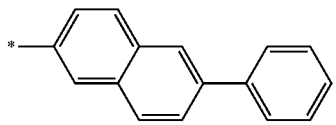

S12

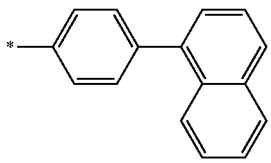

S13

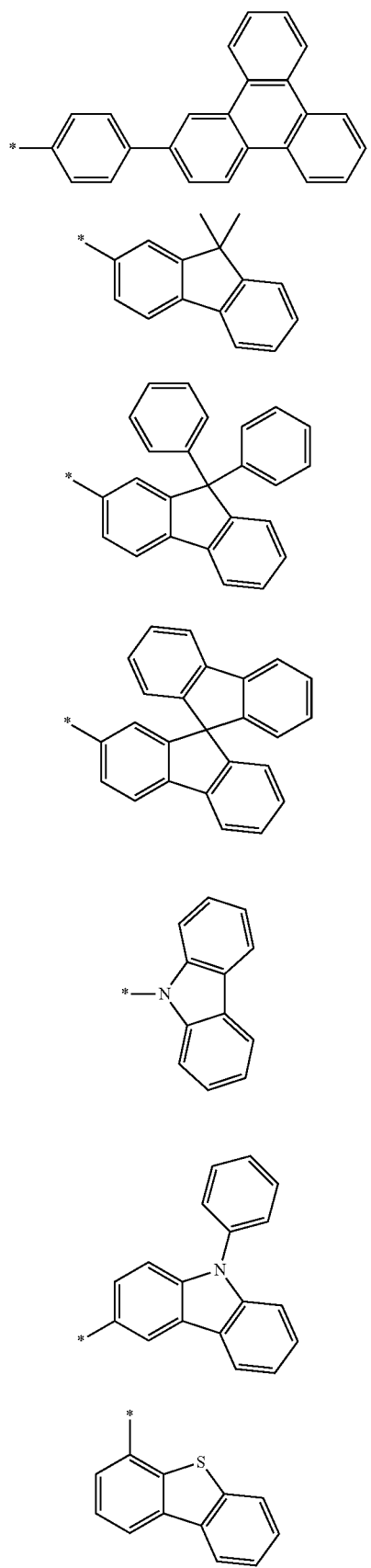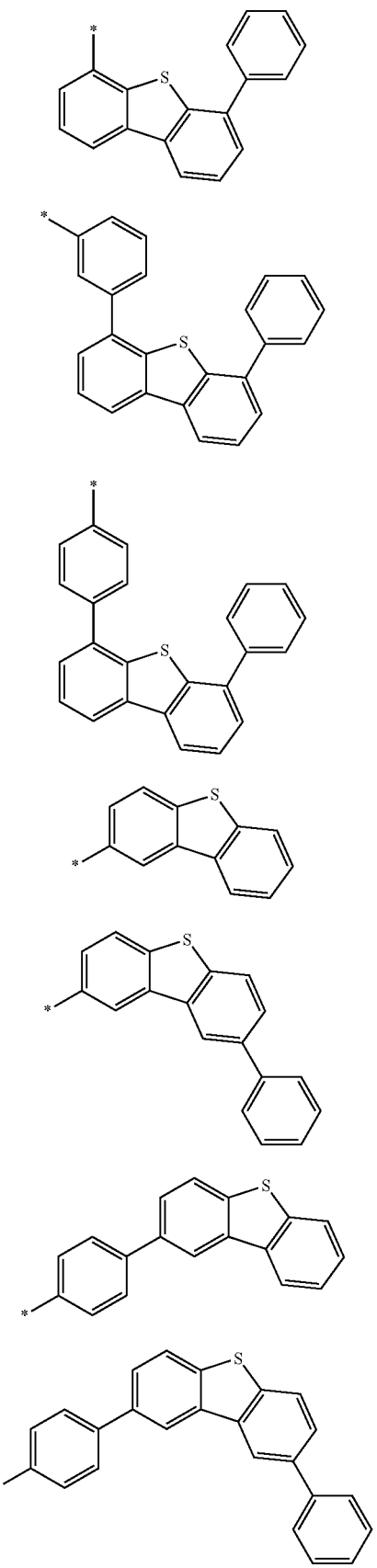

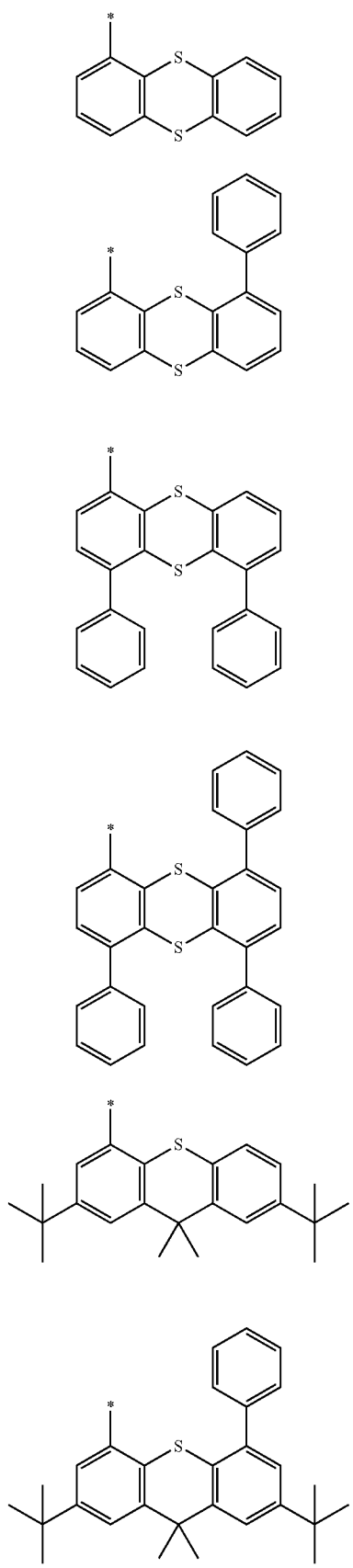
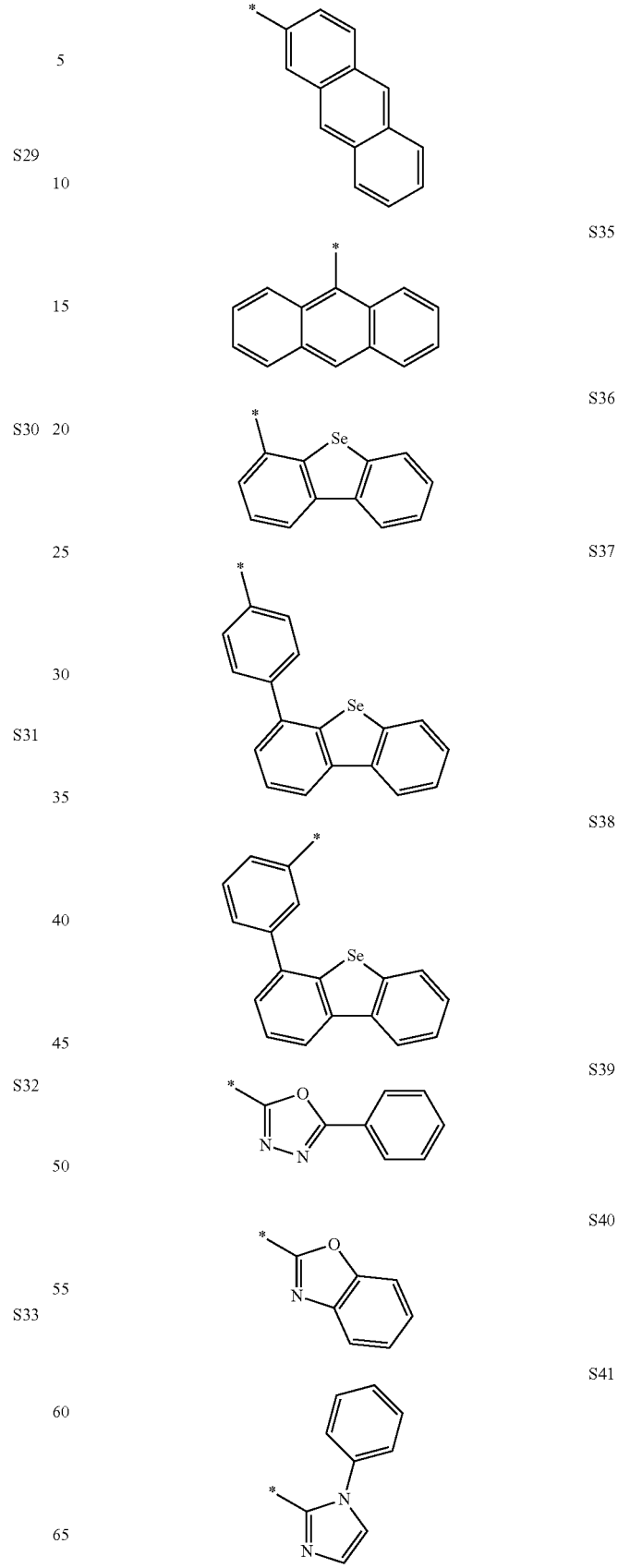

-continued
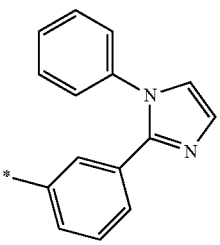 S42
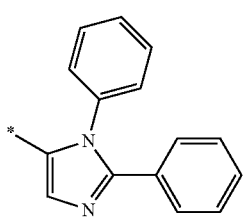 S43
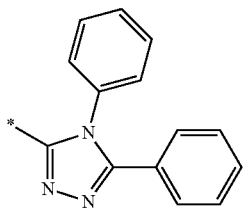 S44
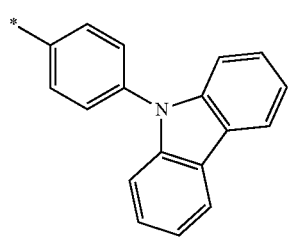 S45
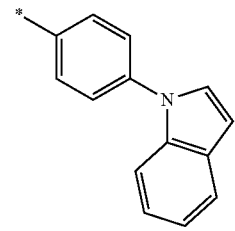 S45
 S47
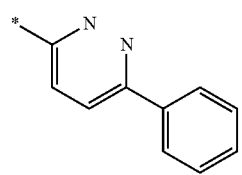 S48
-continued
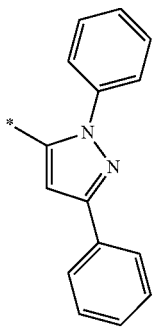 S49
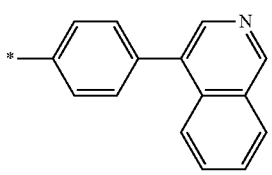 S50
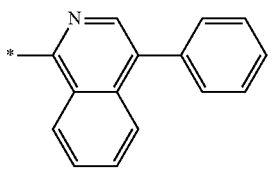 S51
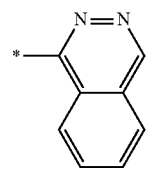 S52
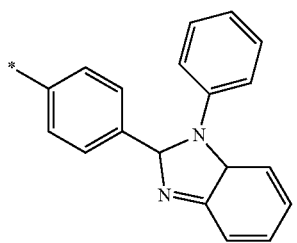 S53
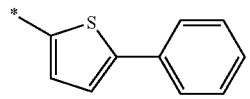 S54
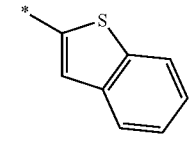 S55
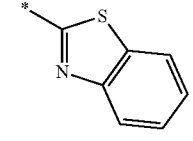 S56
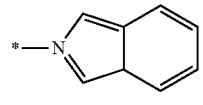 S57

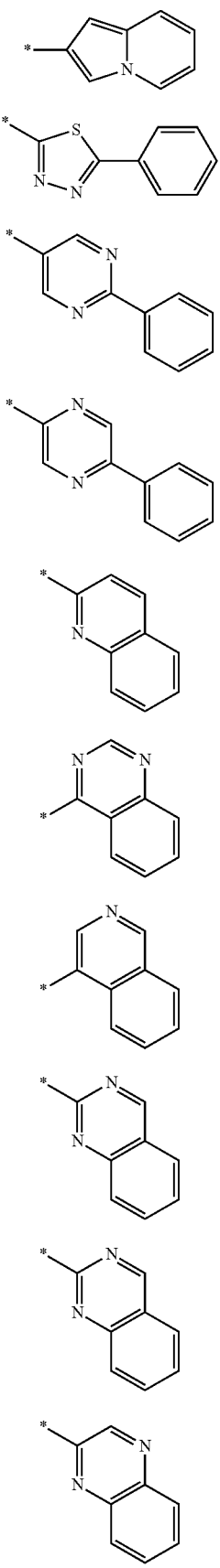
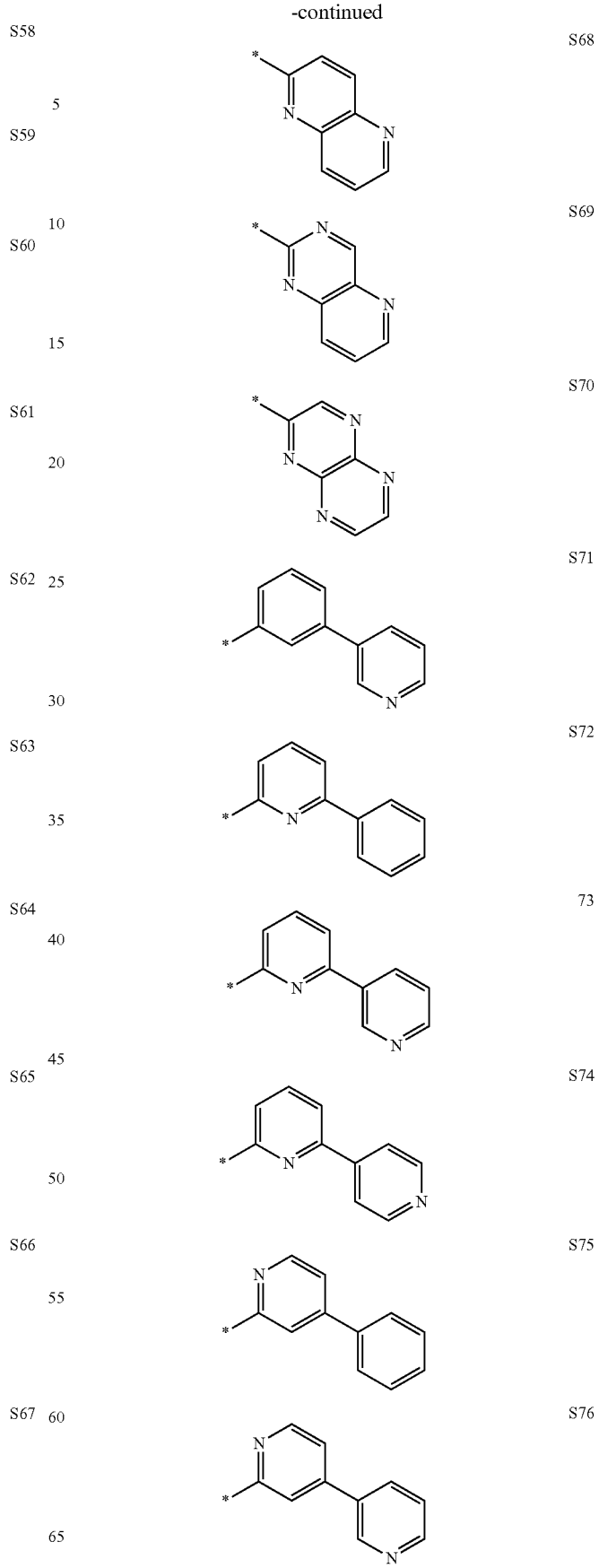

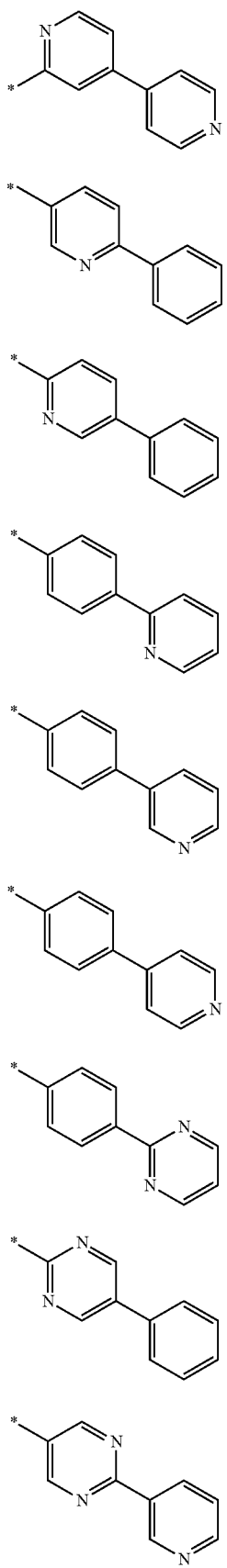
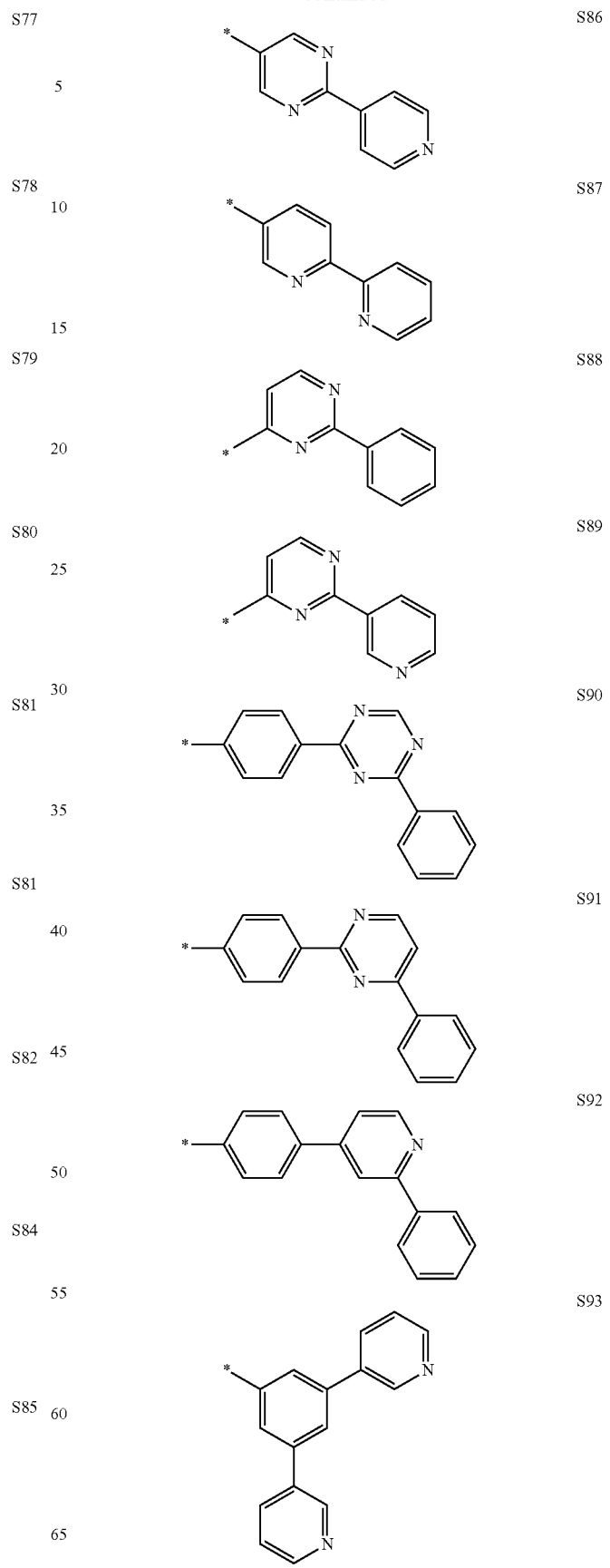

-continued
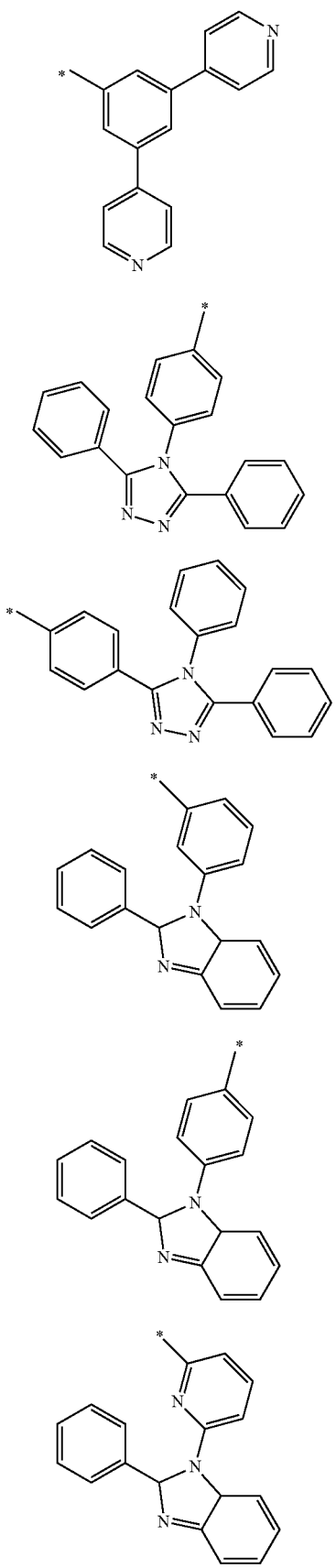
S94
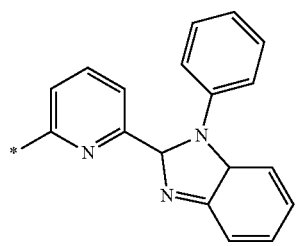
S95
S96
S97
S98
S99
-continued
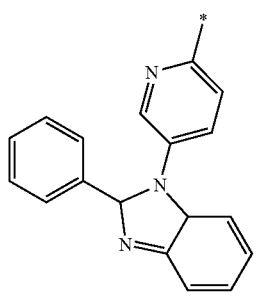
S100
S101
S102
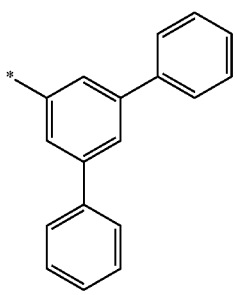
S103
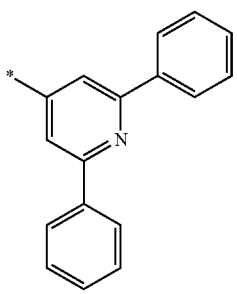
S104
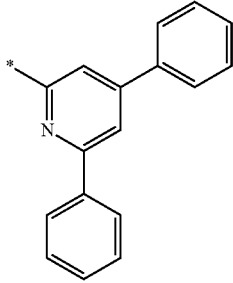

-continued
S105
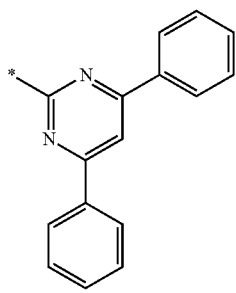
S106
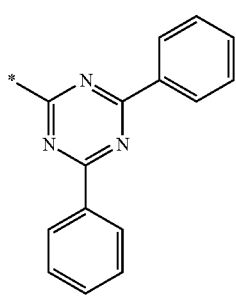
S107
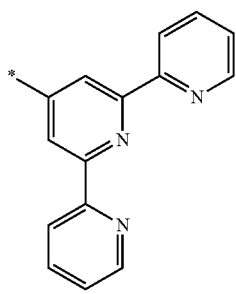
S108
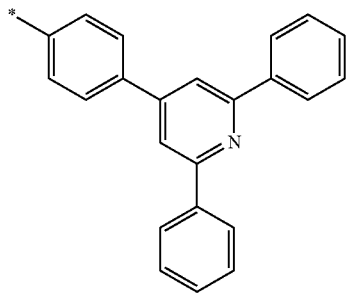
S109
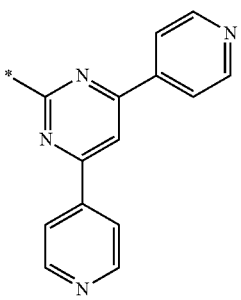
-continued
S110
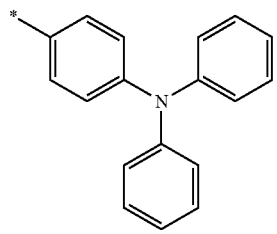
S111
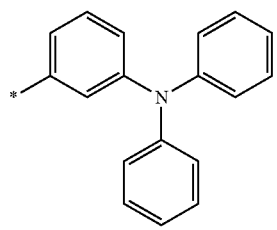
S112
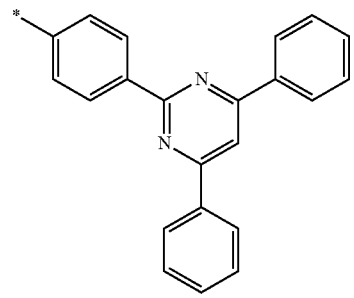
S113
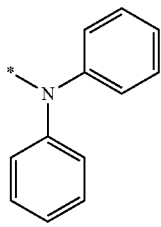
S114
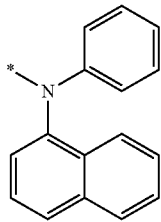
S115
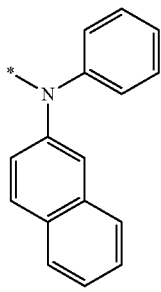

S116 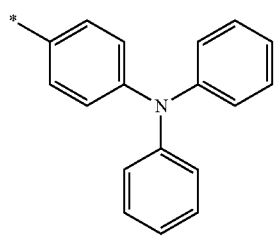
S117 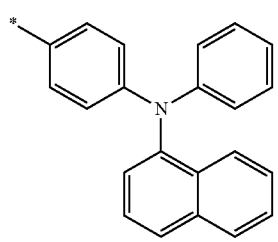
S118 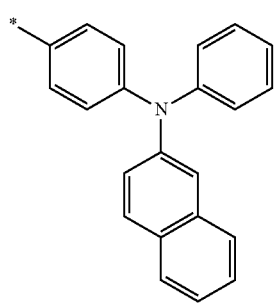
S119 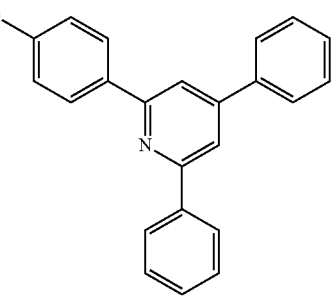
S120 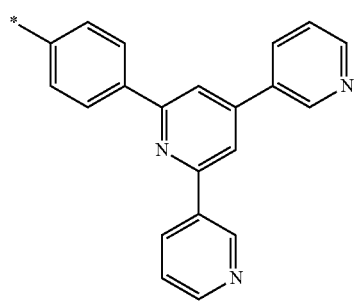
S121 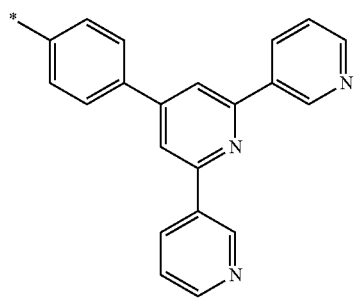
S122 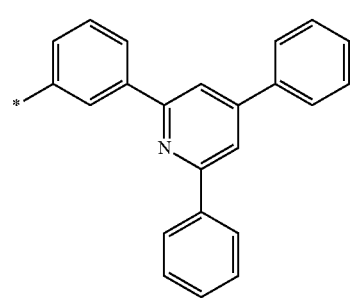
S123 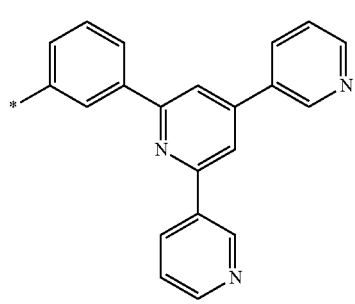
S124 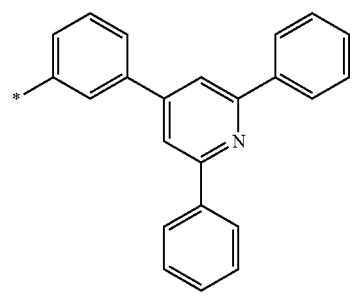
S125 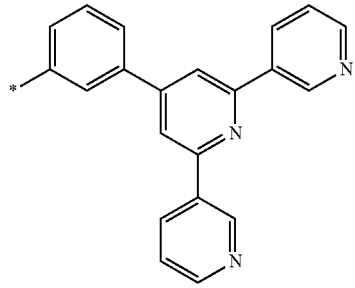

-continued
S126
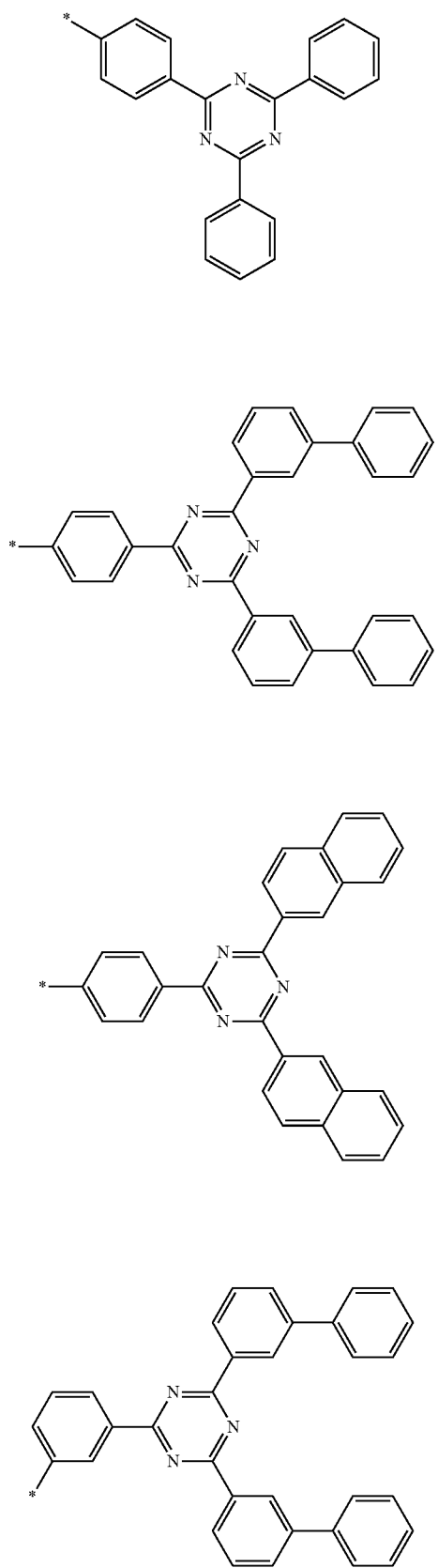
S127
S128
S129
-continued
S130
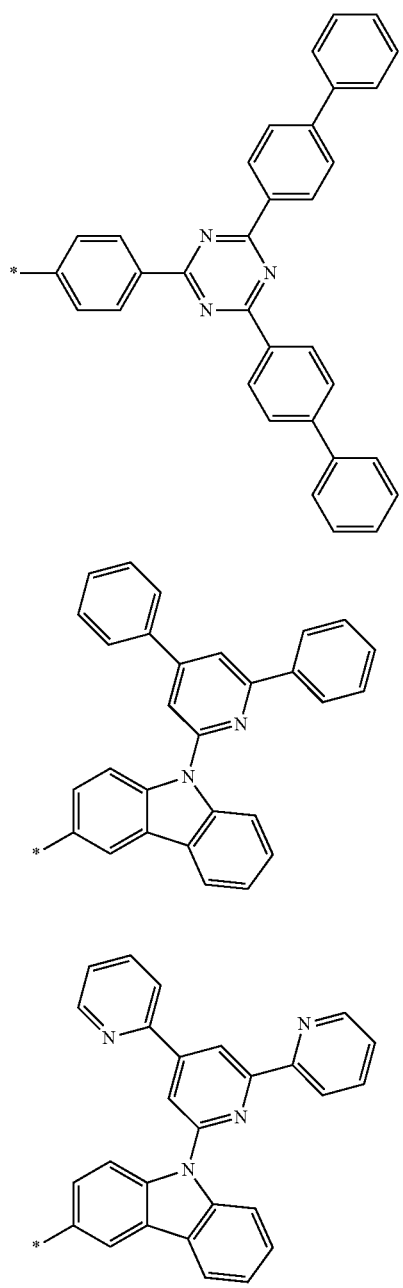
S131
S132
S133

S134
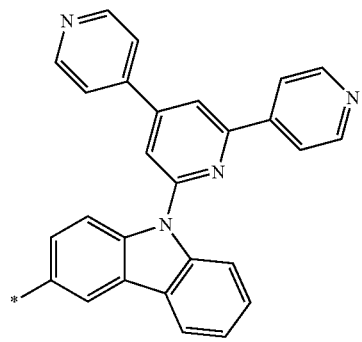
S135
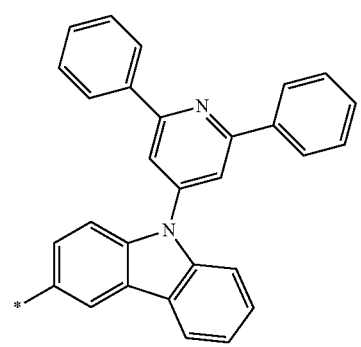
S136
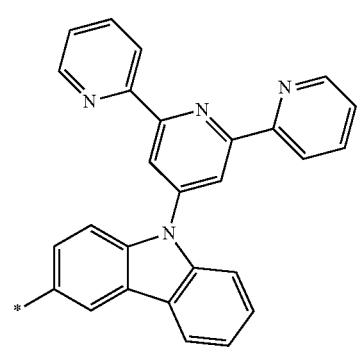
S137
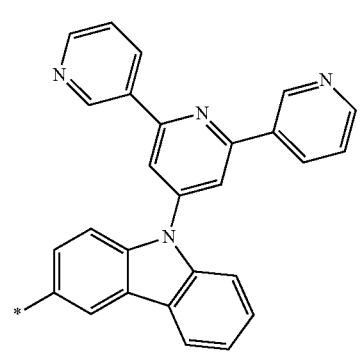
S138
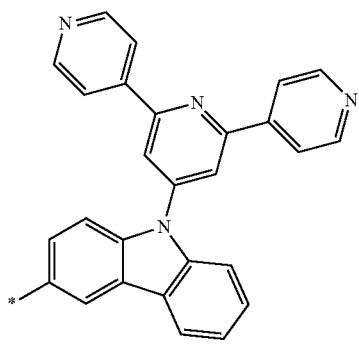
S139
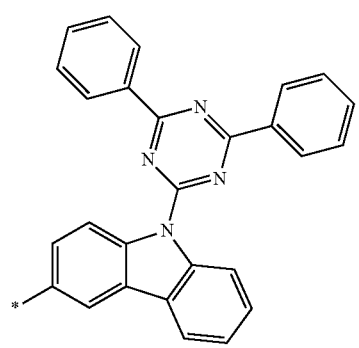
S140
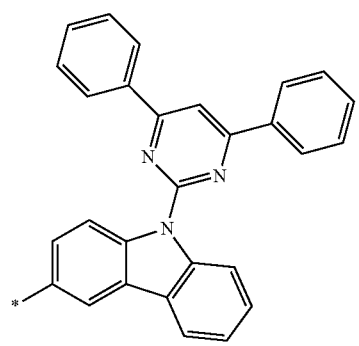
S141
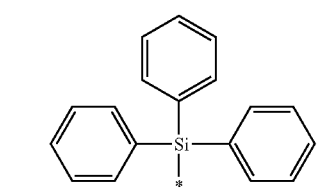
S142
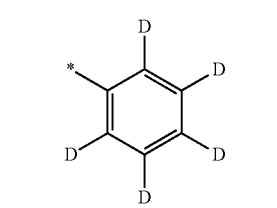
S143
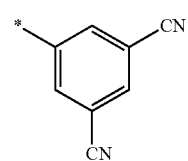

-continued
S144 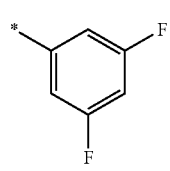
S145 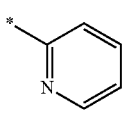
S146 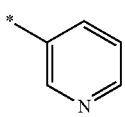
S147 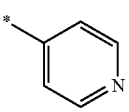
S148 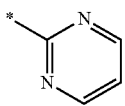
S149 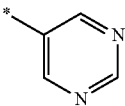
S150 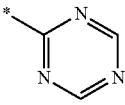
S151 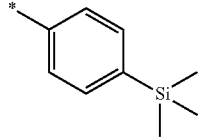
S152 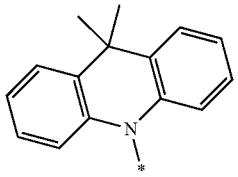
S153 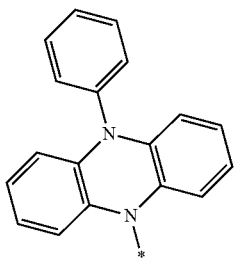
S154 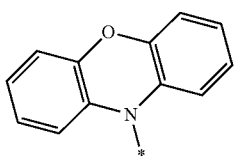
-continued
S155 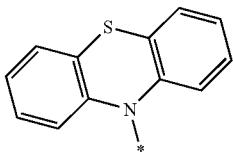
S156 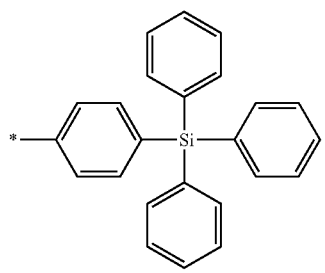
S157 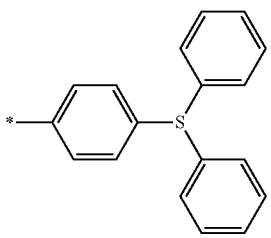
S158 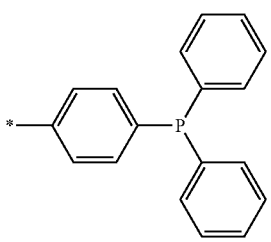
S159 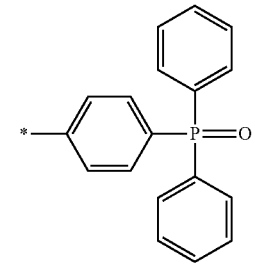
S160 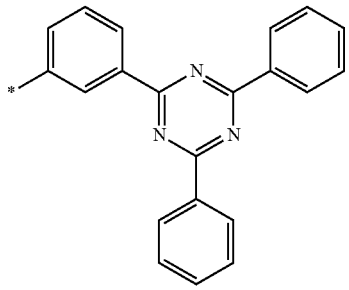

-continued
S161
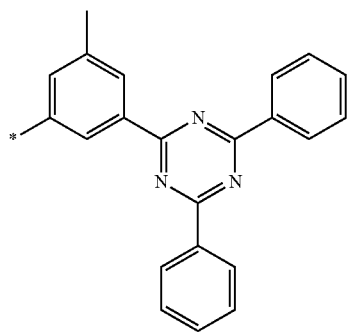
S162
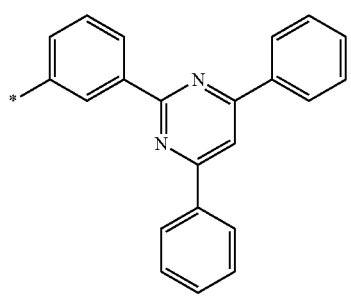
S163
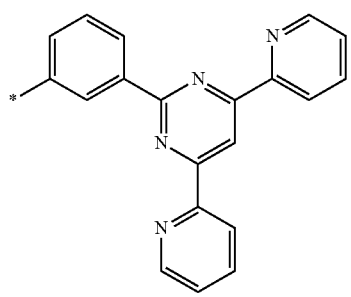
S164
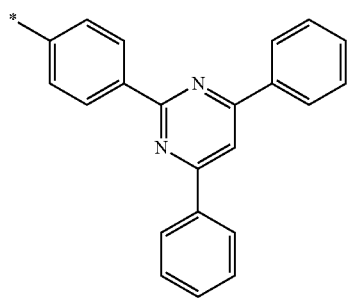
S165
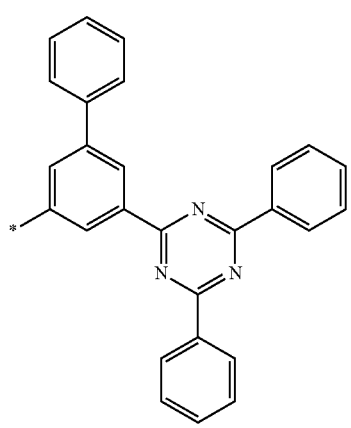
-continued
S166
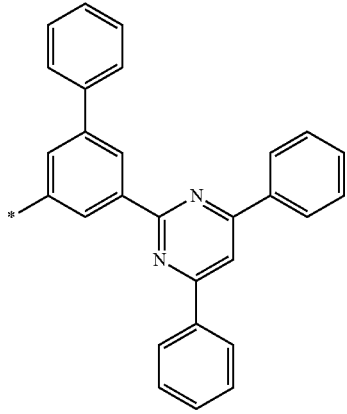
S167
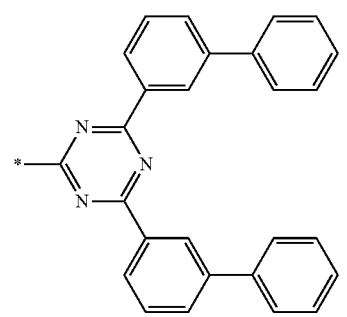
S168
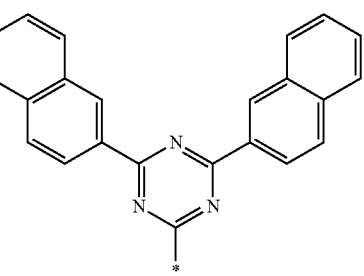
S169
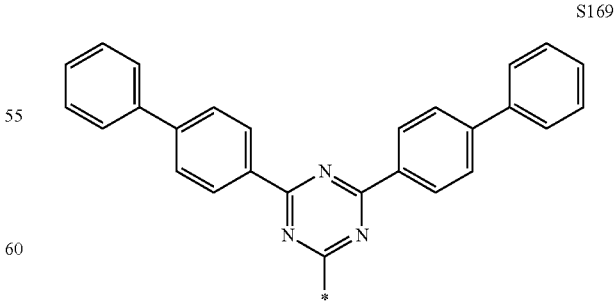
Preferably, $R_1$ to $R_8$ and $Ar_1$ to $Ar_5$ may be each independently selected from the group consisting of hydrogen, and the following substituents A1 to A40, but are not limited thereto.

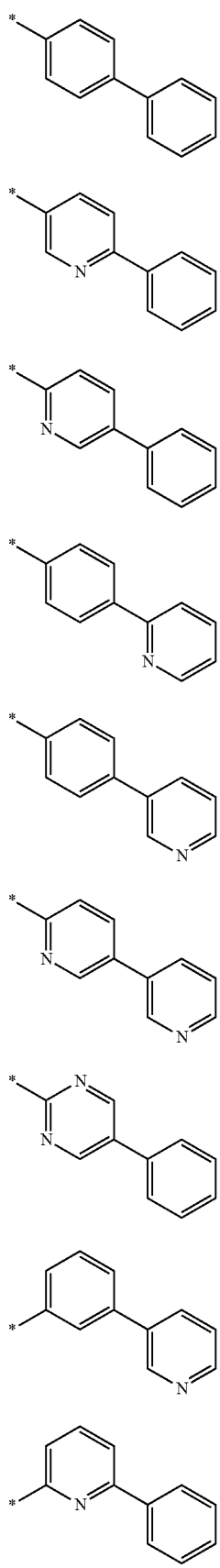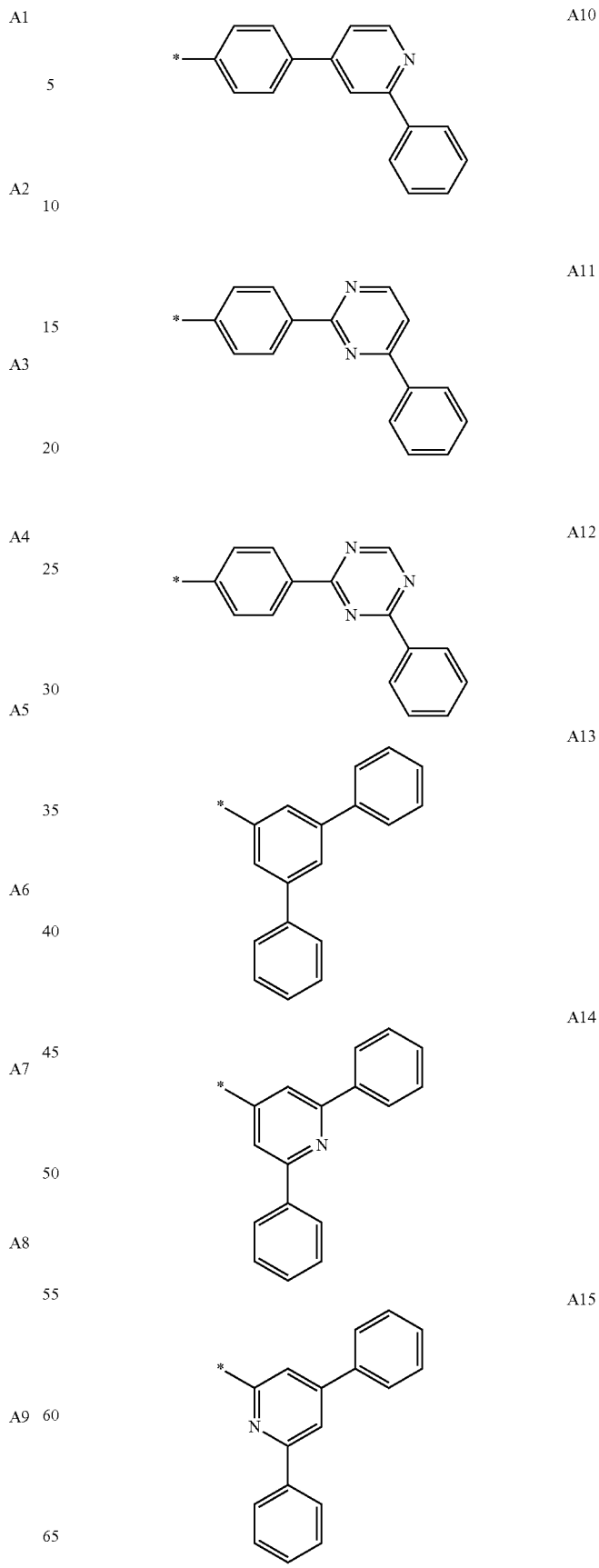

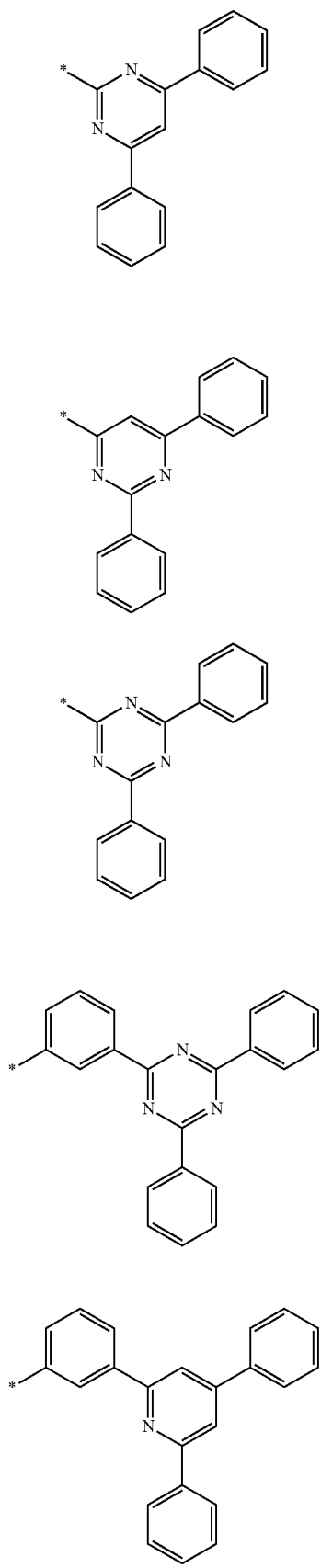
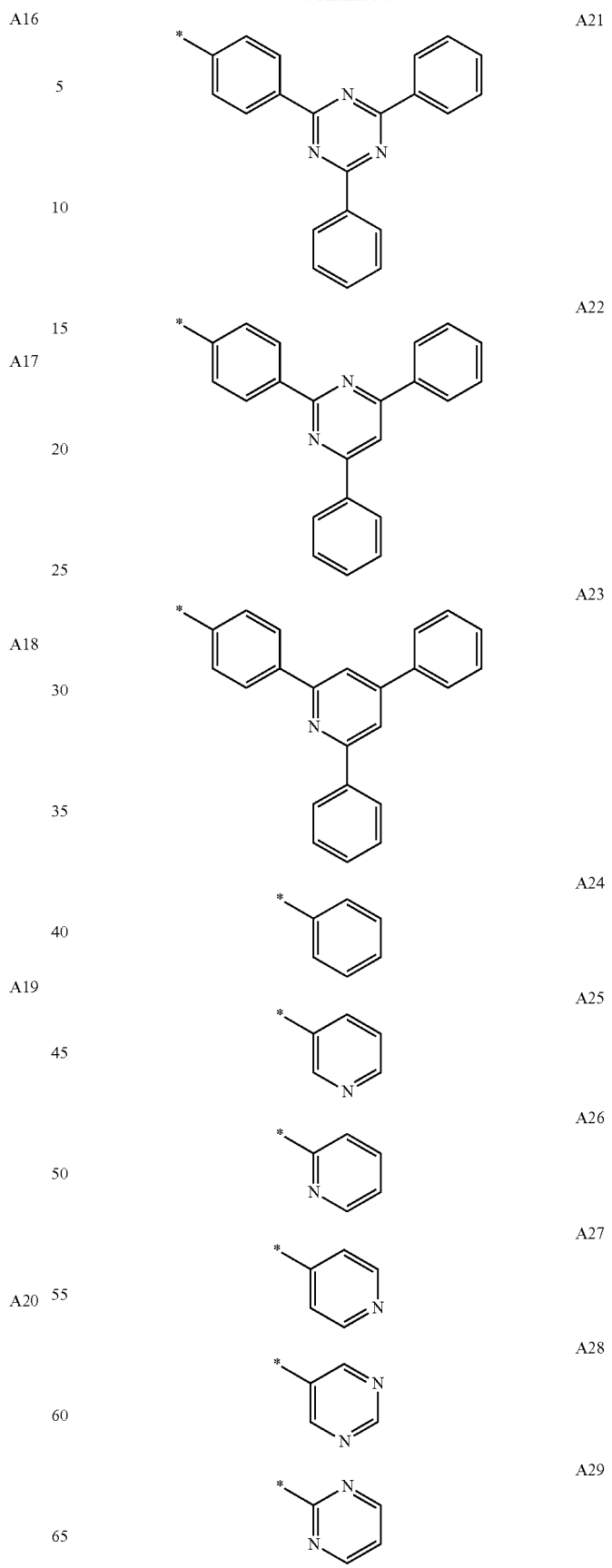

A30
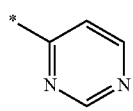
A31
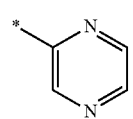
A32
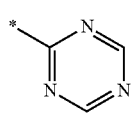
A33
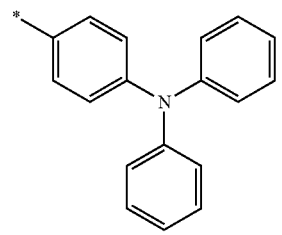
A34
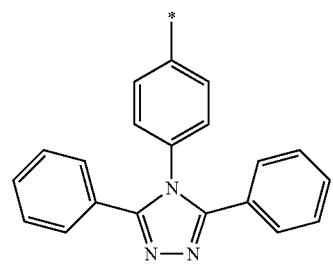
A35
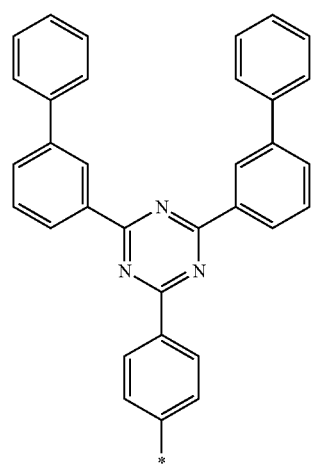
A36
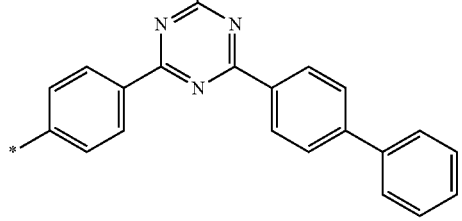
A37
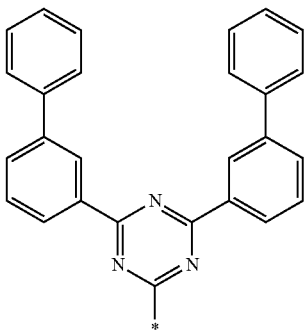
A38
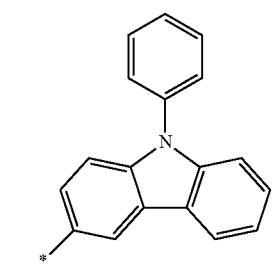
A39
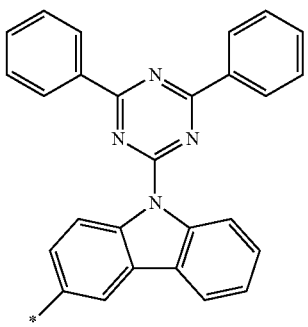

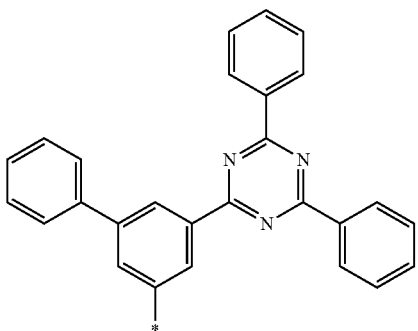

A40

Examples of the compound represented by Formula 1 according to the present invention include compounds represented by the following Formulae 3 to 12, but are not limited thereto.

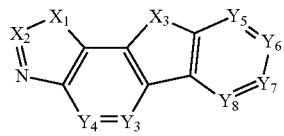

[Formula 3]

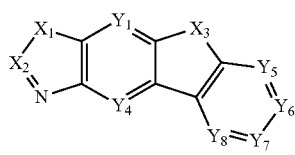

[Formula 4]

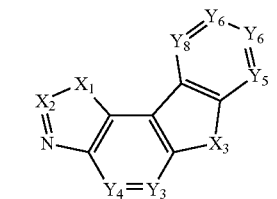

[Formula 5]

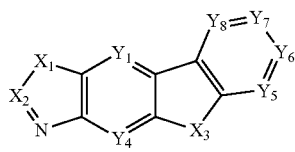

[Formula 6]

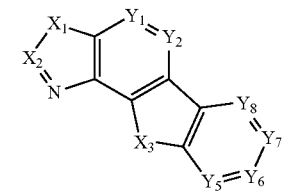

[Formula 7]

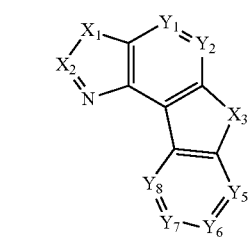

[Formula 8]

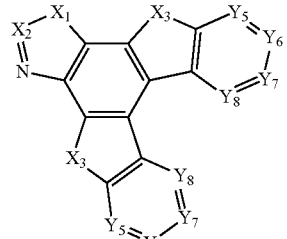

[Formula 9]

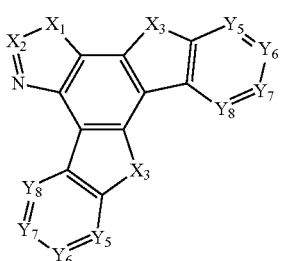

[Formula 10]

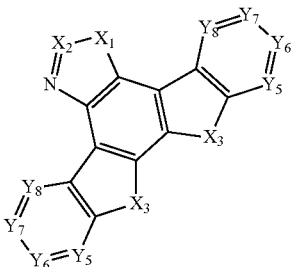

[Formula 11]

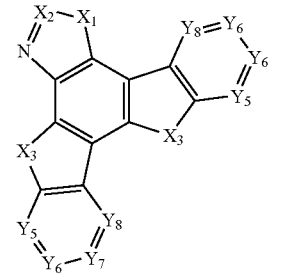

[Formula 12]

In Formulae 3 to 12, $X_1$ to $X_3$ are each independently the same as those defined in Formula 1, and in this case, a plurality of $X_3$'s is the same as or different from each other;

$Y_1$ to $Y_4$ are each independently N or $CR_7$, and in this case, a plurality of $CR_7$'s is the same as or different from each other, and $R_7$ is the same as that defined in Formula 1; and $Y_5$ to $Y_8$ are each independently the same as those defined in Formula 1, and in this case, a plurality of $Y_5$'s is the same as or different from each other, a plurality of $Y_6$'s is the same as or different from each other, a plurality of $Y_7$'s is the same as or different from each other, and a plurality of $Y_8$'s is the same as or different from each other.

Specific examples of the compound represented by Formula 1 include compounds represented by the following Formulae C-1 to C-192, but are not limited thereto. In the following Formulae C-1 to C-192, $R_1$ to $R_5$ and $Ar_1$ to $Ar_5$ are each independently the same as those defined in Formula 1, and in this case, a plurality of $Ar_1$'s is the same as or different from each other.

C-1 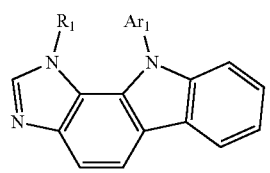
C-2 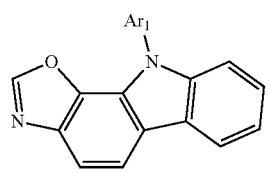
C-3 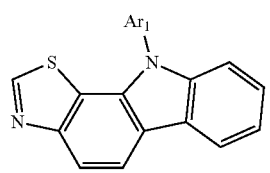
C-4 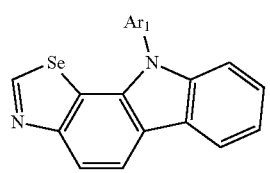
C-5 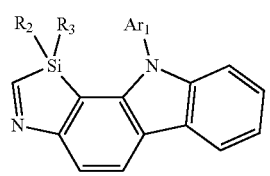
C-6 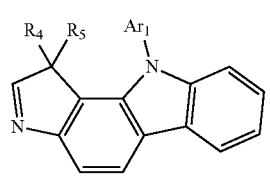
C-7 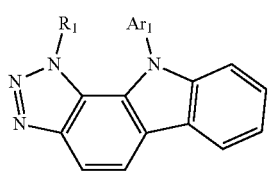
C-8 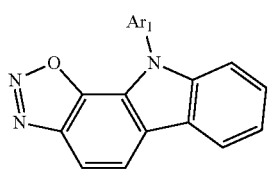
C-9 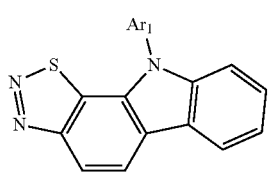
-continued
C-10 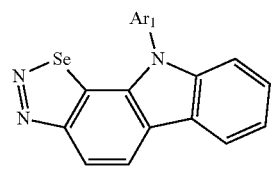
C-11 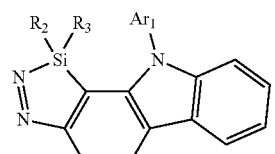
C-12 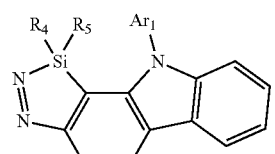
C-13 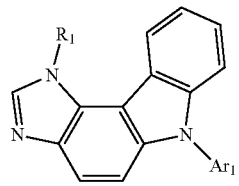
C-14 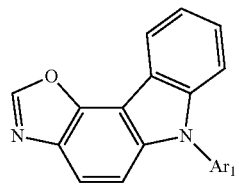
C-15 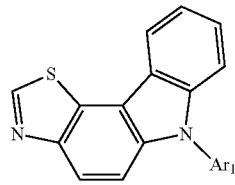
C-16 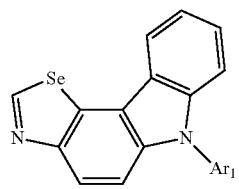
C-17 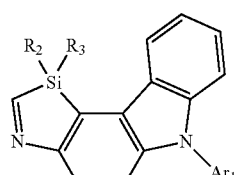

-continued
C-18
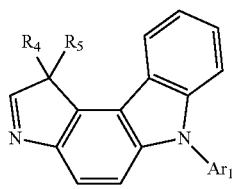
C-19
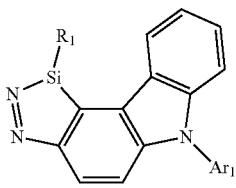
C-20
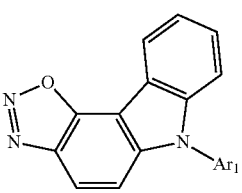
C-21
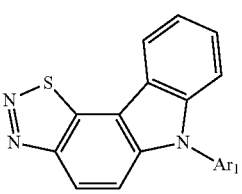
C-22
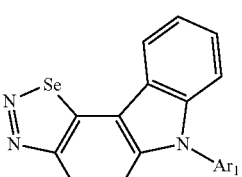
C-23
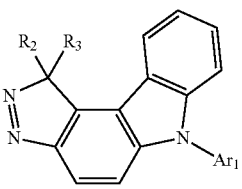
C-24
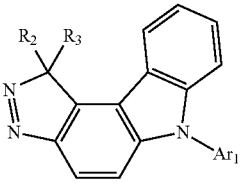
C-25
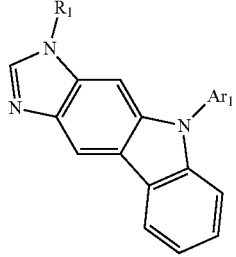
-continued
C-26
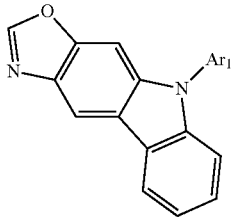
C-27
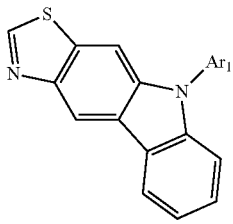
C-28
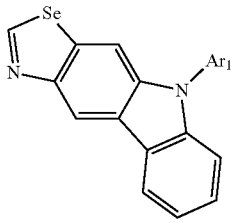
C-29
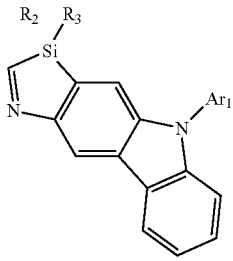
C-30
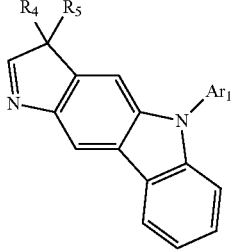
C-31
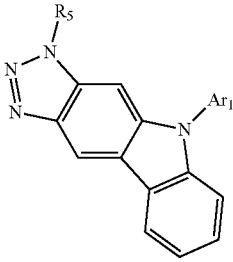

| | |
|---|---|
| C-32 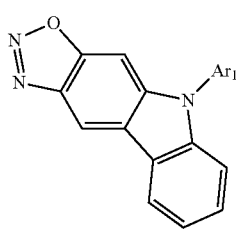 | C-38 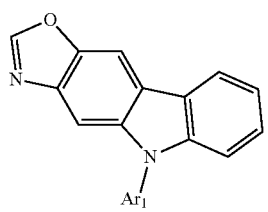 |
| C-33 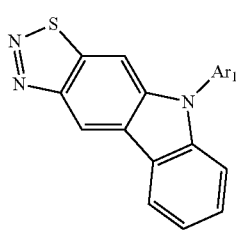 | C-39 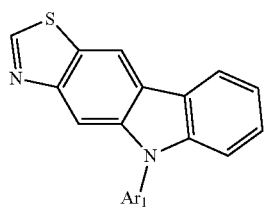 |
| C-34 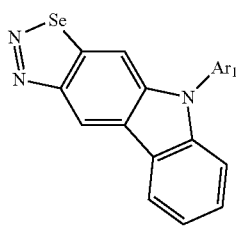 | C-40 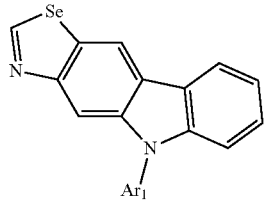 |
| C-35 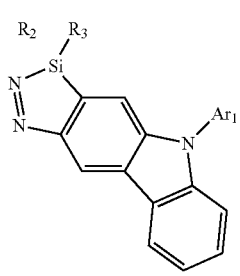 | C-41 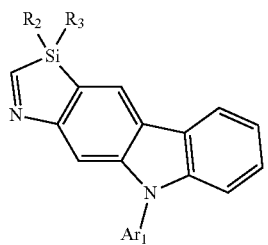 |
| C-36 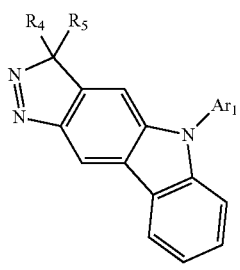 | C-42 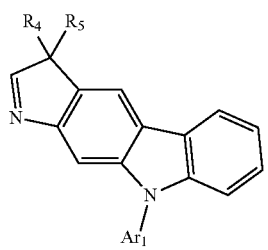 |
| C-37 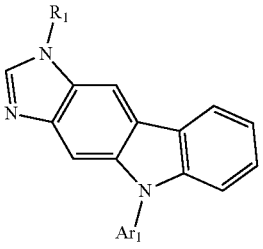 | C-43 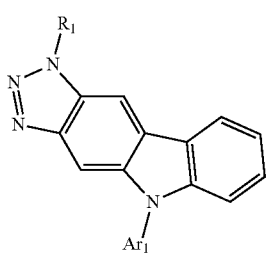 |
| | C-44 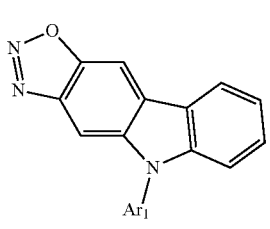 |

-continued
C-45
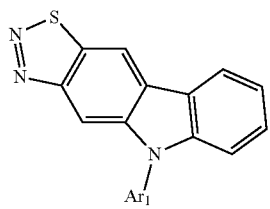
C-46
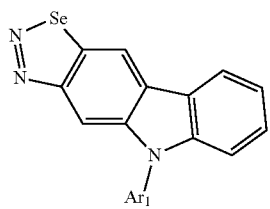
C-47
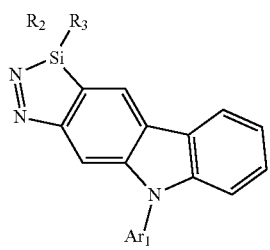
C-48
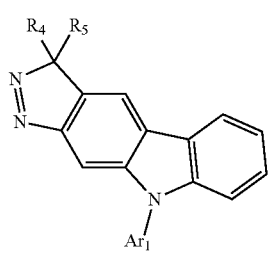
C-49
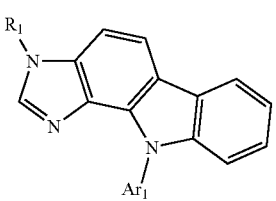
C-50
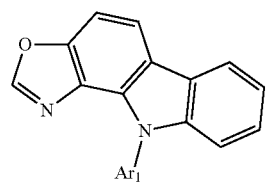
C-51
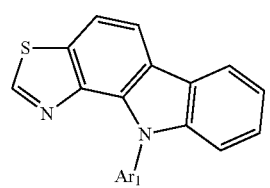
-continued
C-52
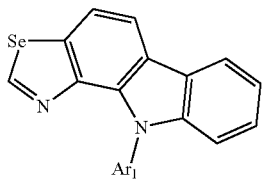
C-53
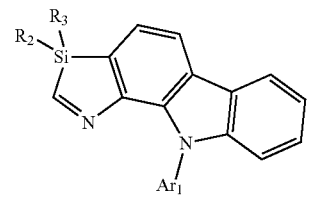
C-54
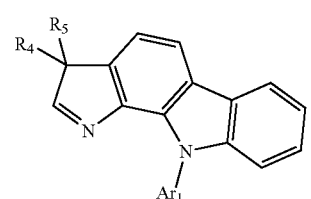
C-55
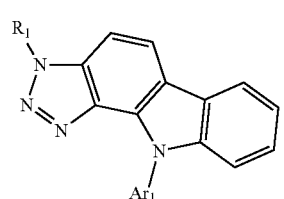
C-56
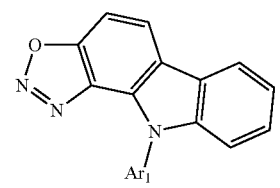
C-57
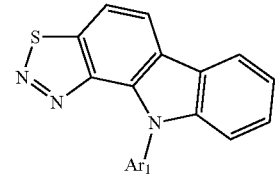
C-58
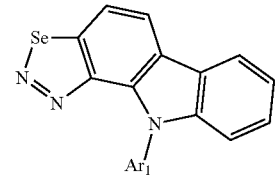
C-59
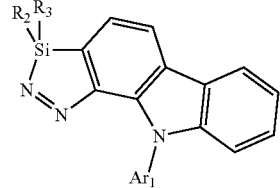

-continued
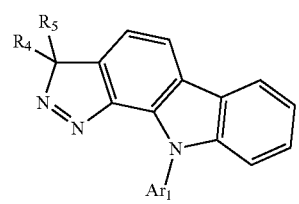
C-60
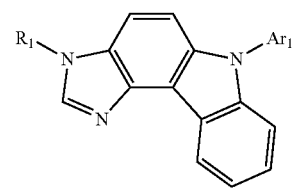
C-61
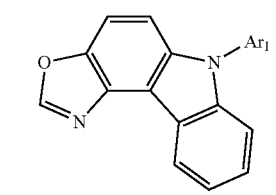
C-62
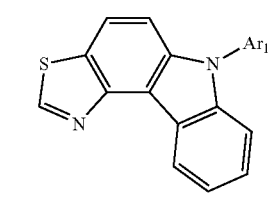
C-63
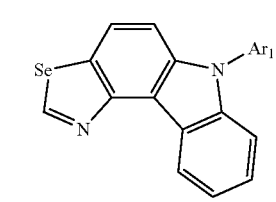
C-64
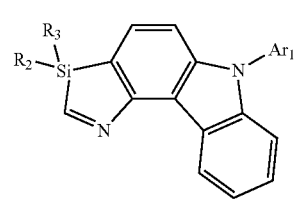
C-65
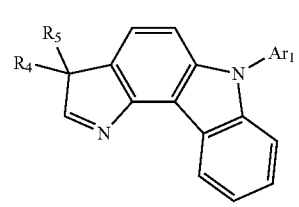
C-66
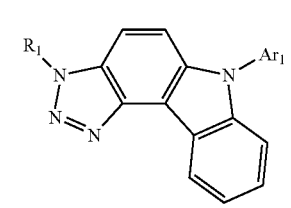
C-67
-continued
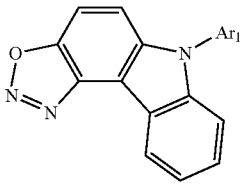
C-68
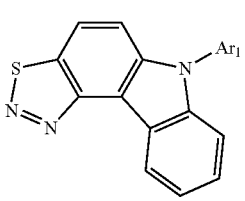
C-69
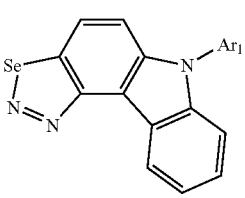
C-70
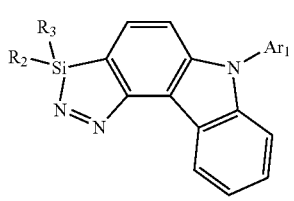
C-71
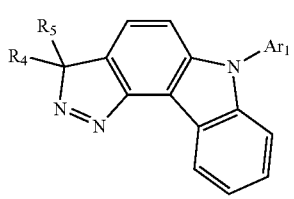
C-72
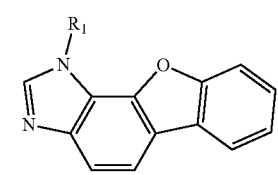
C-73
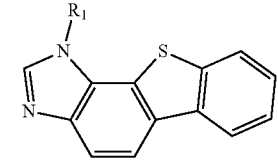
C-74
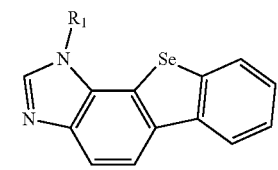
C-75

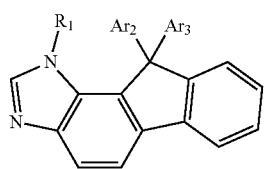 C-76
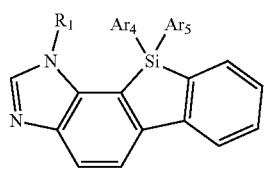 C-77
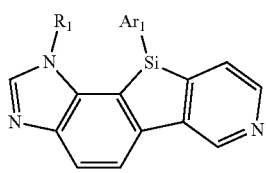 C-78
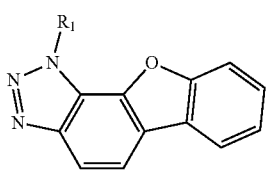 C-79
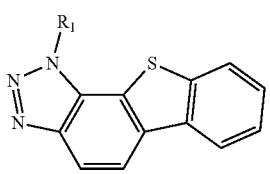 C-80
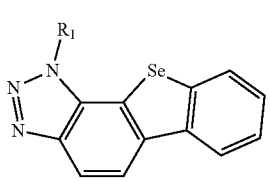 C-81
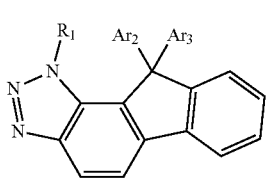 C-82
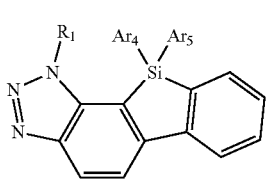 C-83
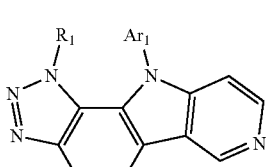 C-84
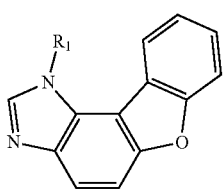 C-85
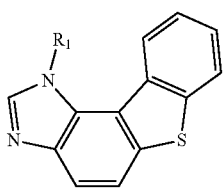 C-86
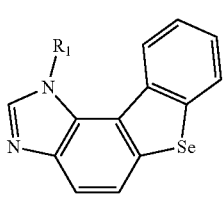 C-87
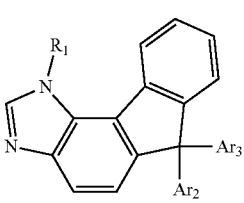 C-88
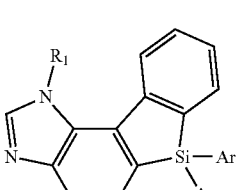 C-89
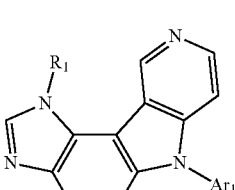 C-90
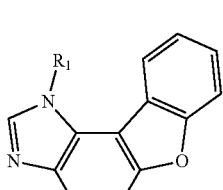 C-91
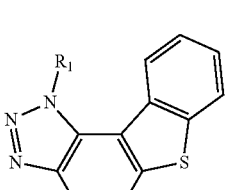 C-92

-continued
C-93
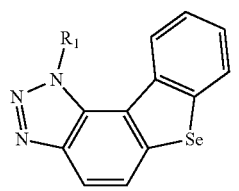
C-94
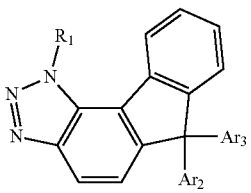
C-95
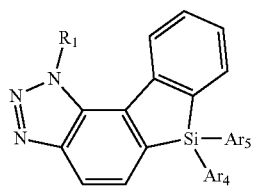
C-96
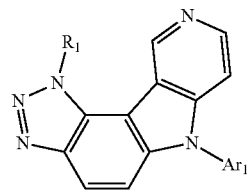
C-97
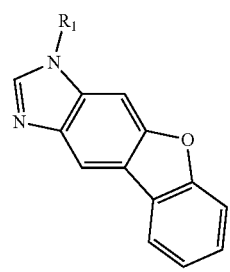
C-98
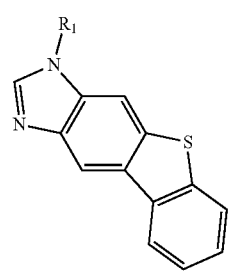
C-99
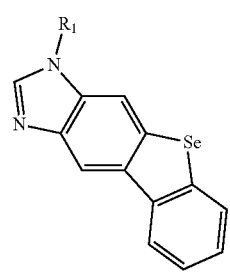
-continued
C-100
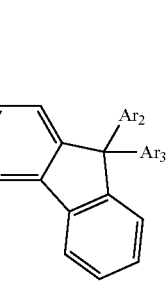
C-101
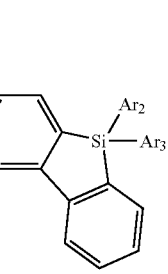
C-102
C-103
C-104
C-105

C-106
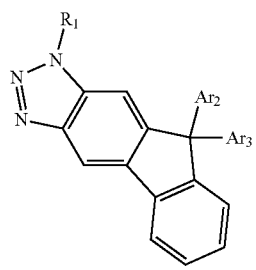
C-107
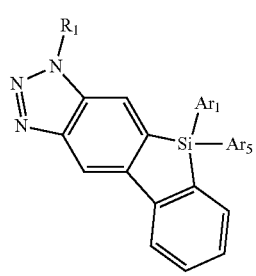
C-108
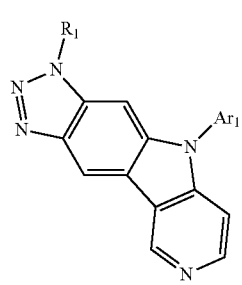
C-109
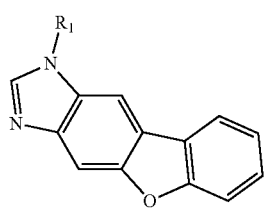
C-110
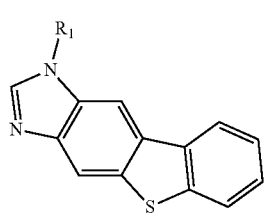
C-111
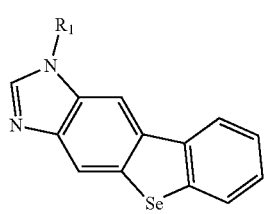
C-112
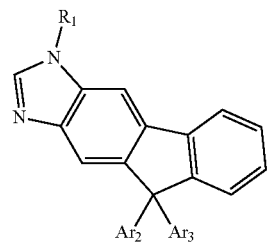
C-113
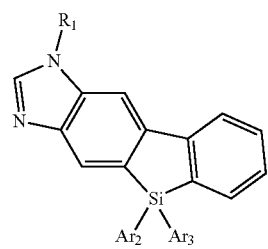
C-114
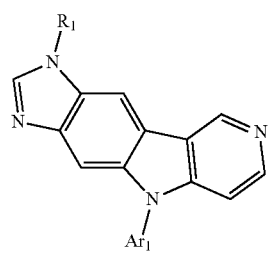
C-115
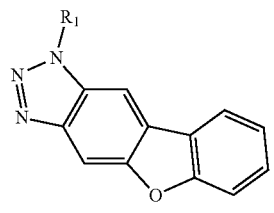
C-116
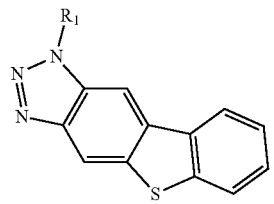
C-117
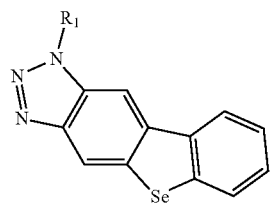
C-118
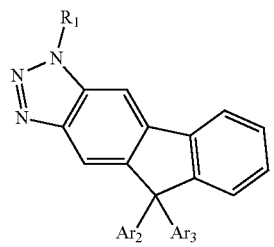

C-119 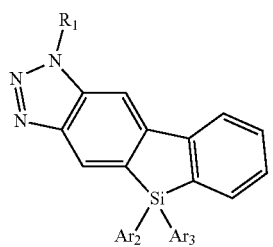
C-120 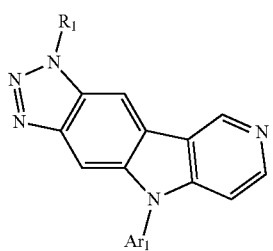
C-121 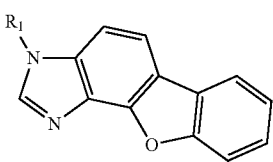
C-122 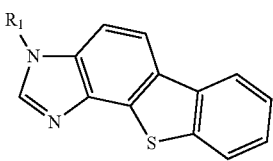
C-123 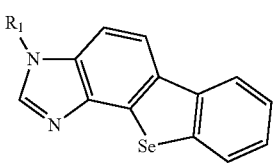
C-124 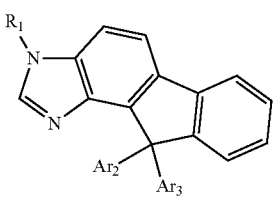
C-125 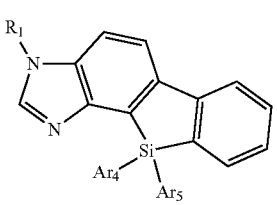
C-126 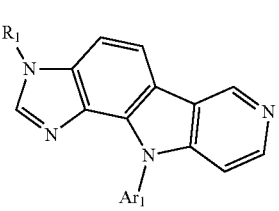
C-127 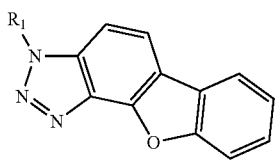
C-128 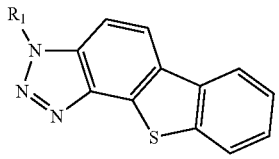
C-129 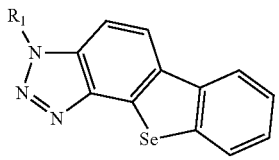
C-130 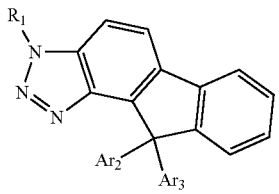
C-131 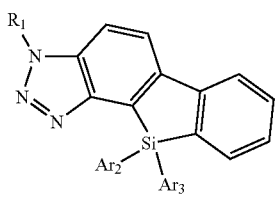
C-132 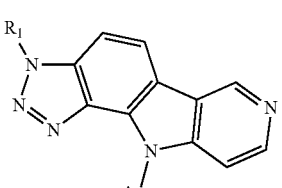
C-133 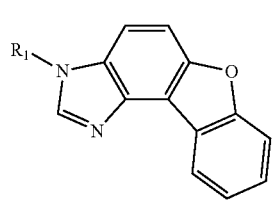
C-134 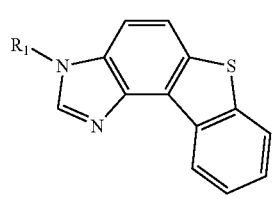

C-135 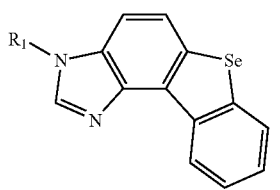
C-136 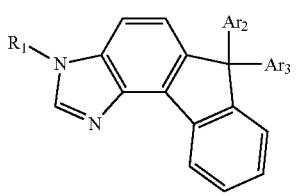
C-137 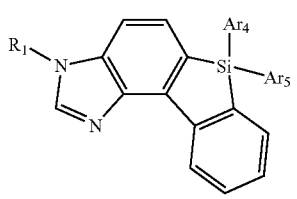
C-138 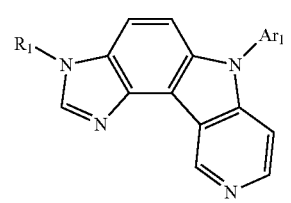
C-139 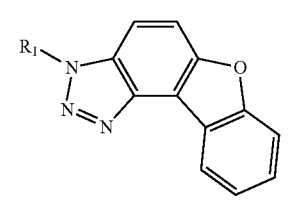
C-140 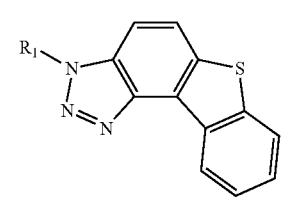
C-141 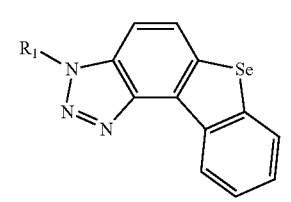
C-142 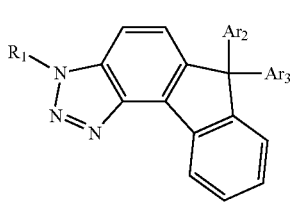
C-143 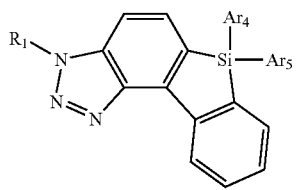
C-144 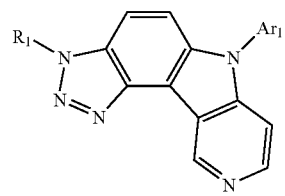
C-145 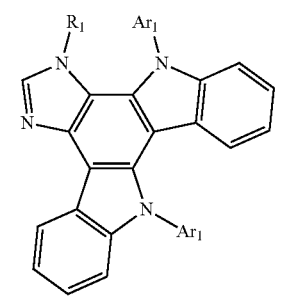
C-146 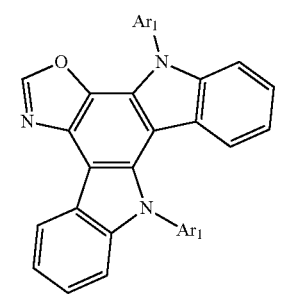
C-147 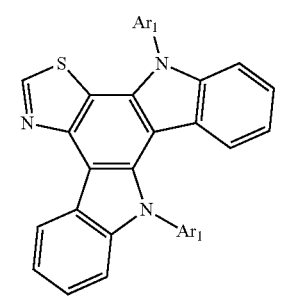
C-148 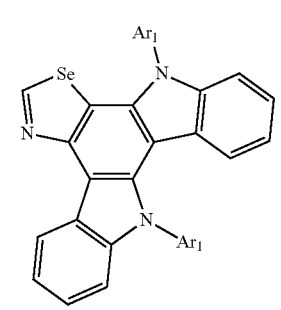

-continued
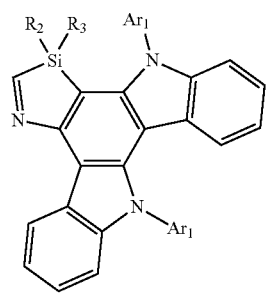
C-149
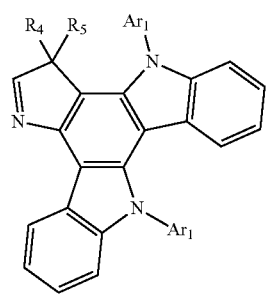
C-150
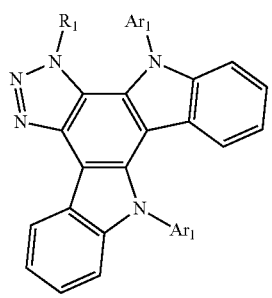
C-151
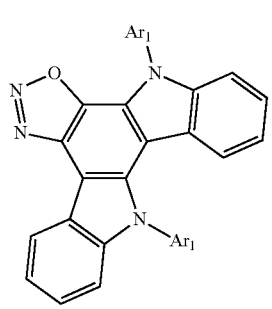
C-152
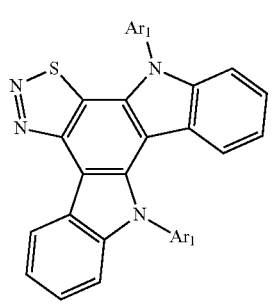
C-153
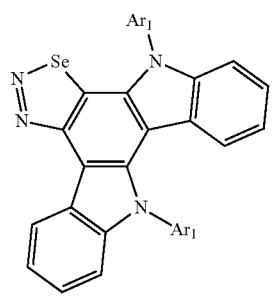
C-154
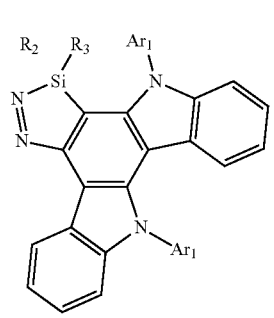
C-155
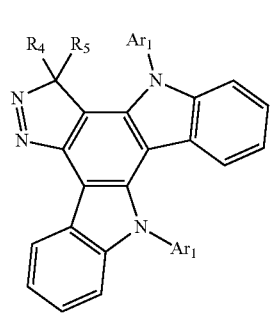
C-156
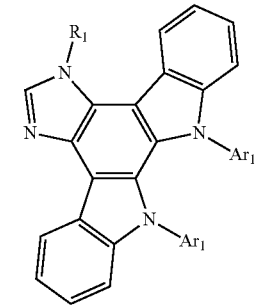
C-157
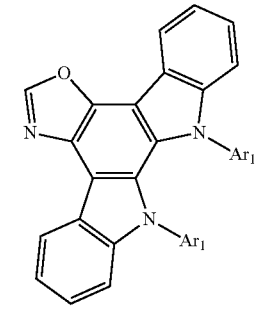
C-158

C-159
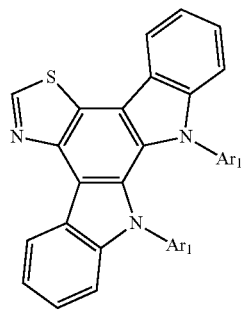
C-160
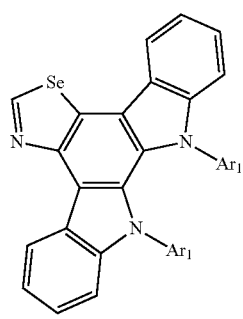
C-161
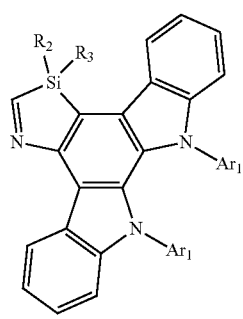
C-162
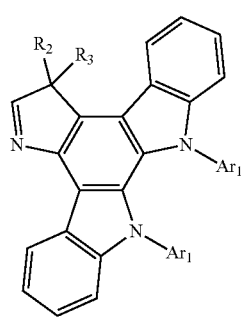
C-163
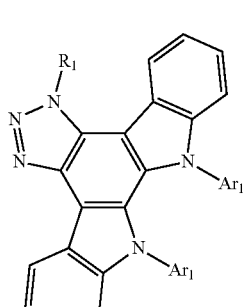
C-164
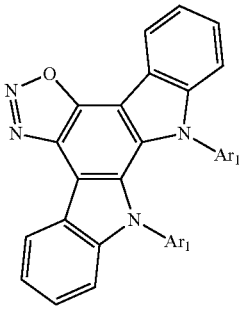
C-165
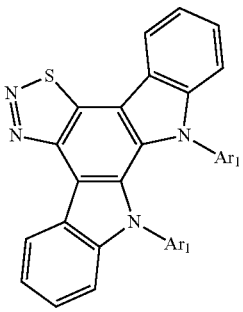
C-166
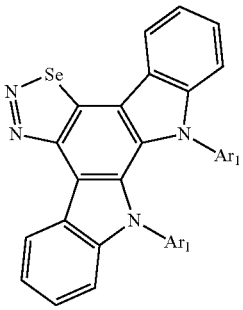
C-167
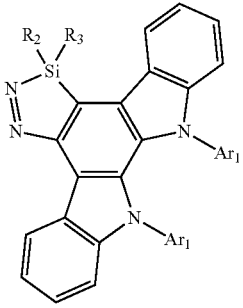
C-168
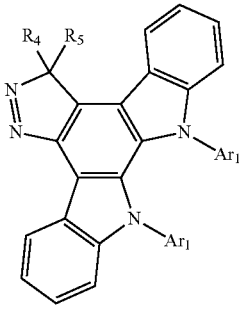

C-169 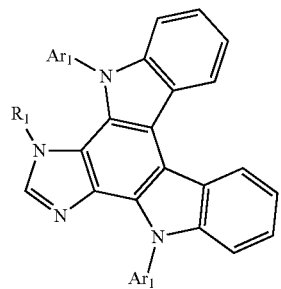
C-170 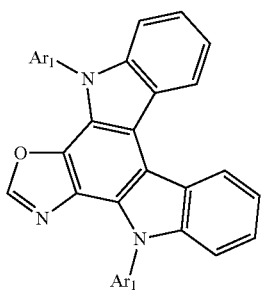
C-171 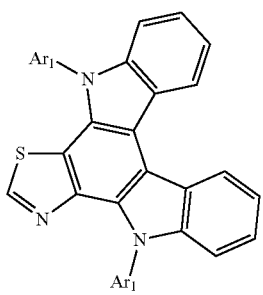
C-172 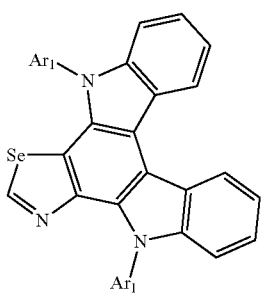
C-173 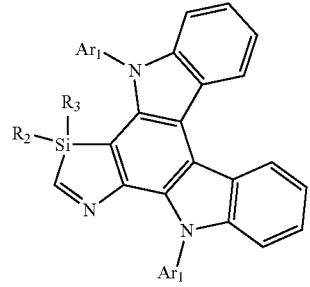
C-174 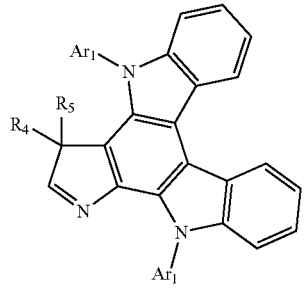
C-175 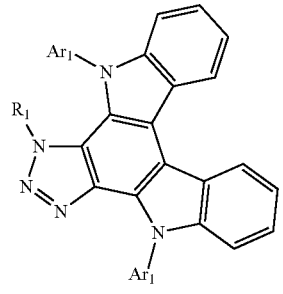
C-176 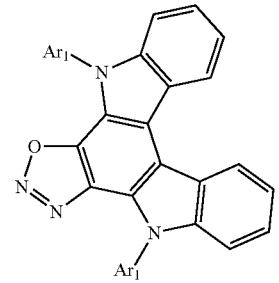
C-177 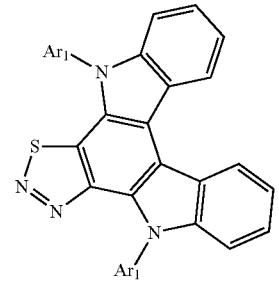
C-178 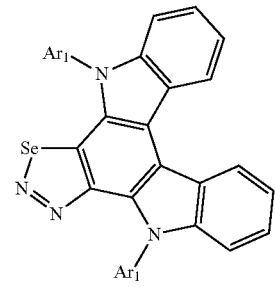

C-179 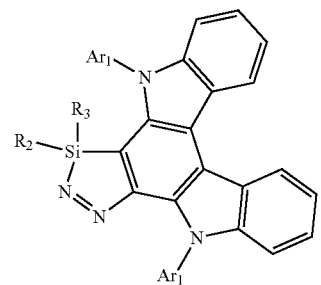
C-180 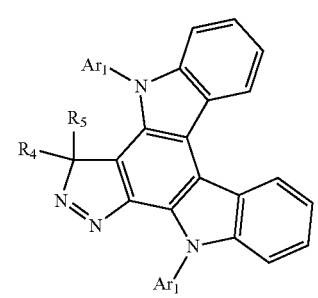
C-181 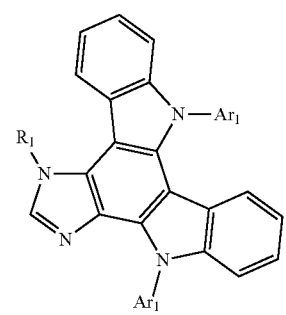
C-182 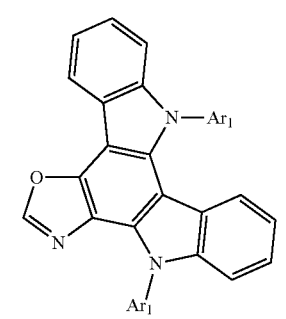
C-183 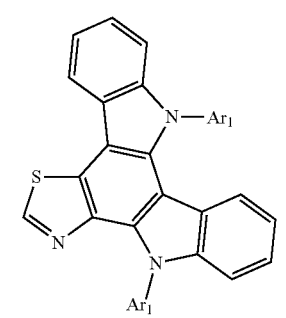
C-184 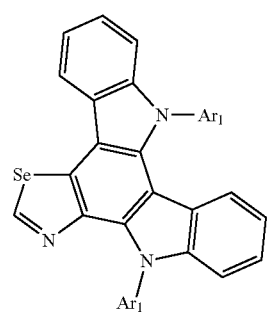
C-185 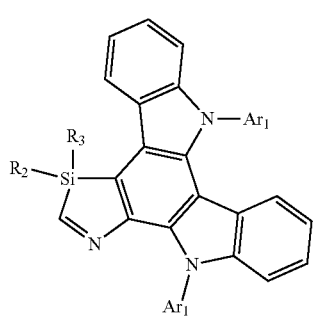
C-186 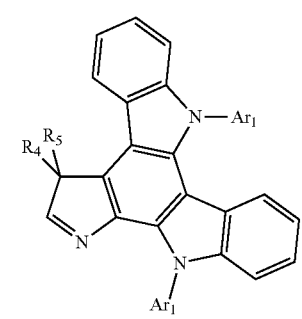
C-187 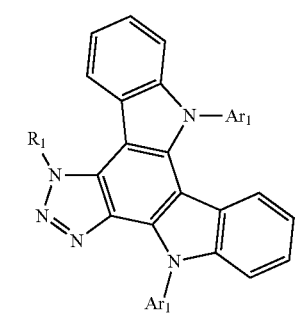
C-188 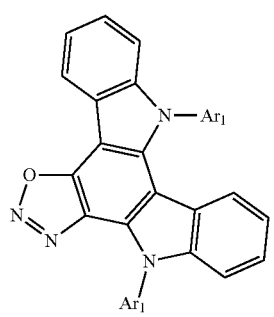

-continued

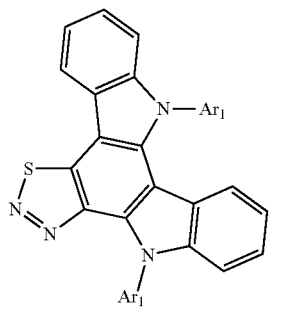
C-189

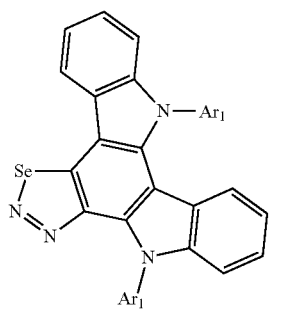
C-190

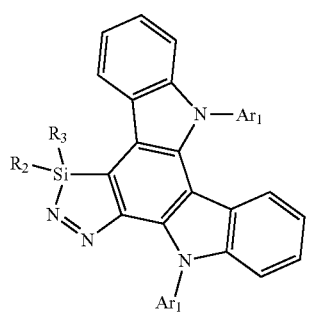
C-191

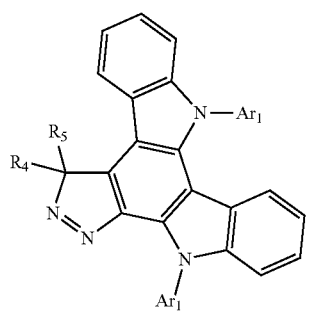
C-192

The term "unsubstituted alkyl" used in the present invention means a monovalent functional group obtained by removing a hydrogen atom from a linear or branched saturated hydrocarbon having 1 to 40 carbon atoms, and non-limiting examples thereof include methyl, ethyl, propyl, isobutyl, sec-butyl, pentyl, iso-amyl, hexyl, and the like.

Further, the term "unsubstituted cycloalkyl" in the present invention means a monovalent functional group obtained by removing a hydrogen atom from a monocyclic or polycyclic non-aromatic hydrocarbon (saturated cyclic hydrocarbon) having 3 to 40 carbon atoms. Examples of the cycloalkyl include cyclopropyl, cyclopentyl, cyclohexyl, norbornyl, adamantine, and the like, but are not limited thereto.

In addition, the term "unsubstituted heterocycloalkyl" in the present invention means a monovalent functional group obtained by removing a hydrogen atom from a non-aromatic hydrocarbon (saturated cyclic hydrocarbon) having 3 to 40 nuclear atoms, and in this case, one or more carbons in the ring, preferably one to three carbons are substituted with a heteroatom such as N, O, or S. Non-limiting examples thereof include morpholine, piperazine, and the like.

Furthermore, the term "unsubstituted aryl" in the present invention means a monovalent functional group obtained by removing a hydrogen atom from an aromatic hydrocarbon having 6 to 60 carbon atoms in which a single ring or two or more rings are combined. In this case, two or more rings may be simply pendant to each other or pendant to each other in a fused form. Non-limiting examples thereof include phenyl, biphenyl, terphenyl, naphthyl, phenanthryl, anthryl, and the like.

Further, the term "unsubstituted heteroaryl" in the present invention means a monovalent functional group obtained by removing a hydrogen atom from a monoheterocyclic or polyheterocyclic aromatic hydrocarbon having 5 to 60 nuclear atoms, in which one or more carbons in the ring, preferably one to three carbons are substituted with a heteroatom such nitrogen (N), oxygen (O), sulfur (S), or selenium (Se). In this case, for the heteroaryl, two or more rings may be simply pendant to each other or pendant to each other in a fused form, and furthermore, a form that is fused with an aryl group is also included. It is interpreted that non-limiting examples of the heteroaryl include: a six-membered monocyclic ring such as pyridyl, pyrazinyl, pyrimidinyl, pyridazinyl, and triazinyl; and a polycyclic ring such as phenoxathienyl, indolizinyl, indolyl, purinyl, quinolyl, benzothiazole, and carbazolyl, and also include 2-furanyl, N-imidazolyl, 2-isoxazolyl, 2-pyridinyl, 2-pyrimidinyl, and the like.

In addition, the term "unsubstituted alkyloxy" in the present invention means a monovalent functional group represented by RO—, and in this case, it is interpreted that R is an alkyl having 1 to 40 carbon atoms, and includes a linear, branched, or cyclic structure. Examples of the alkyloxy include methoxy, ethoxy, n-propoxy, 1-propoxy, t-butoxy, n-butoxy, pentoxy, and the like, and are not limited thereto.

Furthermore, the term "unsubstituted aryloxy" in the present invention means a monovalent functional group represented by R'O—, and in this case, R' is an aryl having 6 to 60 carbon atoms. Non-limiting examples of the aryloxy include phenyloxy, naphthyloxy, diphenyloxy, and the like.

Further, the term "unsubstituted arylamine" in the present invention means an amine substituted with an aryl having 6 to 60 carbon atoms.

The term "fused ring" means a fused aliphatic ring, a fused aromatic ring, a fused heteroaliphatic ring, a fused heteroaromatic ring, or a combined form thereof.

The compound represented by Formula 1 according to the present invention may be synthesized by a general synthesis method [see Chem. Rev., 60:313 (1960); J. Chem. SOC. 4482 (1955); Chem. Rev. 95: 2457 (1995), and the like]. The detailed synthesis process of the compound of the present invention will be specifically described in Synthesis Examples to be described below.

Meanwhile, the present invention provides an organic electroluminescent device including the above-described compound represented by Formula 1 (preferably, the compound represented by any one of Formulae 3 to 12).

Specifically, the organic electroluminescent device according to the present invention includes an anode, a cathode, and one or more organic material layers interposed between the anode and the cathode, in which at least one of the one or more organic material layers includes one or more of the compounds represented by Formula 1 (preferably the compound represented by any one of Formulae 3 to 12).

Examples of the one or more organic material layers include a hole injection layer, a hole transporting layer, a light-emitting layer, an electron transporting layer, an electron injection layer, and the like, and among them, at least one organic material layer may include the compound represented by Formula 1. Preferably, the one or more organic material layers including the compound of Formula 1 may be a hole transporting layer, a hole injection layer, or a light-emitting layer, and more preferably, a light-emitting layer.

As an example, the light-emitting layer of the organic electroluminescent device according to the present invention includes a host material and/or a dopant material. In this case, the compound represented by Formula 1 (preferably, the compound represented by any one of Formulae 3 to 8) may be used as a phosphorescent host material of the light-emitting layer. In this case, the light-emitting efficiency, brightness, power efficiency, thermal stability, and lifespan of the device may be enhanced due to the compound.

The structure of the organic electroluminescent device according to the present invention is not particularly limited, and non-limiting examples thereof may be a structure in which a substrate, an anode, a hole injection layer, a hole transporting layer, a light-emitting layer, an electron transporting layer, and a cathode are sequentially laminated. In this case, one or more of the hole injection layer, the hole transporting layer, and the light-emitting layer may include one or more of the compounds represented by Formula 1. Further, preferably, the compound of the present invention has a wide band-gap and excellent thermal stability, and thus may be used as a phosphorescent host material for a light-emitting layer. Selectively, an electron injection layer may be additionally laminated on an electron transporting layer. In addition, the organic electroluminescent device according to the present invention may be composed of not only a structure in which an anode, one or more organic material layers and a cathode are sequentially laminated, but also a structure in which an insulation layer or an adhesive layer may be inserted at the interface of the electrode and the organic material layer.

The organic electroluminescent device according to the present invention may be manufactured by forming other organic material layers and electrodes using the material and method known in the art, except that one or more (for example, the light-emitting layer, the hole transporting layer and/or the electron transporting layer) of the organic material layers are formed so as to include the compound represented by Formula 1.

The organic material layer may be formed by a vacuum deposition method or a solution coating method. Examples of the solution coating method include spin coating, dip coating, doctor blading, inkjet printing or heat transferring method and the like, but are not limited thereto.

As a substrate which may be used in the present invention, a silicon wafer, quartz or a glass plate, a metal plate, a plastic film or sheet or the like may be used, but the substrate is not limited thereto.

Further, examples of an anode material include: a metal such as vanadium, chromium, copper, zinc and gold, or an alloy thereof; a metal oxide such as zinc oxide, indium oxide, indium tin oxide (ITO) and indium zinc oxide (IZO); a combination of a metal and an oxide, such as ZnO:Al or SnO$_2$:Sb; a conductive polymer such as polythiophene, poly(3-methylthiophene), poly[3,4-(ethylene-1,2-dioxy) thiophene] (PEDT), polypyrrole and polyaniline; or carbon black and the like, but are not limited thereto.

In addition, examples of a cathode material include: a metal such as magnesium, calcium, sodium, potassium, titanium, indium, yttrium, lithium, gadolinium, aluminum, silver, tin or lead or an alloy thereof; a multilayer structured material such as LiF/Al or LiO$_2$/Al, and the like, but are not limited thereto.

Furthermore, the hole injection layer, the hole transporting layer, the electron injection layer, and the electron transporting layer are not particularly limited, and a typical material known in the art may be used.

Hereinafter, the present invention will be described in detail through Examples. However, the following Examples are to exemplify the present invention, and the present invention is not limited by the following Examples.

PREPARATION EXAMPLE 1

Synthesis of Compounds Core1A and Core1B

<Step 1> Synthesis of 5-(2-nitrophenyl)-1H-benzo[d]imidazole

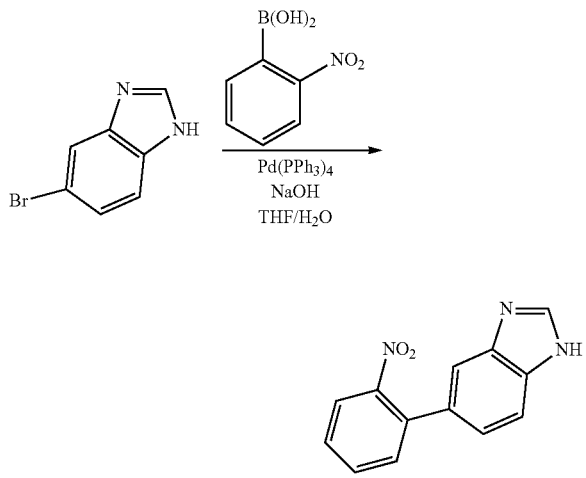

6.5 g (32.98 mmol) of 5-bromo-1H-benzo[d]imidazole, 6.6 g (39.58 mmol) of 2-nitrophenylboronic acid, 3.9 g (98.96 mmol) of NaOH, and 150 ml/50 ml of THF/H$_2$O were mixed under nitrogen flow, and the mixture was stirred. 1.14 g (0.98 mmol) of Pd(PPh$_3$)$_4$ was added thereto at 40° C., and the resulting mixture was stirred under reflux at 80° C. for 12 hours. After the reaction was completed, an organic layer obtained by performing extraction with dichloromethane was dried over MgSO$_4$, and then filtered under reduced pressure. The filtered organic layer was distilled under reduced pressure, and then 5.2 g (yield: 66%) of a compound 5-(2-nitrophenyl)-1H-benzo[d]imidazole was obtained by using column chromatography.

$^1$H-NMR: δ 7.68 (m, 2H), 8.02 (m, 5H), 8.14 (s, 1H), 8.45 (s, 1H)

<Step 2> Synthesis of Compounds Core1A and Core1B

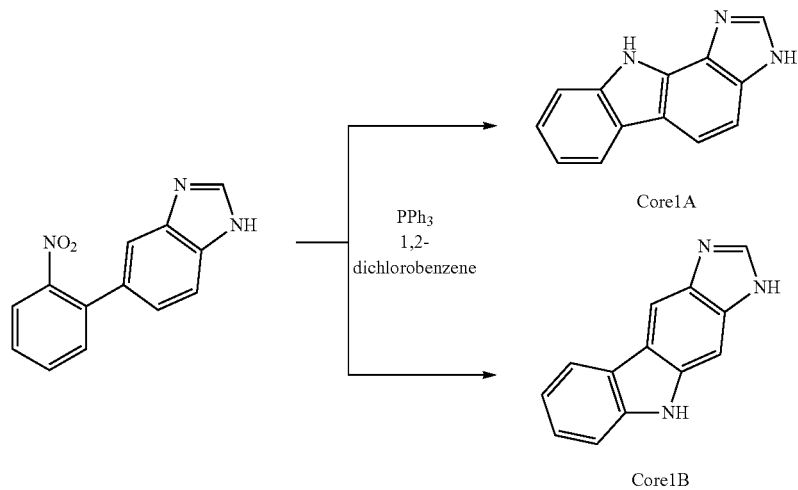 [SMILES: c1ccc2c(c1)[nH]c1c2ccc2[nH]cnc21 ; O=[N+]([O-])c1ccccc1-c1ccc2[nH]cnc2c1 ; c1ccc2c(c1)[nH]c1cc3[nH]cnc3cc12]

5.2 g (21.73 mmol) of 5-(2-nitrophenyl)-1H-benzo[d]imidazole obtained in <Step 1> of Preparation Example 1, 11.4 g (43.47 mmol) of triphenylphosphine, and 100 ml of 1,2-dichlorobenzene were mixed under nitrogen flow, and then the mixture was stirred for 12 hours. After the reaction was completed, 1,2-dichlorobenzene was removed by distillation, and an organic layer was extracted with dichloromethane. The extracted organic layer was dried over $MgSO_4$, and then filtered under reduced pressure. The filtered organic layer was distilled under reduced pressure, and then 1.8 g (yield: 40%) of Compound Core1A and 1.3 g (yield: 28%) of Compound Core1B were obtained by using column chromatography.

$^1$H-NMR for Compound Core1A: δ 7.31 (t, 1H), 7.55 (m, 3H), 7.87 (d, 1H), 8.15 (m, 2H), 8.43 (s, 1H), 10.23 (s, 1H)

$^1$H-NMR for Compound Core2B: δ 7.29 (t, 1H), 7.52 (t, 1H), 7.68 (m, 3H), 8.13 (m, 2H), 8.47 (s, 1H), 10.18 (s, 1H)

PREPARATION EXAMPLE 2

Synthesis of Compounds Core2A and Core2B

<Step 1> Synthesis of 5-(2-nitrophenyl)-1H-benzo[d][1,2,3]triazole

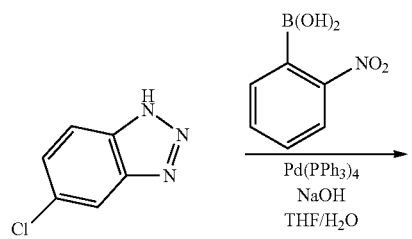

-continued

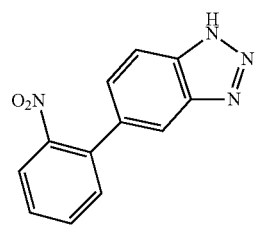

6.3 g (yield: 51%) of 5-(2-nitrophenyl)-1H-benzo[d][1,2,3]triazole was obtained by performing the same procedure as in <Step 1> of Preparation Example 1, except that 7.9 g of 5-chloro-1H-benzo[d][1,2,3]triazole was used instead of 5-bromo-1H-benzo[d]imidazole used in <Step 1> of Preparation Example 1.

$^1$H-NMR: δ 7.68 (m, 2H), 7.92 (t, 1H), 8.03 (m, 3H), 8.20 (s, 1H)

<Step 2> Synthesis of Compounds Core2A and Core2B

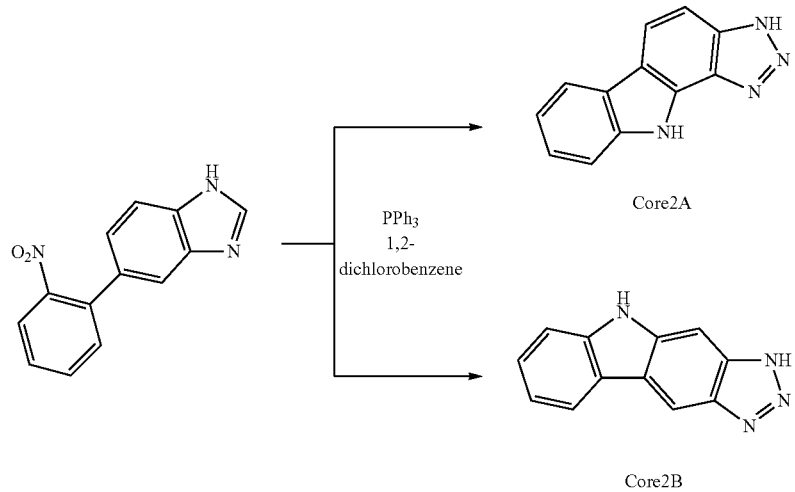 [SMILES: c1ccc2c(c1)[nH]c1c2ccc2[nH]nnc21 ; O=[N+]([O-])c1ccccc1-c1ccc2[nH]cnc2c1 ; c1ccc2c(c1)[nH]c1cc3[nH]nnc3cc12]

2.3 g (yield: 42%) of Compound Core2A and 0.8 g (yield: 14%) of Compound Core2B were obtained by performing the same procedure as in <Step 2> of Preparation Example 1, except that 6.3 g of 5-(2-nitrophenyl)-1H-benzo[d][1,2,3]triazole obtained in <Step 1> of Preparation Example 2 was used instead of 5-(2-nitrophenyl)-1H-benzo[d]imidazole used in <Step 2> of Preparation Example 1.

$^1$H-NMR for Compound Core2A: δ 7.28 (t, 1H), 7.48 (m, 2H), 7.65 (d, 1H), 7.98 (d, 1H), 8.13 (d, 1H), 10.33 (s, 1H)

$^1$H-NMR for Compound Core2B: δ 7.30 (t, 1H), 7.52 (t, 1H), 7.65 (d, 1H), 8.02 (m, 2H), 8.15 (d, 1H), 10.35 (s, 1H)

PREPARATION EXAMPLE 3

Synthesis of Compounds Core3A and Core3B

<Step 1> Synthesis of 5-(2-nitrophenyl)benzo[d]oxazole

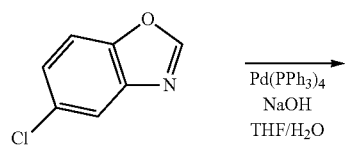

-continued

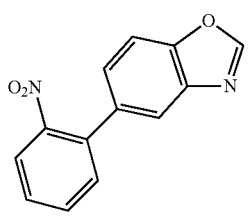

4.1 g (yield: 46%) of 5-(2-nitrophenyl)benzo[d]oxazole was obtained by performing the same procedure as in <Step 1> of Preparation Example 1, except that 5.7 g of 5-chlorobenzo[d]oxazole was used instead of 5-bromo-1H-benzo[d]imidazole used in <Step 1> of Preparation Example 1.

$^1$H-NMR: δ 7.65 (t, 1H), 7.88 (m, 4H), 8.12 (m, 3H)

<Step 2> Synthesis of Compounds Core3A and Core3B

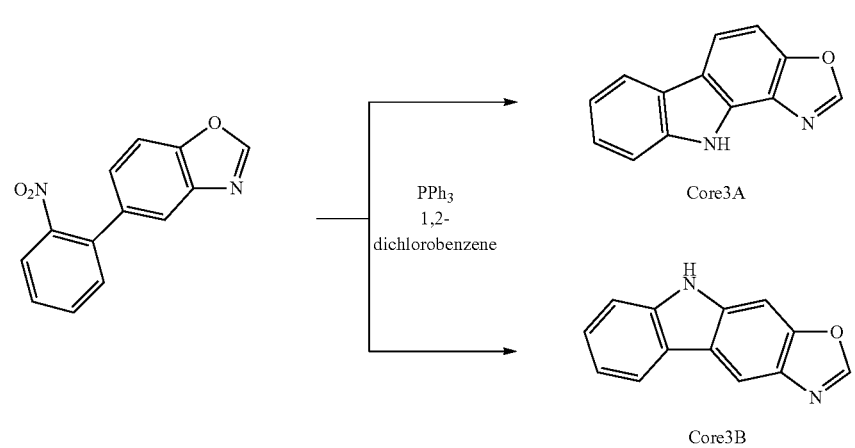 [SMILES: O=[N+]([O-])c1ccccc1-c1ccc2ocnc2c1 ; c1ccc2c(c1)[nH]c1cc3ocnc3cc12 ; c1ccc2c(c1)[nH]c1c2ccc2ocnc21]

1.6 g (yield: 45%) of Compound Core3A and 0.4 g (yield: 14%) of Compound Core3B were obtained by performing the same procedure as in <Step 2> of Preparation Example 1, except that 4.1 g of 5-(2-nitrophenyl)benzo[d]oxazole obtained in <Step 1> of Preparation Example 3 was used instead of 5-(2-nitrophenyl)-1H-benzo[d]imidazole used in <Step 2> of Preparation Example 1.

¹H-NMR for Compound Core3A: δ 7.02 (d, 1H), 7.28 (t, 1H), 7.53 (t, 1H), 7.72 (d, 1H), 7.98 (s, 1H), 8.15 (m, 2H), 10.38 (s, 1H)

4.7 g (yield: 62%) of 6-(2-nitrophenyl)benzo[d]thiazole was obtained by performing the same procedure as in <Step 1> of Preparation Example 1, except that 6.3 g of 6-bromobenzo[d]thiazole was used instead of 5-bromo-1H-benzo[d]imidazole used in <Step 1> of Preparation Example 1.

¹H-NMR: δ 7.72 (m, 2H), 7.92 (m, 3H), 8.35 (s, 1H), 9.28 (s, 1H)

<Step 2> Synthesis of Compounds Core4A and Core4B

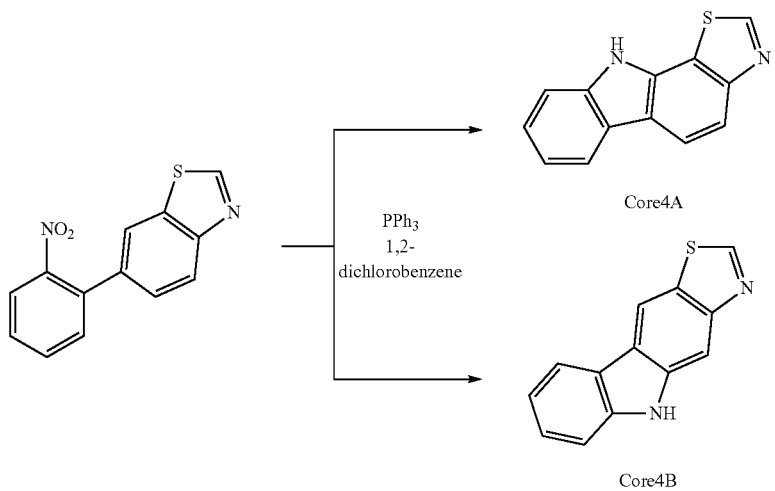 [SMILES: c1ccc2c(c1)[nH]c1c2ccc2ncsc21 ; O=[N+]([O-])c1ccccc1-c1ccc2ncsc2c1 ; c1ccc2c(c1)[nH]c1cc3ncsc3cc12]

¹H-NMR for Compound Core3B: δ 7.30 (t, 1H), 7.42 (s, 1H), 7.58 (m, 3H), 7.98 (s, 1H), 8.18 (d, 1H), 10.34 (s, 1H)

PREPARATION EXAMPLE 4

Synthesis of Compounds Core4A and Core4B

<Step 1> Synthesis of 6-(2-nitrophenyl)benzo[d]thiazole

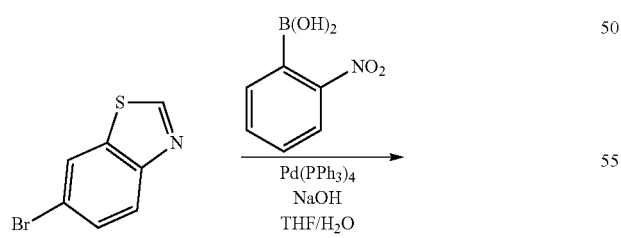

2.2 g (yield: 53%) of Compound Core4A and 0.9 g (yield: 21%) of Compound Core4B were obtained by performing the same procedure as in <Step 2> of Preparation Example 1, except that 4.7 g of 6-(2-nitrophenyl)benzo[d]thiazole obtained in <Step 1> of Preparation Example 4 was used instead of 5-(2-nitrophenyl)-1H-benzo[d]imidazole used in <Step 2> of Preparation Example 1.

¹H-NMR for Compound Core4A: δ 7.25 (t, 1H), 7.55 (m, 3H), 7.78 (d, 1H), 8.15 (d, 1H), 9.26 (s, 1H), 10.27 (s, 1H)

¹H-NMR for Compound Core4B: δ 7.26 (t, 1H), 7.52 (t, 1H), 7.66 (d, 1H), 8.10 (m, 2H), 8.25 (s, 1H), 9.27 (s, 1H), 10.42 (s, 1H)

PREPARATION EXAMPLE 5

Synthesis of Compounds Core5A and Core5B

<Step 1> Synthesis of 5-(2-nitrophenyl)-1H-benzo[d]imidazole

A compound 5-(2-nitrophenyl)-1H-benzo[d]imidazole was obtained by performing the same procedure as in <Step 1> of Preparation Example 1.

<Step 2> Synthesis of Core5 -1 and Core5 -2

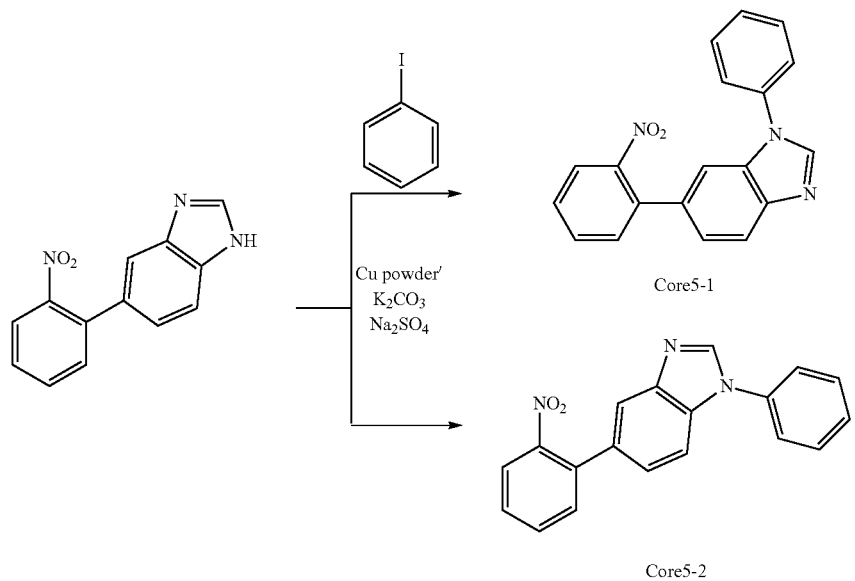 [SMILES: O=[N+]([O-])c1ccccc1-c1ccc2[nH]cnc2c1 ; Ic1ccccc1 ; O=[N+]([O-])c1ccccc1-c1ccc2c(c1)ncn2-c1ccccc1 ; O=[N+]([O-])c1ccccc1-c1ccc2ncn(-c3ccccc3)c2c1]

7.5 g (31.35 mmol) of 5-(2-nitrophenyl)-1H-benzo[d]imidazole obtained in <Step 1> of Preparation Example 5, 9.6 g (47 mmol) of iodobenzene, 0.2 g (3.135 mmol) of Cu powder, 8.9 g (62.7 mmol) of $Na_2SO_4$, and 4.3 g (31.35 mmol) of $K_2CO_3$ were added to 100 ml of nitrobenzene under nitrogen flow, and the mixture was stirred under reflux for 24 hours. After the reaction was completed, nitrobenzene was removed by distillation, and an organic layer obtained by performing extraction with dichloromethane was dried over $MgSO_4$, and then filtered under reduced pressure. The filtered organic layer was distilled under reduced pressure, and then 4.2 g (yield: 42%) of Compound Core5-1 and 3.6 g (yield: 36%) of Compound Core5-2 were obtained by using column chromatography.

$^1$H-NMR for Compound Core5-1: δ 7.55 (m, 6H), 7.98 (m, 2H), 8.05 (m, 4H), 8.32 (d, 1H)

$^1$H-NMR for Compound Core5-2: δ 7.58 (m, 7H), 7.92 (m, 2H), 8.07 (m, 4H)

<Step 3> Synthesis of Compounds Core5A and Core5B

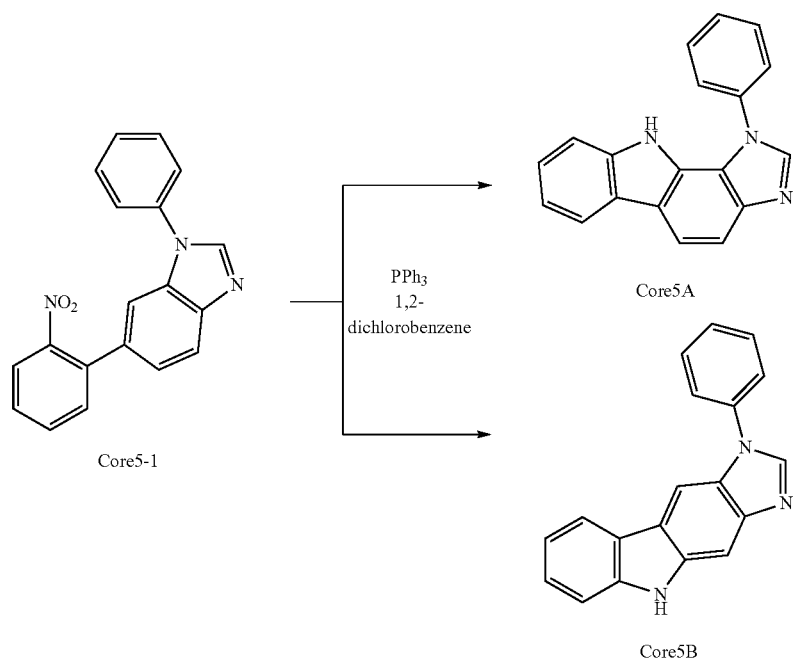 [SMILES: O=[N+]([O-])c1ccccc1-c1ccc2ncn(-c3ccccc3)c2c1 ; c1ccc(-n2cnc3ccc4c5ccccc5[nH]c4c32)cc1 ; c1ccc(-n2cnc3cc4[nH]c5ccccc5c4cc32)cc1]

1.6 g (yield: 42%) of Compound Core5A and 1.1 g (yield: 29%) of Compound Core5B were obtained by performing the same procedure as in <Step 2> of Preparation Example 1, except that 4.2 g of Compound Core5-1 obtained in <Step 2> of Preparation Example 5 was used instead of 5-(2-nitrophenyl)-1H-benzo[d]imidazole used in <Step 2> of Preparation Example 1.

$^1$H-NMR for Compound Core5A: δ 7.27 (t, 1H), 7.58 (m, 8H), 7.83 (d, 1H), 8.12 (m, 2H), 10.32 (s, 1H)

$^1$H-NMR for Compound Core5B: δ 7.28 (t, 1H), 7.62 (m, 9H), 8.08 (m, 2H), 10.35 (s, 1H)

PREPARATION EXAMPLE 6

Synthesis of Compounds Core6A and Core6B

<Step 1> Synthesis of 5-(2-nitrophenyl)-1H-benzo[d][1,2,3]triazole

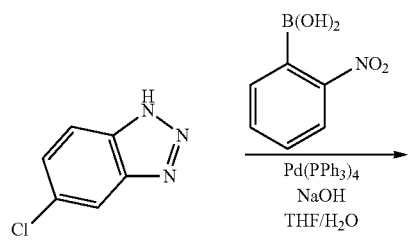

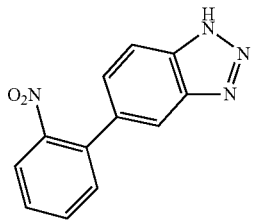

6.8 g (yield: 68%) of 5-(2-nitrophenyl)-1H-benzo[d][1,2,3]triazole was obtained by performing the same procedure as in <Step 1> of Preparation Example 1, except that 6.5 g of 5-chloro-1H-benzo[d][1,2,3]triazole was used instead of 5-bromo-1H-benzo[d]imidazole used in <Step 1> of Preparation Example 1.

<Step 2> Synthesis of Compounds Core6-1 and Core6-2

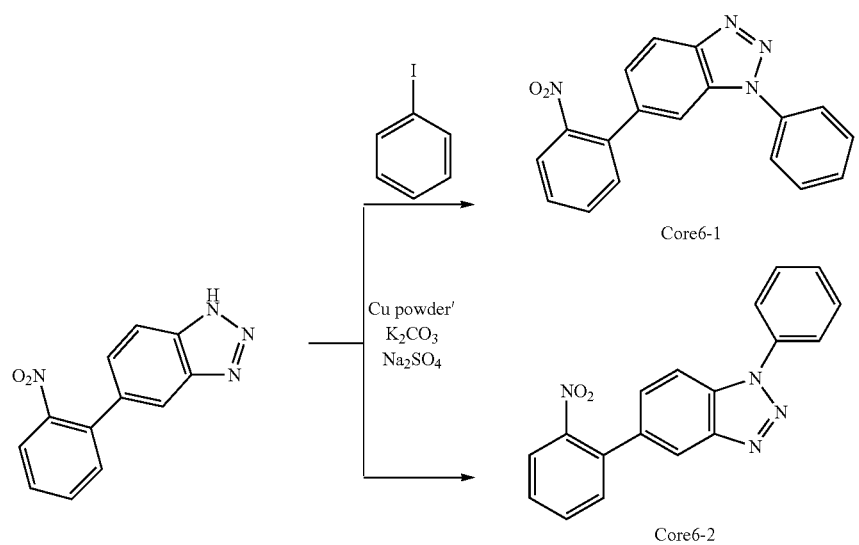 [SMILES: Ic1ccccc1 ; O=[N+]([O-])c1ccccc1-c1ccc2nnn(-c3ccccc3)c2c1 ; O=[N+]([O-])c1ccccc1-c1ccc2[nH]nnc2c1 ; O=[N+]([O-])c1ccccc1-c1ccc2c(c1)nnn2-c1ccccc1]

4.2 g (yield: 47%) of Compound Core6-1 and 2.8 g (yield: 31%) of Compound Core6-2 were obtained by performing the same procedure as in <Step 2> of Preparation Example 5, except that 6.8 g of 5-chloro-1H-benzo[d][1,2,3]triazole obtained in <Step 1> of Preparation Example 6 was used instead of 5-(2-nitrophenyl)-1H-benzo[d]imidazole used in <Step 1> of Preparation Example 5.

¹H-NMR for Compound Core6-1: δ 7.43 (t, 1H), 7.60 (m, 6H), 7.88 (t, 1H), 8.00 (m, 3H), 8.18 (s, 1H)

¹H-NMR for Compound Core6-2: δ 7.47 (t, 1H), 7.64 (m, 6H), 7.92 (t, 1H), 8.03 (m, 3H), 8.22 (s, 1H)

<Step 3> Synthesis of Compounds Core6A and Core6B

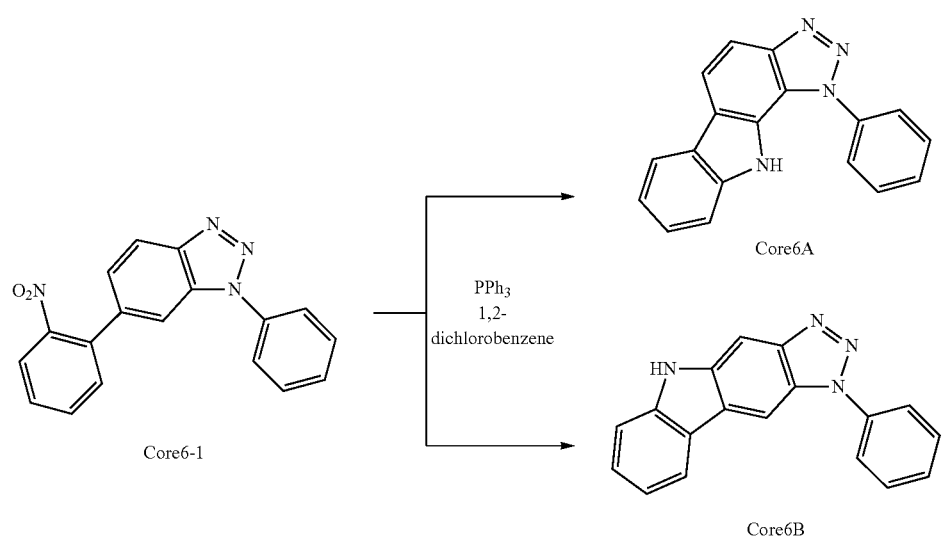 [SMILES: O=[N+]([O-])c1ccccc1-c1ccc2nnn(-c3ccccc3)c2c1 ; c1ccc(-n2nnc3cc4[nH]c5ccccc5c4cc32)cc1 ; c1ccc(-n2nnc3ccc4c5ccccc5[nH]c4c32)cc1]

1.5 g (yield: 39%) of Compound Core6-1 and 0.8 g (yield: 21%) of Compound Core6-2 were obtained by performing the same procedure as in <Step 2> of Preparation Example 1, except that 4.2 g of Compound Core6-1 obtained in <Step 2> of Preparation Example 6 was used instead of 5-(2-nitrophenyl)-1H-benzo[d]imidazole used in <Step 2> of Preparation Example 1.

¹H-NMR for Compound Core6A: δ 7.32 (t, 1H), 7.48 (m, 3H), 7.65 (m, 5H), 7.98 (d, 1H), 8.13 (d, 1H), 10.45 (s, 1H)

¹H-NMR for Compound Core6B: δ 7.29 (t, 1H), 7.62 (m, 7H), 8.01 (m, 2H), 8.16 (d, 1H), 10.42 (s, 1H)

PREPARATION EXAMPLE 7

Synthesis of Compounds Core7A and Core7B

<Step 1> Synthesis of 5-(2-nitrophenyl)-2-phenyl-benzo[d]oxazole

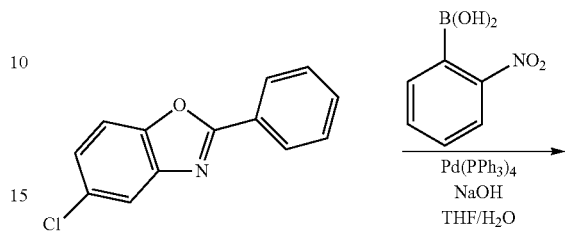

-continued

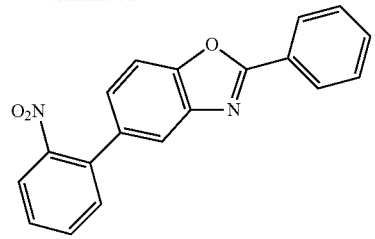

4.8 g (yield: 54%) of 5-(2-nitrophenyl)-2-phenylbenzo[d]oxazole was obtained by performing the same procedure as in <Step 1> of Preparation Example 1, except that 6.45 g of 5-chloro-2-phenylbenzo[d]oxazole was used instead of 5-bromo-1H-benzo[d]imidazole used in <Step 1> of Preparation Example 1.

¹H-NMR: δ 7.34 (m, 2H), 7.66 (m, 2H), 7.95 (m, 4H), 8.18 (d, 1H), 9.50 (s, 1H)

\<Step 2\> Synthesis of Compounds Core7A and Core7B

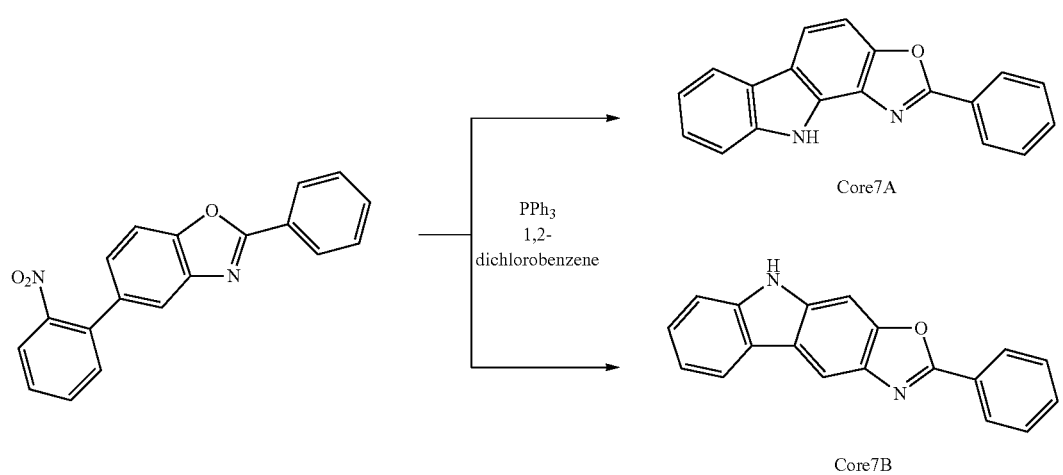 [SMILES: c1ccc(-c2nc3c(ccc4c5ccccc5[nH]c43)o2)cc1 ; O=[N+]([O-])c1ccccc1-c1ccc2oc(-c3ccccc3)nc2c1 ; c1ccc(-c2nc3cc4c(cc3o2)[nH]c2ccccc24)cc1]

1.9 g (yield: 44%) of Compound Core7A and 0.7 g (yield: 16%) of Compound Core7B were obtained by performing the same procedure as in \<Step 2\> of Preparation Example 1, except that 4.8 g of 5-(2-nitrophenyl)-2-phenylbenzo[d]oxazole obtained in \<Step 1\> of Preparation Example 7 was used instead of 5-(2-nitrophenyl)-1H-benzo[d]imidazole used in Preparation Example 1.

$^1$H-NMR for Compound Core7A: δ 7.02 (d, 1H), 7.33 (t, 1H), 7.51 (m, 4H), 8.08 (m, 4H), 10.44 (s, 1H)

$^1$H-NMR for Compound Core7B: δ 7.28 (t, 1H), 7.55 (m, 7H), 8.05 (m, 3H), 10.42 (s, 1H)

PREPARATION EXAMPLE 8

Synthesis of Compounds Core8A and Core8B

\<Step 1\> Synthesis of 6-(2-nitrophenyl)-2-phenyl-benzo[d]thiazole

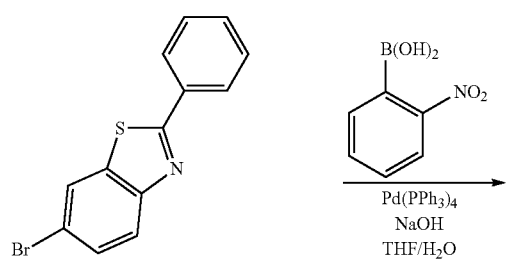

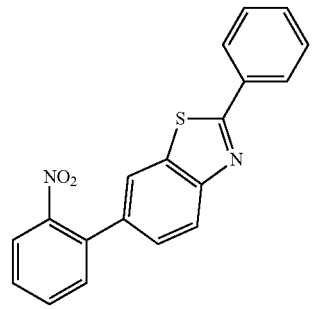

4.2 g (yield: 51%) of 6-(2-nitrophenyl)-2-phenylbenzo[d]thiazole was obtained by performing the same procedure as in \<Step 1\> of Preparation Example 1, except that 7.2 g of 6-bromo-2-phenylbenzo[d]thiazole was used instead of 5-bromo-1H-benzo[d]imidazole used in \<Step 1\> of Preparation Example 1.

$^1$H-NMR: δ 7.45 (m, 3H), 7.68 (t, 1H), 7.78 (m, 2H), 7.93 (t, 1H), 8.03 (m, 4H), 8.36 (s, 1H)

<Step 2> Synthesis of Compounds Core8A and Core8B

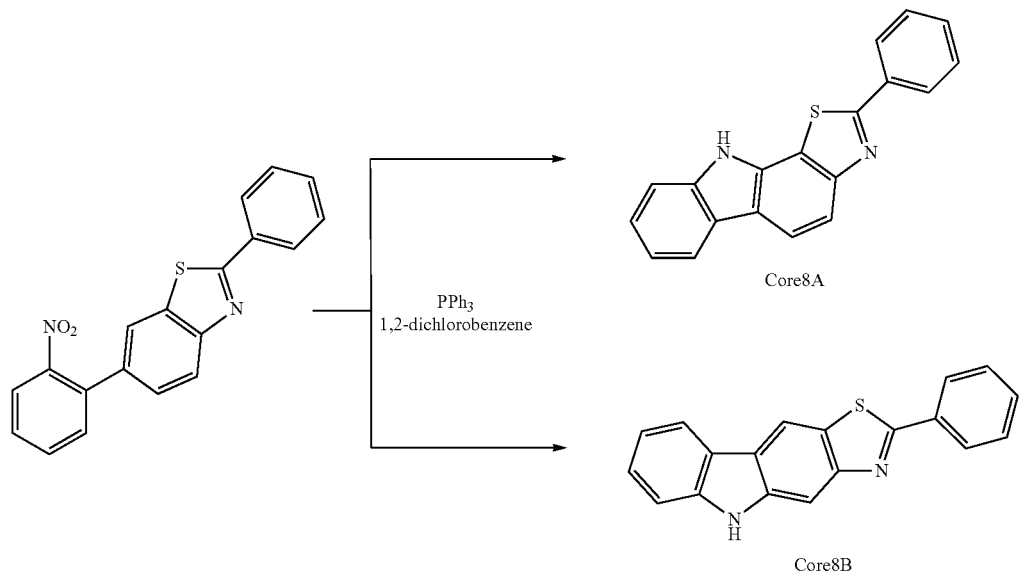 [SMILES: O=[N+]([O-])c1ccccc1-c1ccc2nc(-c3ccccc3)sc2c1 ; c1ccc(-c2nc3cc4[nH]c5ccccc5c4cc3s2)cc1 ; c1ccc(-c2nc3ccc4c5ccccc5[nH]c4c3s2)cc1]

1.3 g (yield: 39%) of Compound Core8A and 0.8 g (yield: 24%) of Compound Core8B were obtained by performing the same procedure as in <Step 2> of Preparation Example 1, except that 4.2 g of 6-(2-nitrophenyl)-2-phenylbenzo[d]thiazole obtained in <Step 1> of Preparation Example 8 was used instead of 5-(2-nitrophenyl)-1H-benzo[d]imidazole used in <Step 2> of Preparation Example 1.

$^1$H-NMR for Compound Core8A: δ 7.32 (t, 1H), 7.51 (m, 6H), 8.07 (m, 3H), 10.38 (s, 1H)

$^1$H-NMR for Compound Core8B: δ 7.29 (t, 1H), 7.45 (m, 4H), 8.05 (m, 4H), 8.26 (s, 1H), 10.35 (s, 1H)

PREPARATION EXAMPLE 9

Synthesis of Compounds Core9A and Core9B

<Step 1> Synthesis of 5-(2-nitrophenyl)-2-phenyl-1H-benzo[d]imidazole

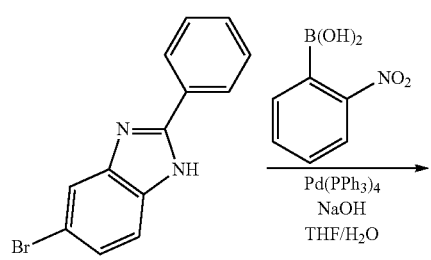

-continued

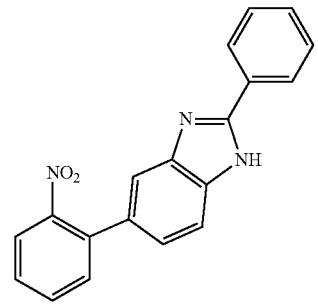

6.2 g (yield: 62%) of 5-(2-nitrophenyl)-2-phenyl-1H-benzo[d]imidazole was obtained by performing the same procedure as in <Step 1> of Preparation Example 1, except that 8.6 of 5-bromo-2-phenyl-1H-benzo[d]imidazole was used instead of 5-bromo-1H-benzo[d]imidazole used in <Step 1> of Preparation Example 1.

$^1$H-NMR: δ 7.51 (m, 3H), 7.67 (m, 2H), 8.03 (m, 5H), 8.32 (m, 2H), 8.45 (s, 1H)

<Step 2> Synthesis of Compounds Core9-1 and Core9-2

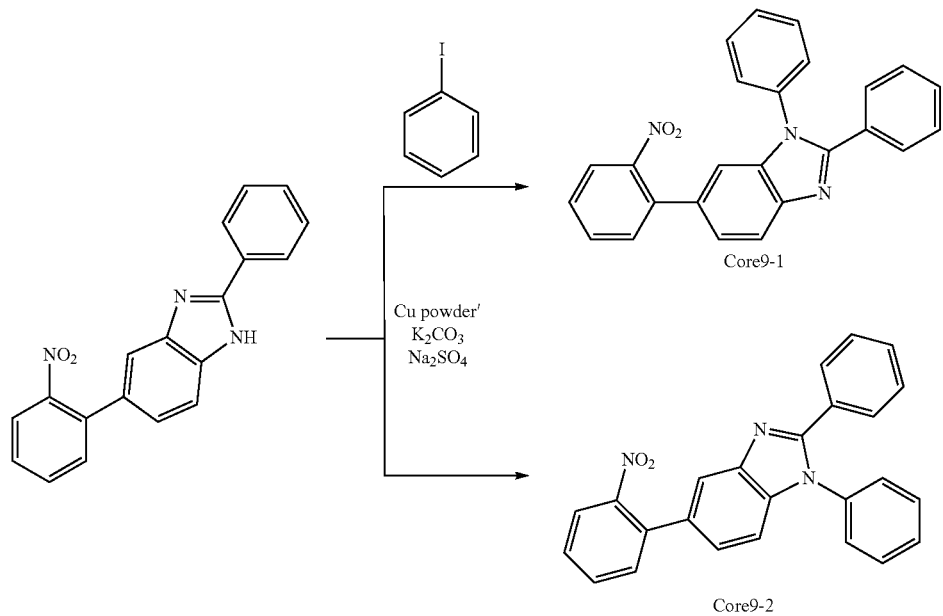 [SMILES: O=[N+]([O-])c1ccccc1-c1ccc2[nH]c(-c3ccccc3)nc2c1 ; Ic1ccccc1 ; O=[N+]([O-])c1ccccc1-c1ccc2c(c1)nc(-c1ccccc1)n2-c1ccccc1 ; O=[N+]([O-])c1ccccc1-c1ccc2nc(-c3ccccc3)n(-c3ccccc3)c2c1]

3.1 g (yield: 40%) of Compound Core9-1 and 2.3 g (yield: 30%) of Compound Core9-2 were obtained by performing the same procedure as in <Step 2> of Preparation Example 5, except that 6.2 g of 5-(2-nitrophenyl)-2-phenyl-1H-benzo[d]imidazole obtained in <Step 1> of Preparation Example 9 was used instead of 5-(2-nitrophenyl)-1H-benzo[d]imidazole used in <Step 2> of Preparation Example 5.

$^1$H-NMR for Compound Core9-1: δ 7.45 (m, 6H), 7.63 (m, 4H), 7.95 (m, 2H), 8.07 (m, 3H), 8.31 (m, 2H)

$^1$H-NMR for Compound Core9-2: δ 7.43 (m, 6H), 7.63 (m, 3H), 7.92 (m, 2H), 8.03 (m, 3H), 8.28 (m, 3H)

<Step 3> Synthesis of Compounds Core9A and Core9B

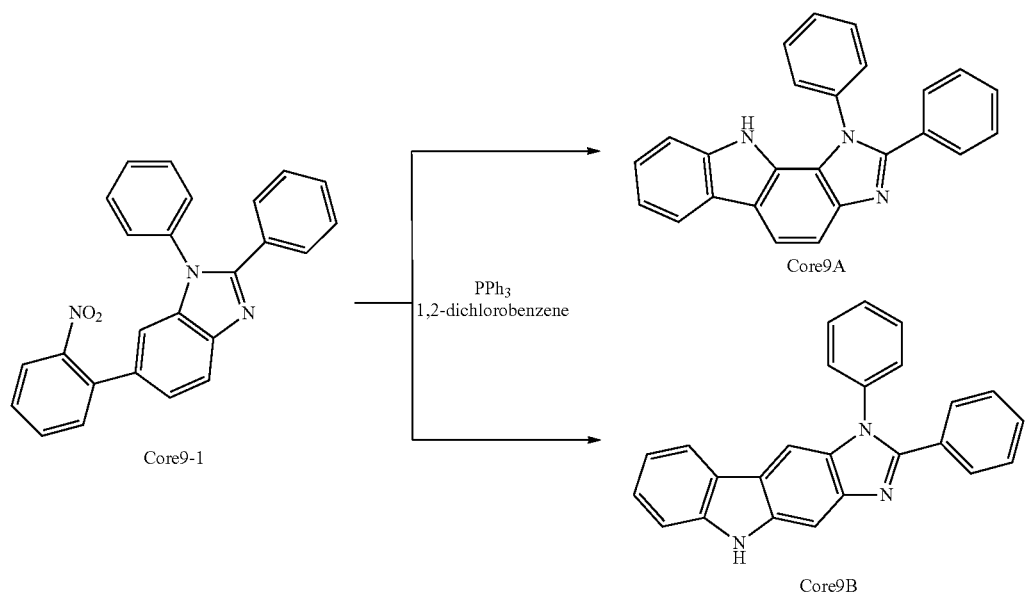 [SMILES: O=[N+]([O-])c1ccccc1-c1ccc2nc(-c3ccccc3)n(-c3ccccc3)c2c1 ; c1ccc(-c2nc3cc4[nH]c5ccccc5c4cc3n2-c2ccccc2)cc1 ; c1ccc(-c2nc3ccc4c5ccccc5[nH]c4c3n2-c2ccccc2)cc1]

1.2 g (yield: 42%) of Compound Core9A and 0.6 g (yield: 21%) of Compound Core9B were obtained by performing the same procedure as in <Step 2> of Preparation Example 1, except that 3.1 g of Compound Core9-1 obtained in <Step 2> of Preparation Example 9 was used instead of 5-(2-nitrophenyl)-1H-benzo[d]imidazole used in <Step 2> of Preparation Example 1.

$^1$H-NMR for Compound Core9A: δ 7.28 (t, 1H), 7.45 (m, 7H), 7.62 (m, 4H), 7.87 (d, 1H), 8.15 (d, 1H), 10.42 (s, 1H)

$^1$H-NMR for Compound Core9B: δ 7.32 (t, 1H), 7.47 (m, 7H), 7.62 (m, 5H), 8.15 (d, 1H), 8.30 (m, 2H), 10.45 (s, 1H)

SYNTHESIS EXAMPLE 1

Synthesis of Compound Inv-1

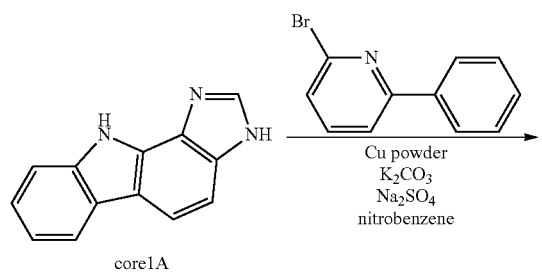

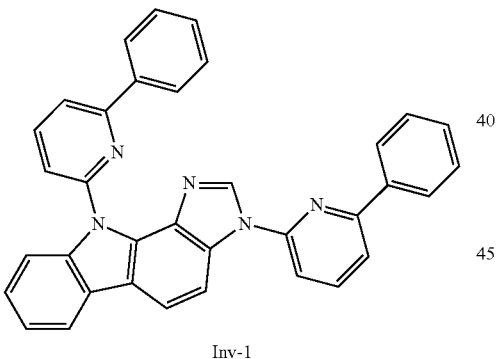

Inv-1

Compound Core1A (2.48 g, 12.00 mmol) synthesized in Preparation Example 1, 2-bromo-6-diphenylpyridine (6.74 g, 28.80 mmol), Cu powder (0.08 g, 1.20 mmol), K$_2$CO$_3$ (1.66 g, 12.00 mmol), Na$_2$SO$_4$ (1.71 g, 12.00 mmol), and nitrobenzene (100 ml) were mixed under nitrogen flow, and the mixture was stirred at 190° C. for 12 hours.

After the reaction was completed, nitrobenzene was removed, the organic layer was separated with methylene chloride, and water was removed from the organic layer by using MgSO$_4$. After the solvent was removed from the organic layer, the residue was purified by column chromatography (Hexane:EA=3:1 (v/v)), thereby obtaining Compound Inv-1 (4.61 g, yield: 75%).

GC-Mass (theoretical value: 513.20 g/mol, measured value: 513 g/mol)

SYNTHESIS EXAMPLE 2

Synthesis of Compound Inv-2

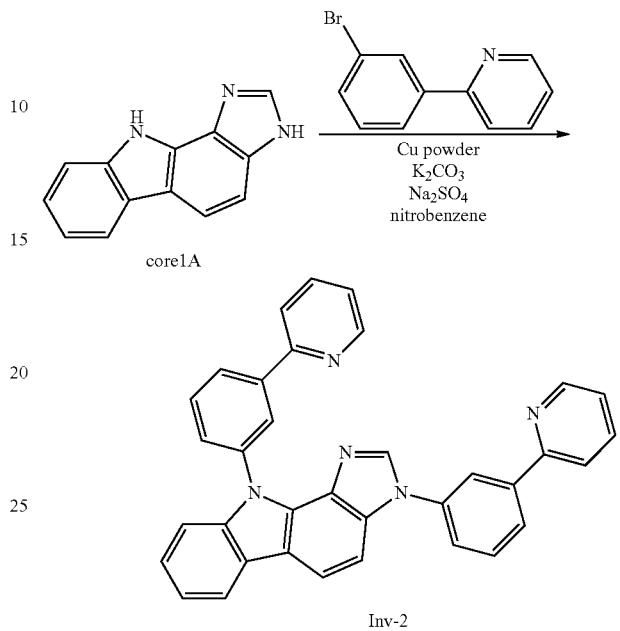

Compound Inv-2 (4.31 g, yield: 70%) was obtained by performing the same method as in Synthesis Example 1, except that 2.48 g of 2-(3-bromophenyl)pyridine was used instead of 2-bromo-6-phenylpyridine used in Synthesis Example 1.

GC-Mass (theoretical value: 513.20 g/mol, measured value: 513 g/mol)

SYNTHESIS EXAMPLE 3

Synthesis of Compound Inv-3

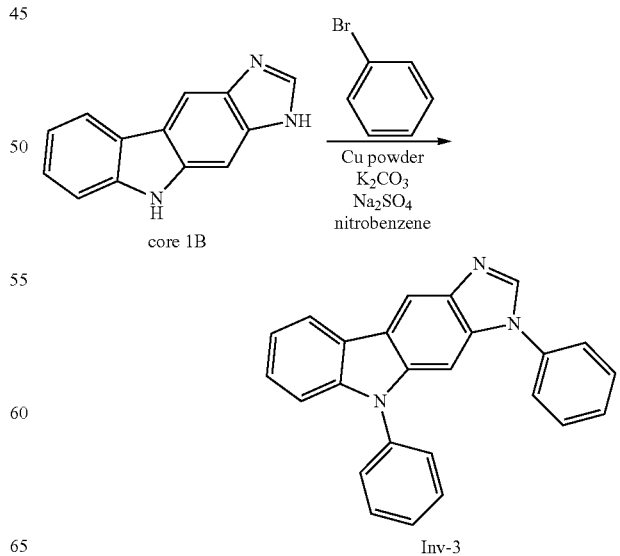

Compound Inv-3 (3.14 g, yield: 73%) was obtained by performing the same method as in Synthesis Example 1, except that 2.48 g of Compound Core1B synthesized in Preparation Example 1 was used instead of Compound Core1A used in Synthesis Example 1, and 2.81 g of bromobenzene was used instead of 2-bromo-6-phenylpyridine.

GC-Mass (theoretical value: 359.42 g/mol, measured value: 359 g/mol)

SYNTHESIS EXAMPLE 4

Synthesis of Compound Inv-4

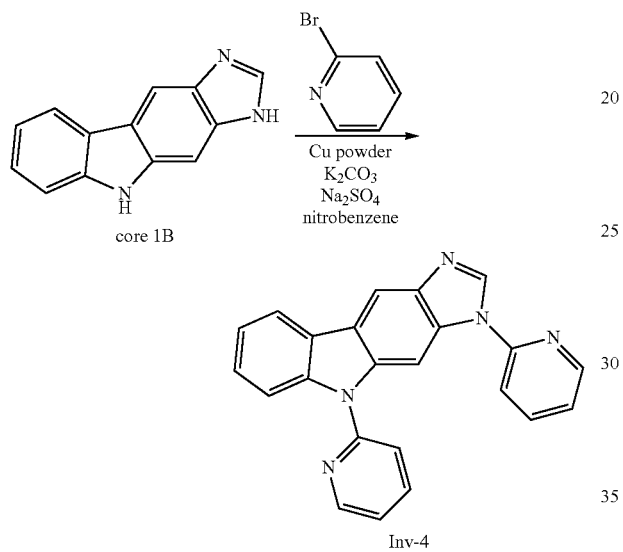

Inv-4

Compound Inv-4 (3.20 g, yield: 74%) was obtained by performing the same method as in Synthesis Example 1, except that 2.48 g of Compound Core1B synthesized in Preparation Example 1 was used instead of Compound Core1A used in Synthesis Example 1, and 2.83 g of 2-bromopyridine was used instead of 2-bromo-6-phenylpyridine used in Synthesis Example 1.

GC-Mass (theoretical value: 361.40 g/mol, measured value: 361 g/mol)

SYNTHESIS EXAMPLE 5

Synthesis of Compound Inv-5

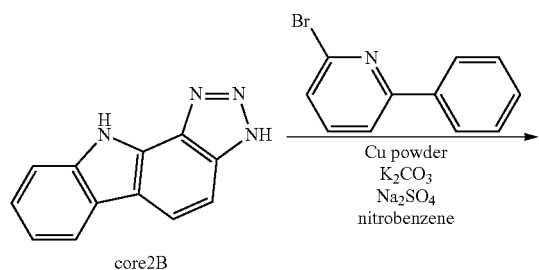

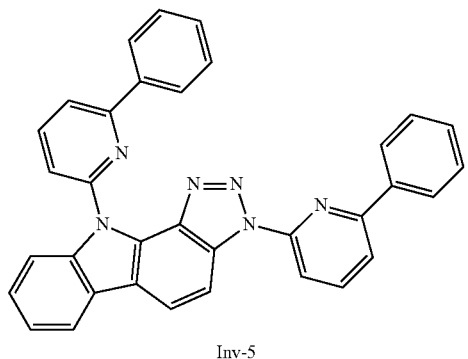

Inv-5

Compound Inv-5 (4.38 g, yield: 71%) was obtained by performing the same method as in Synthesis Example 1, except that 2.48 g of Compound Core2B synthesized in Preparation Example 2 was used instead of Compound Core1A used in Synthesis Example 1.

GC-Mass (theoretical value: 514.58 g/mol, measured value: 514 g/mol)

SYNTHESIS EXAMPLE 6

Synthesis of Compound Inv-6

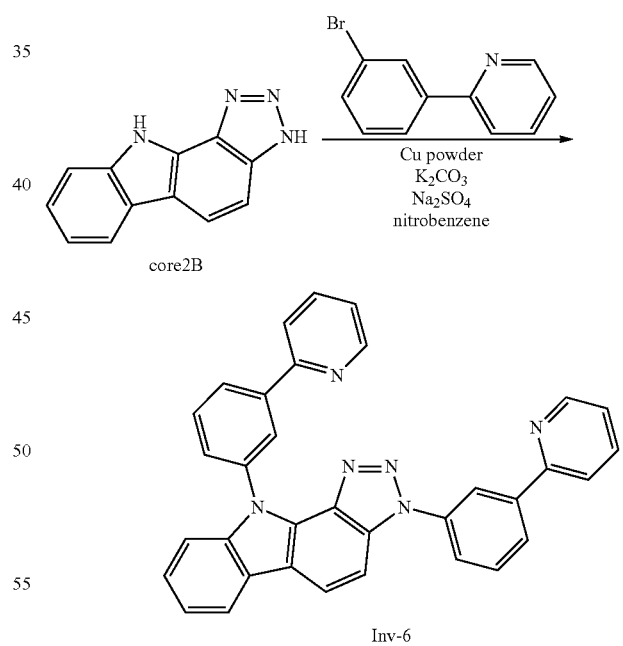

Inv-6

Compound Inv-6 (4.38 g, yield: 71%) was obtained by performing the same method as in Synthesis Example 2, except that 2.48 g of Compound Core2B synthesized in Preparation Example 2 was used instead of Compound Core1A used in Synthesis Example 2.

GC-Mass (theoretical value: 514.58 g/mol, measured value: 514 g/mol)

SYNTHESIS EXAMPLE 7

Synthesis of Compound Inv-7

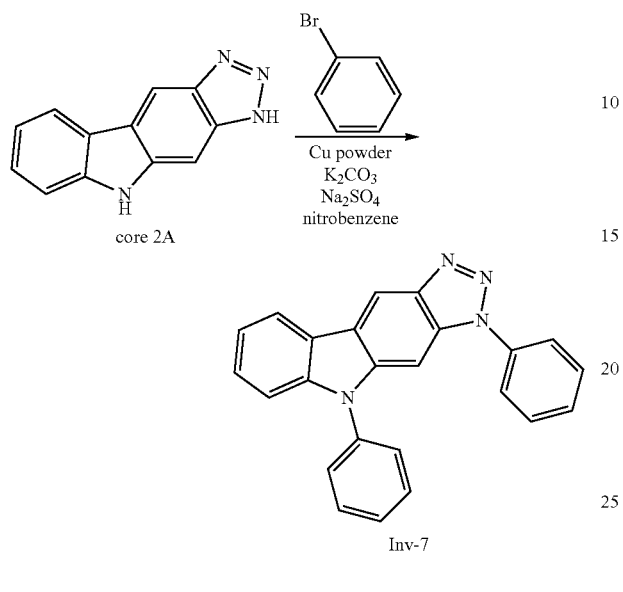

Compound Inv-7 (3.24 g, yield: 75%) was obtained by performing the same method as in Synthesis Example 3, except that 2.48 g of Compound Core2A synthesized in Preparation Example 2 was used instead of Compound Core1B used in Synthesis Example 3.

GC-Mass (theoretical value: 360.41 g/mol, measured value: 360 g/mol)

SYNTHESIS EXAMPLE 8

Synthesis of Compound Inv-8

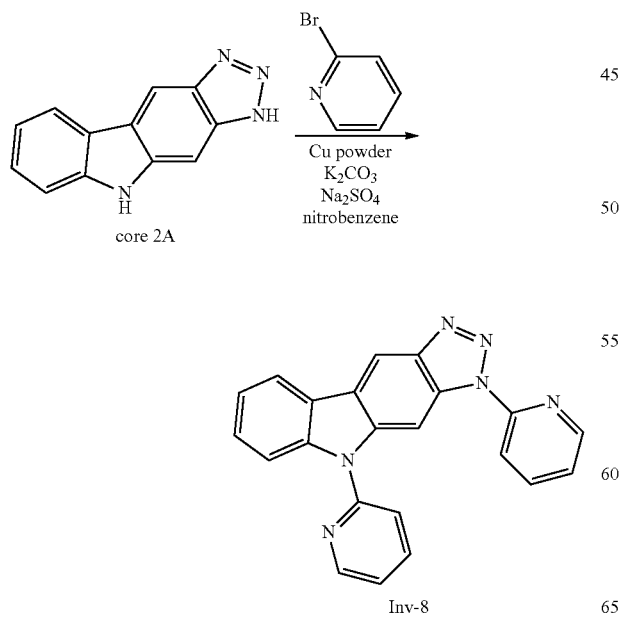

Compound Inv-8 (3.26 g, yield: 75%) was obtained by performing the same method as in Synthesis Example 4, except that 2.48 g of Compound Core2A synthesized in Preparation Example 2 was used instead of Compound Core1B used in Synthesis Example 4.

GC-Mass (theoretical value: 362.39 g/mol, measured value: 362 g/mol)

SYNTHESIS EXAMPLE 9

Synthesis of Compound Inv-9

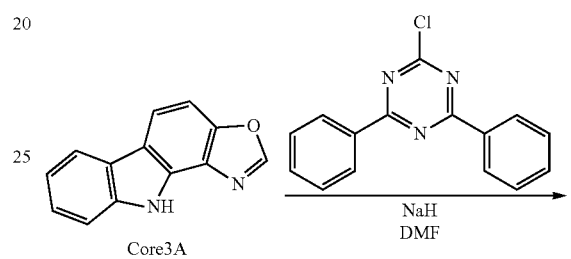

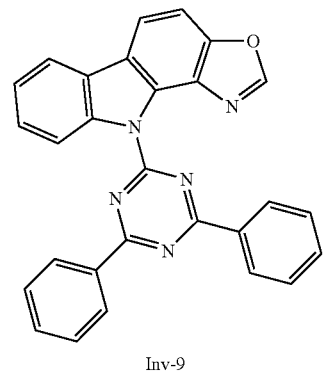

Compound Core3A (2.50 g, 12.00 mmol) synthesized in Preparation Example 3 was dissolved in 100 ml of DMF under nitrogen flow, NaH (0.43 g, 18.00 mmol) was added thereto, and the resulting mixture was stirred for 1 hour, thereby obtaining a reaction mixture. Thereafter, 2-chloro-4,6-diphenyl-1,3,5-triazine (3.84 g, 14.40 mmol) dissolved in 100 ml of DMF was slowly added to the reaction mixture. Thereafter, the mixture was stirred for 3 hours, the reaction was terminated, the resulting mixture was filtered through silica gel, and washed with water and methanol, and then the solvent was removed. The solid from which the solvent had been removed was purified by column chromatography (Hexane:EA=1:1 (v/v)), thereby obtaining Compound Inv-9 (3.74 g, yield: 71%).

GC-Mass (theoretical value: 439.47 g/mol, measured value: 439 g/mol)

SYNTHESIS EXAMPLE 10

Synthesis of Compound Inv-10

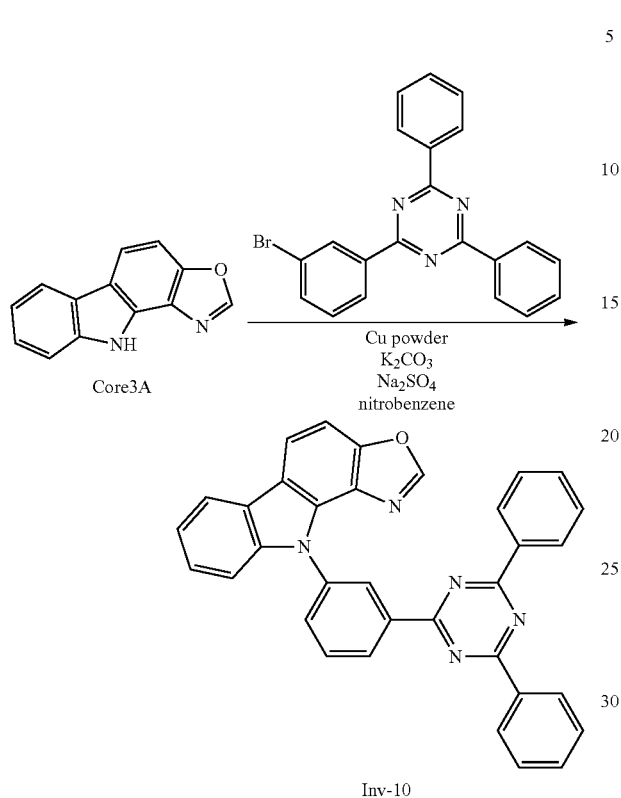

Compound Core3A (2.50 g, 12.00 mmol) synthesized in Preparation Example 3, 2-(3-bromophenyl)-4,6-diphenyl-1,3,5-triazine (5.59 g, 14.40 mmol), Cu powder (0.08 g, 1.20 mmol), $K_2CO_3$ (1.66 g, 12.00 mmol), $Na_2SO_4$ (1.71 g, 12.00 mmol), and nitrobenzene (100 ml) were mixed under nitrogen flow, and the mixture was stirred at 190° C. for 12 hours.

After the reaction was completed, nitrobenzene was removed, the organic layer was separated with methylene chloride, and water was removed from the organic layer by using $MgSO_4$. After the solvent was removed from the organic layer, the residue was purified by column chromatography (Hexane:EA=3:1 (v/v)), thereby obtaining Compound Inv-10 (4.45 g, yield: 72%).

GC-Mass (theoretical value: 515.56 g/mol, measured value: 515 g/mol)

SYNTHESIS EXAMPLE 11

Synthesis of Compound Inv-11

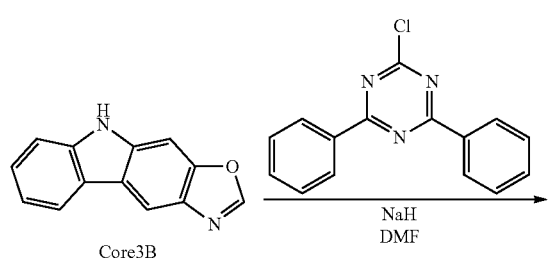

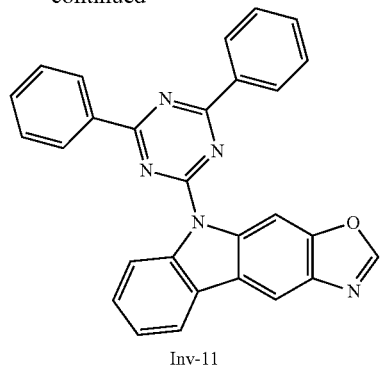

Compound Inv-11 (3.69 g, yield: 72%) was obtained by performing the same method as in Synthesis Example 9, except that 2.43 g of Compound Core3B synthesized in Preparation Example 3 was used instead of Compound Core3A used in Synthesis Example 9.

GC-Mass (theoretical value: 439.47 g/mol, measured value: 439 g/mol)

SYNTHESIS EXAMPLE 12

Synthesis of Compound Inv-12

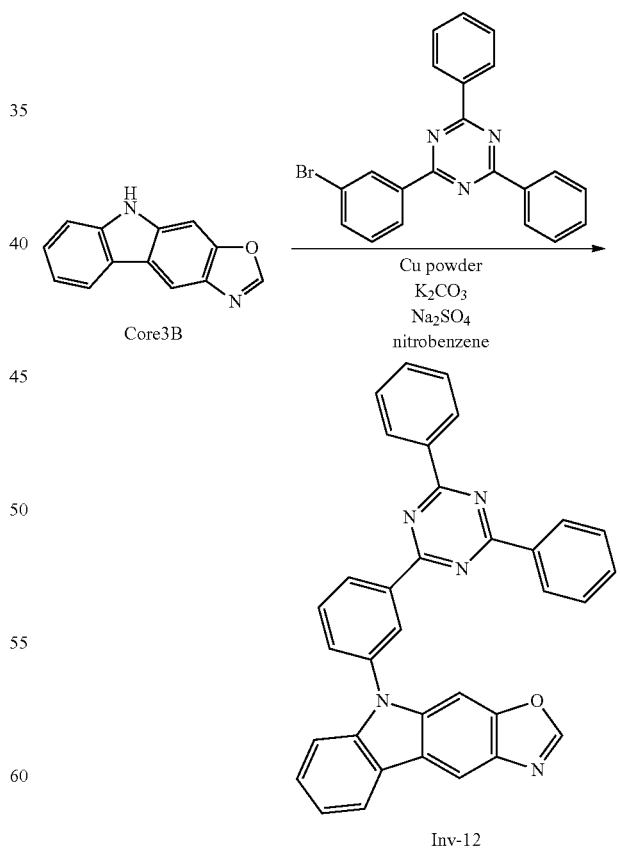

Compound Inv-12 (4.39 g, yield: 71%) was obtained by performing the same method as in Synthesis Example 10, except that 2.5 g of Compound Core3B synthesized in Preparation Example 3 was used instead of Compound Core3A used in Synthesis Example 10.

GC-Mass (theoretical value: 515.56 g/mol, measured value: 515 g/mol)

SYNTHESIS EXAMPLE 13

Synthesis of Compound Inv-13

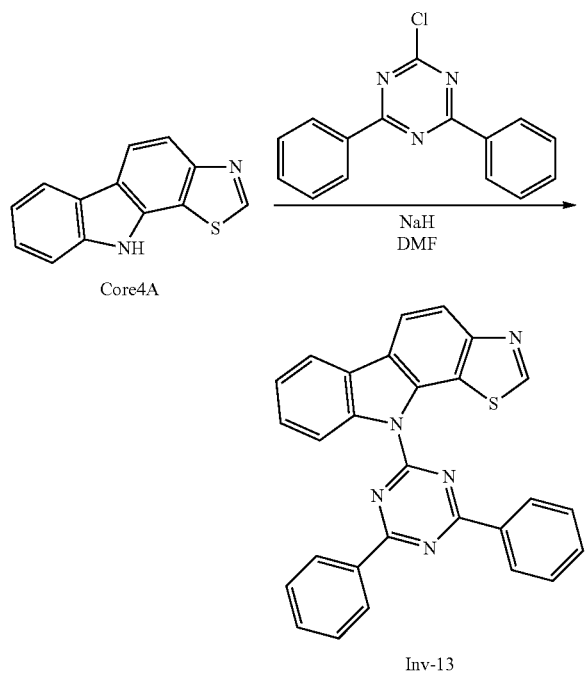

Inv-13

Compound Inv-13 (3.82 g, yield: 70%) was obtained by performing the same method as in Synthesis Example 9, except that 2.68 g of Compound Core4A synthesized in Preparation Example 4 was used instead of Compound Core3A used in Synthesis Example 9.

GC-Mass (theoretical value: 455.53 g/mol, measured value: 455 g/mol)

SYNTHESIS EXAMPLE 14

Synthesis of Compound Inv-14

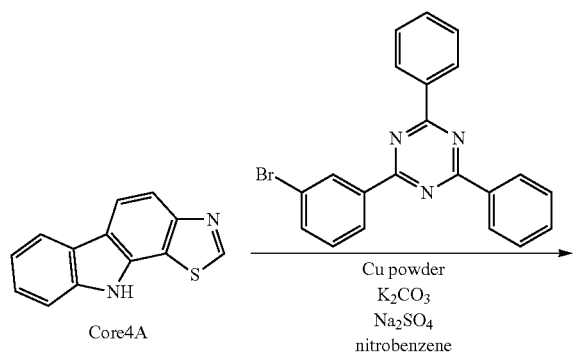

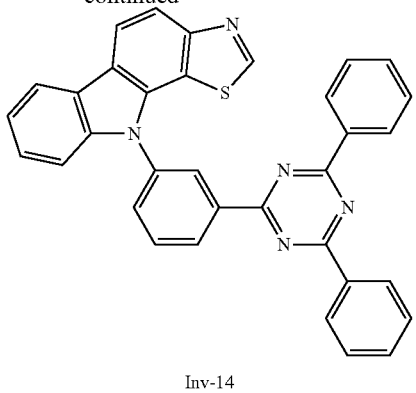

Inv-14

Compound Inv-12 (4.46 g, yield: 70%) was obtained by performing the same method as in Synthesis Example 10, except that 2.68 g of Compound Core4A synthesized in Preparation Example 4 was used instead of Compound Core3A used in Synthesis Example 10.

GC-Mass (theoretical value: 531.63 g/mol, measured value: 531 g/mol)

SYNTHESIS EXAMPLE 15

Synthesis of Compound Inv-15

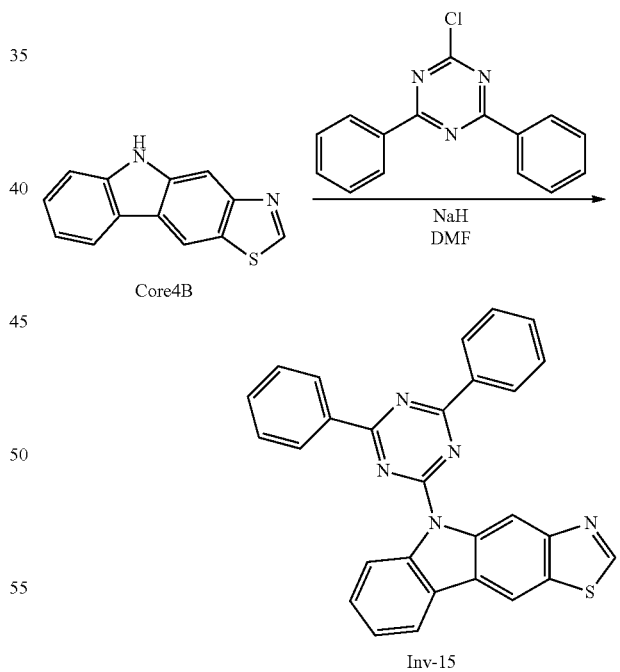

Inv-15

Compound Inv-15 (3.76 g, yield: 69%) was obtained by performing the same method as in Synthesis Example 9, except that 2.68 g of Compound Core4B synthesized in Preparation Example 4 was used instead of Compound Core3A used in Synthesis Example 9.

GC-Mass (theoretical value: 455.53 g/mol, measured value: 455 g/mol)

SYNTHESIS EXAMPLE 16

Synthesis of Compound Inv-16

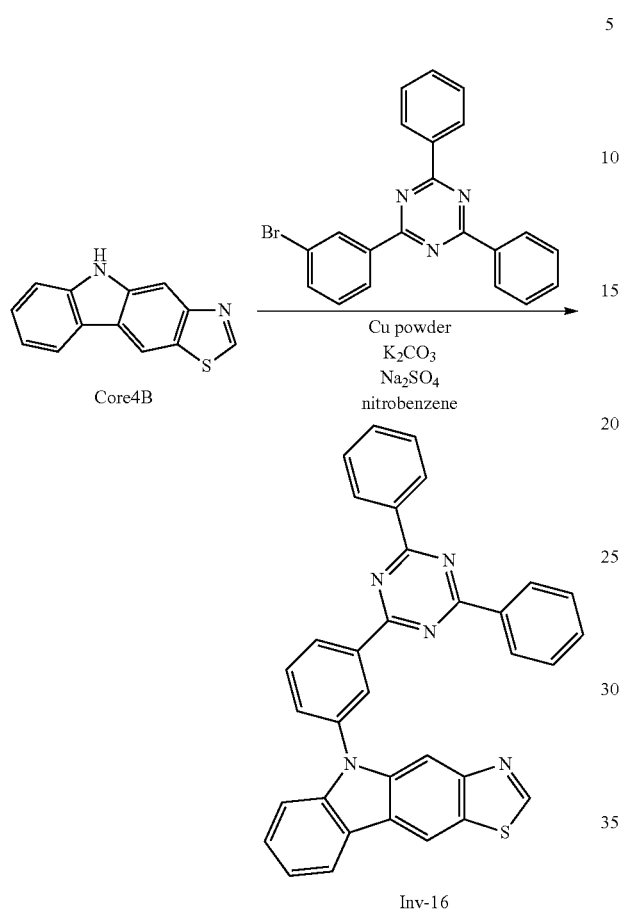

Compound Inv-16 (4.46 g, yield: 70%) was obtained by performing the same method as in Synthesis Example 10, except that 2.68 g of Compound Core4B synthesized in Preparation Example 4 was used instead of Compound Core3A used in Synthesis Example 10.

GC-Mass (theoretical value: 531.63 g/mol, measured value: 531 g/mol)

SYNTHESIS EXAMPLE 17

Synthesis of Compound Inv-17

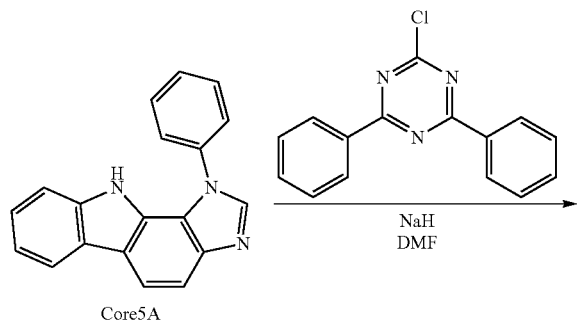

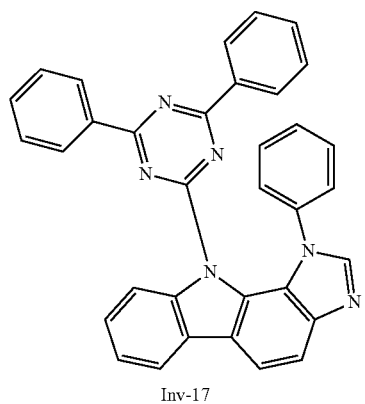

Compound Inv-17 (4.63 g, yield: 69%) was obtained by performing the same method as in Synthesis Example 9, except that 3.69 g of Compound Core5A synthesized in Preparation Example 5 was used instead of Compound Core3A used in Synthesis Example 9.

GC-Mass (theoretical value: 514.58 g/mol, measured value: 514 g/mol)

SYNTHESIS EXAMPLE 18

Synthesis of Compound Inv-18

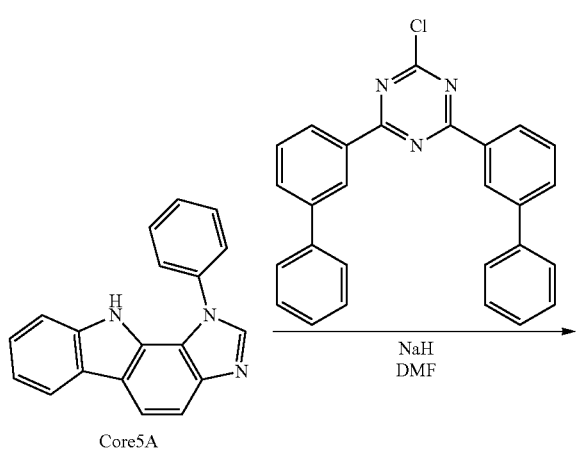

-continued

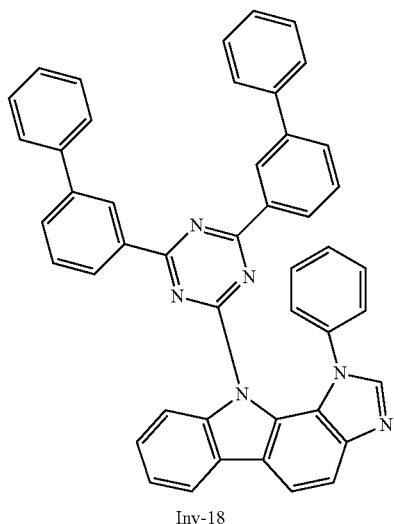

Inv-18

Compound Inv-18 (5.43 g, yield: 68%) was obtained by performing the same method as in Synthesis Example 9, except that 3.39 g of Compound Core5A synthesized in Preparation Example 5 was used instead of Compound Core3A used in Synthesis Example 9, and 6 g of 2,4-di(biphenyl-3-yl)-6-chloro-1,3,5-triazine was used instead of 2-chloro-4,6-diphenyl-1,3,5-triazine used in Synthesis Example 9.

GC-Mass (theoretical value: 666.77 g/mol, measured value: 666 g/mol)

SYNTHESIS EXAMPLE 19

Synthesis of Compound Inv-19

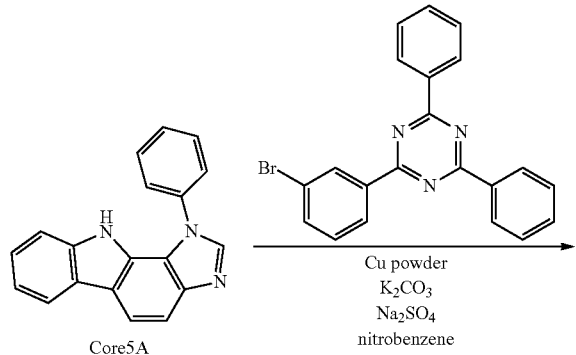

-continued

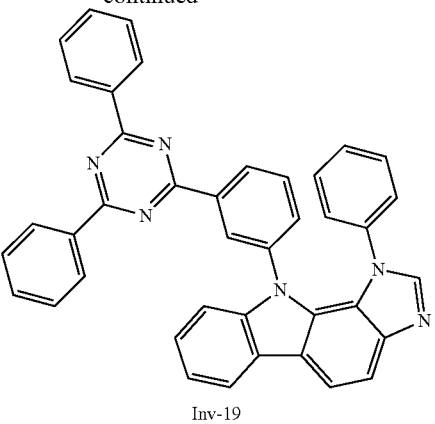

Inv-19

Compound Inv-19 (4.95 g, yield: 70%) was obtained by performing the same method as in Synthesis Example 10, except that 3.39 g of Compound Core5A synthesized in Preparation Example 5 was used instead of Compound Core3A used in Synthesis Example 10.

GC-Mass (theoretical value: 590.67 g/mol, measured value: 590 g/mol)

SYNTHESIS EXAMPLE 20

Synthesis of Compound Inv-20

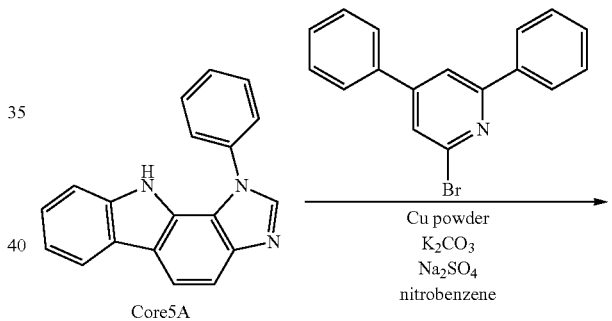

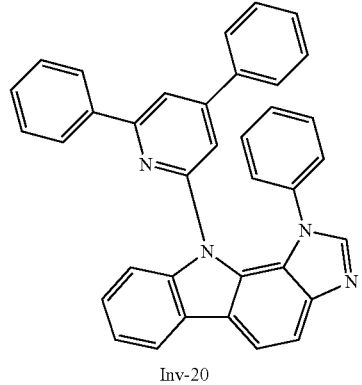

Inv-20

Compound Inv-20 (4.17 g, yield: 68%) was obtained by performing the same method as in Synthesis Example 10, except that Core5A synthesized in Preparation Example 5 was used instead of Compound Core3A used in Synthesis Example 10, and 5.56 g of 2-bromo-6-phenylpyridine was used instead of 2-chloro-4,6-diphenyl-1,3,5-triazine used in Synthesis Example 10.

GC-Mass (theoretical value: 512.60 g/mol, measured value: 512 g/mol)

SYNTHESIS EXAMPLE 21

Synthesis of Compound Inv-21

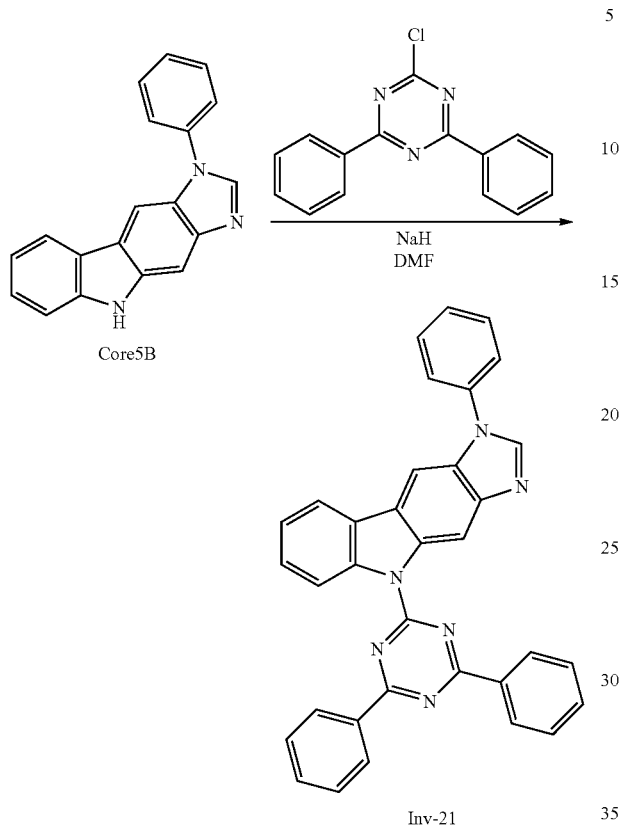

Inv-21

Compound Inv-21 (4.01 g, yield: 65%) was obtained by performing the same method as in Synthesis Example 9, except that 3.39 g of Compound Core5B synthesized in Preparation Example 5 was used instead of Compound Core3A used in Synthesis Example 9.

GC-Mass (theoretical value: 514.58 g/mol, measured value: 514 g/mol)

SYNTHESIS EXAMPLE 22

Synthesis of Compound Inv-22

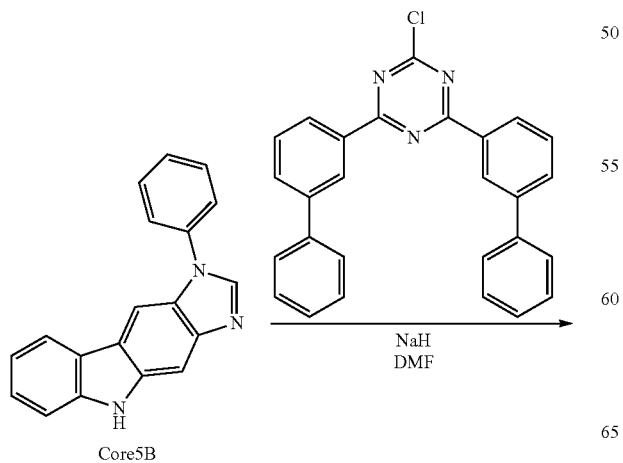

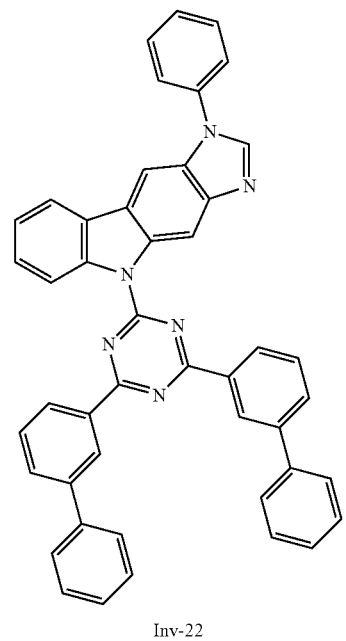

Inv-22

Compound Inv-22 (5.43 g, yield: 68%) was obtained by performing the same method as in Synthesis Example 18, except that 3.39 g of Compound Core5B synthesized in Preparation Example 5 was used instead of Compound Core5A used in Synthesis Example 18.

GC-Mass (theoretical value: 666.77 g/mol, measured value: 666 g/mol)

SYNTHESIS EXAMPLE 23

Synthesis of Compound Inv-23

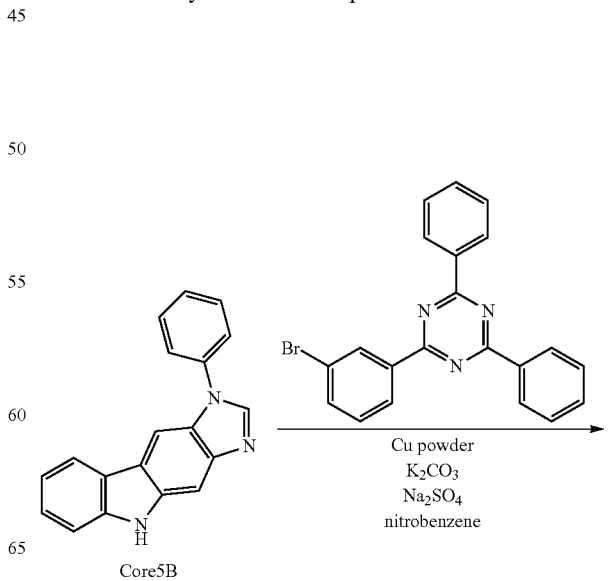

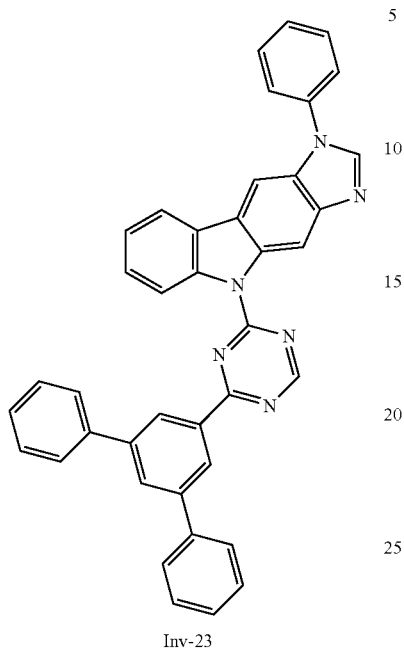

Inv-23

Compound Inv-23 (4.88 g, yield: 69%) was obtained by performing the same method as in Synthesis Example 10, except that 3.39 g of Compound Core5B synthesized in Preparation Example 5 was used instead of Compound Core3A used in Synthesis Example 10.

GC-Mass (theoretical value: 590.67 g/mol, measured value: 590 g/mol)

SYNTHESIS EXAMPLE 24

Synthesis of Compound Inv-24

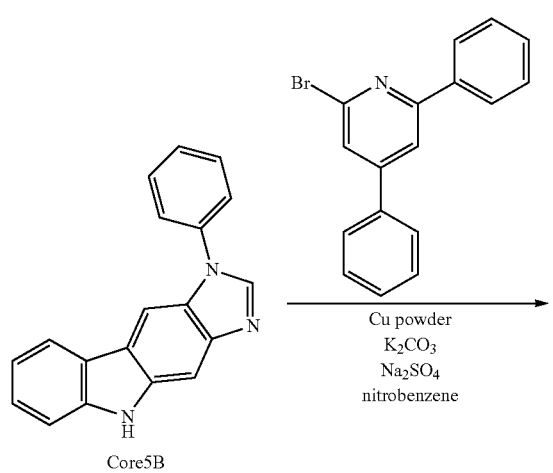

Core5B

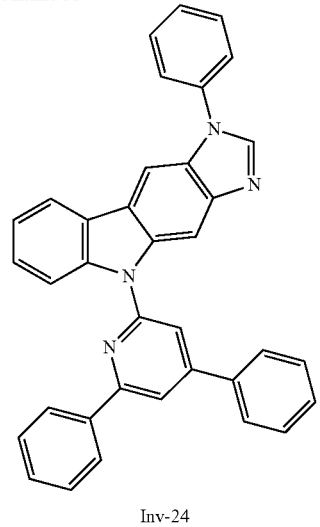

Inv-24

Compound Inv-24 (3.99 g, yield: 65%) was obtained by performing the same method as in Synthesis Example 20, except that 3.39 g of Compound Core5B synthesized in Preparation Example 5 was used instead of Compound Core5A used in Synthesis Example 20.

GC-Mass (theoretical value: 512.60 g/mol, measured value: 512 g/mol)

SYNTHESIS EXAMPLE 25

Synthesis of Compound Inv-25

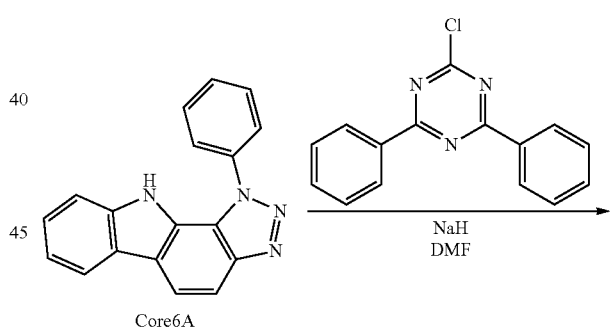

Core6A

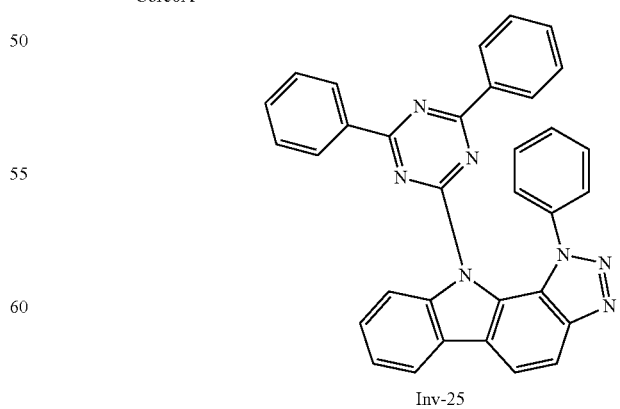

Inv-25

Compound Inv-25 (4.20 g, yield: 68%) was obtained by performing the same method as in Synthesis Example 9, except that 3.4 g of Compound Core6A synthesized in Preparation Example 6 was used instead of Compound Core3A used in Synthesis Example 9.

GC-Mass (theoretical value: 515.57 g/mol, measured value: 515 g/mol)

SYNTHESIS EXAMPLE 26

Synthesis of Compound Inv-26

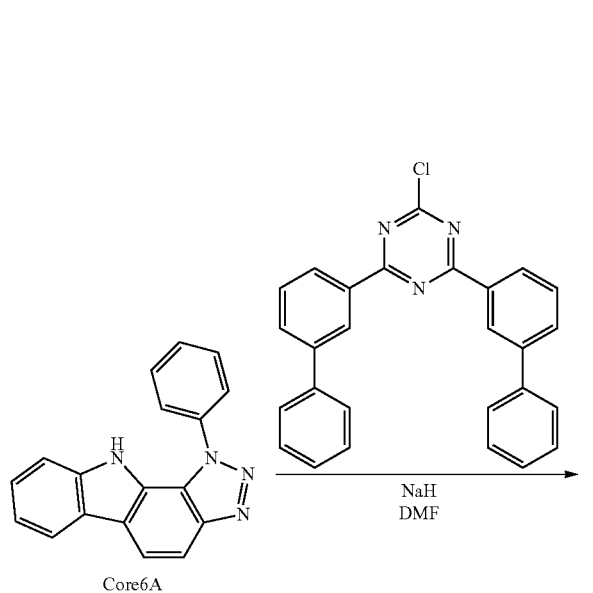

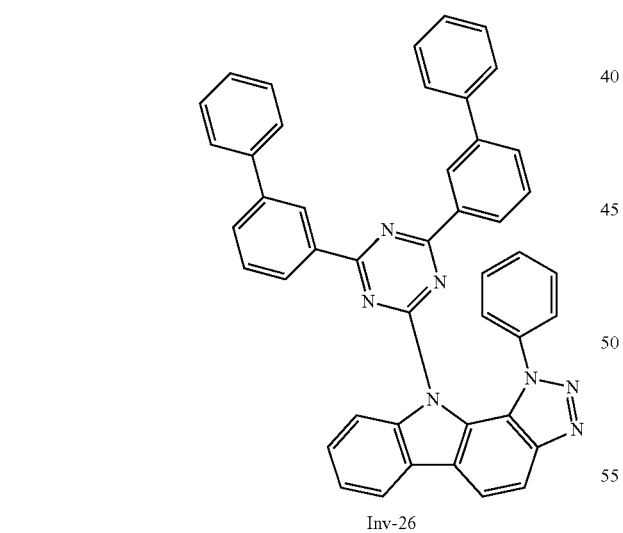

Compound Inv-26 (5.20 g, yield: 65%) was obtained by performing the same method as in Synthesis Example 18, except that 3.4 g of Compound Core6A synthesized in Preparation Example 6 was used instead of Compound Core5A used in Synthesis Example 18.

GC-Mass (theoretical value: 667.76 g/mol, measured value: 667 g/mol)

SYNTHESIS EXAMPLE 27

Synthesis of Compound Inv-27

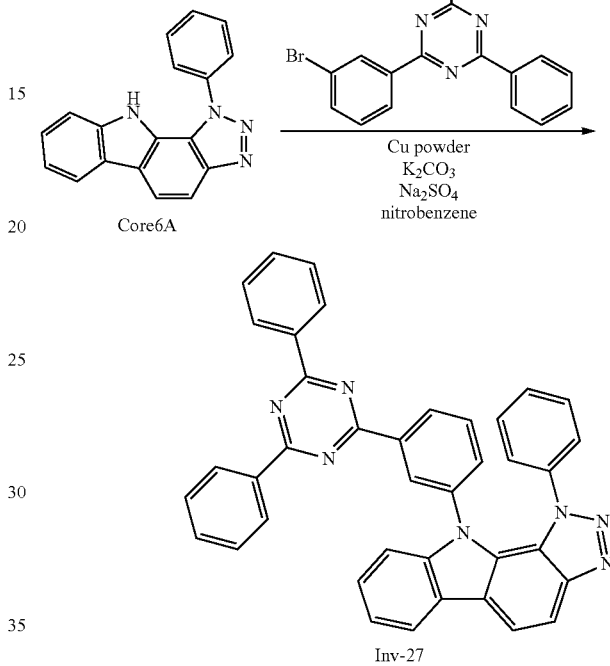

Compound Inv-27 (4.68 g, yield: 66%) was obtained by performing the same method as in Synthesis Example 10, except that 3.4 g of Compound Core6A synthesized in Preparation Example 6 was used instead of Compound Core3A used in Synthesis Example 10.

GC-Mass (theoretical value: 591.66 g/mol, measured value: 591 g/mol)

SYNTHESIS EXAMPLE 28

Synthesis of Compound Inv-28

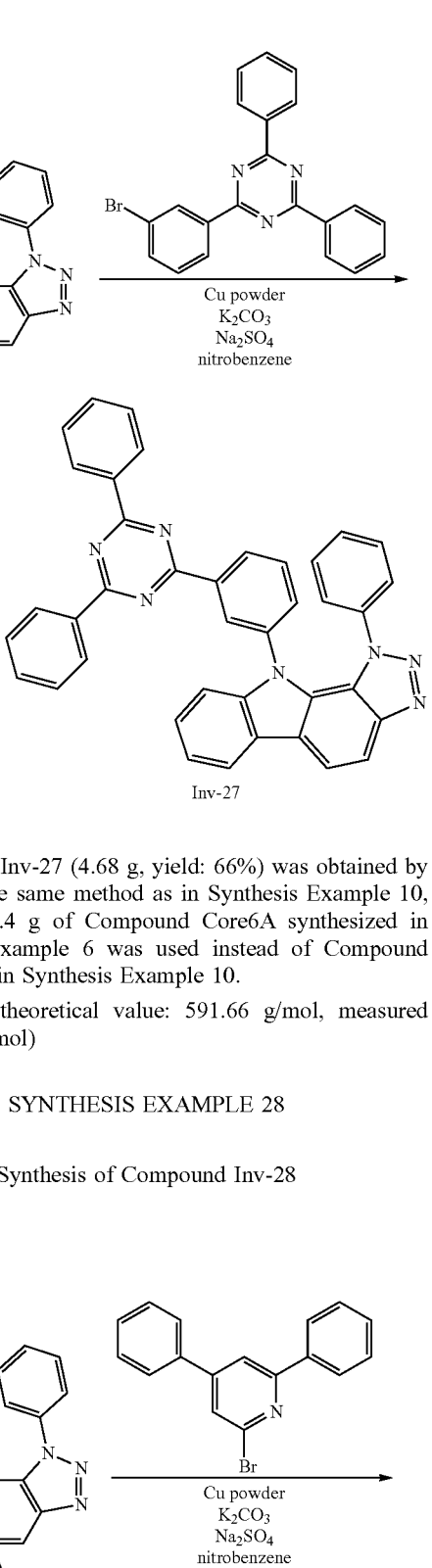

-continued

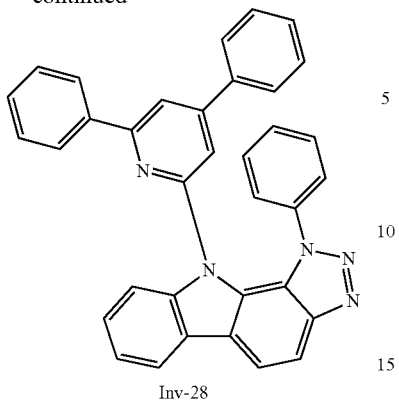

Inv-28

Compound Inv-28 (4.00 g, yield: 65%) was obtained by performing the same method as in Synthesis Example 20, except that 3.4 g of Compound Core6A synthesized in Preparation Example 6 was used instead of Compound Core5A used in Synthesis Example 20.

GC-Mass (theoretical value: 513.59 g/mol, measured value: 513 g/mol)

SYNTHESIS EXAMPLE 29

Synthesis of Compound Inv-29

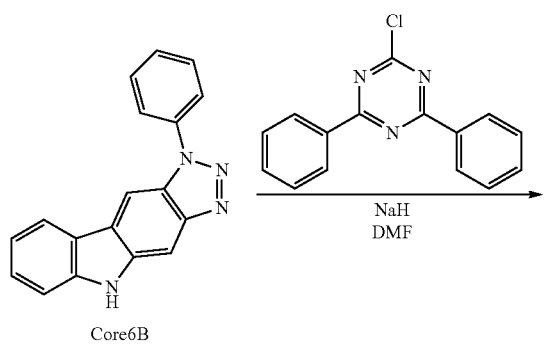

Core6B

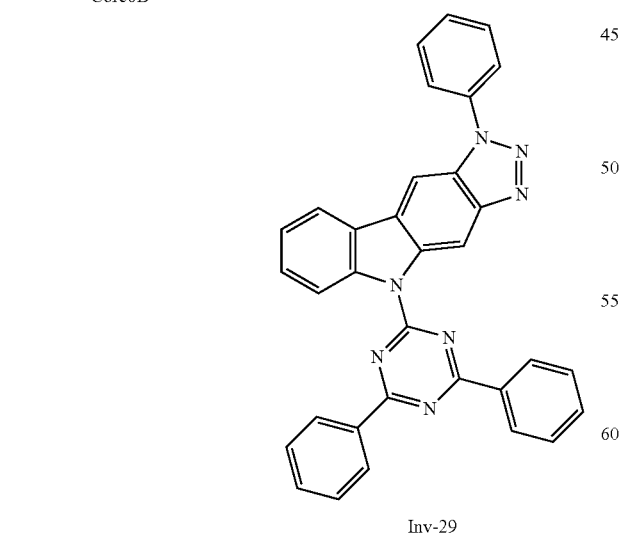

Inv-29

Compound Inv-29 (4.14 g, yield: 67%) was obtained by performing the same method as in Synthesis Example 9, except that 3.4 g of Compound Core6B synthesized in Preparation Example 6 was used instead of Compound Core3A used in Synthesis Example 9.

GC-Mass (theoretical value: 515.57 g/mol, measured value: 515 g/mol)

SYNTHESIS EXAMPLE 30

Synthesis of Compound Inv-30

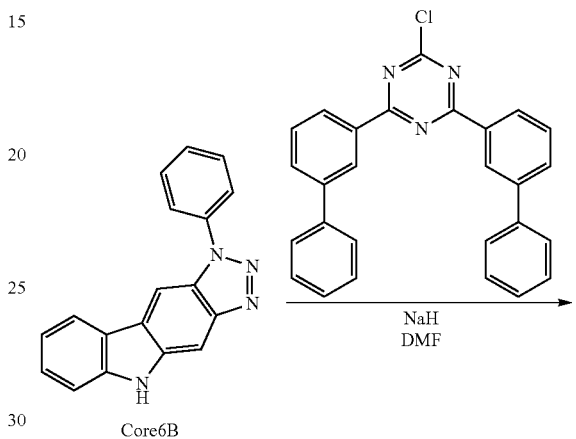

Core6B

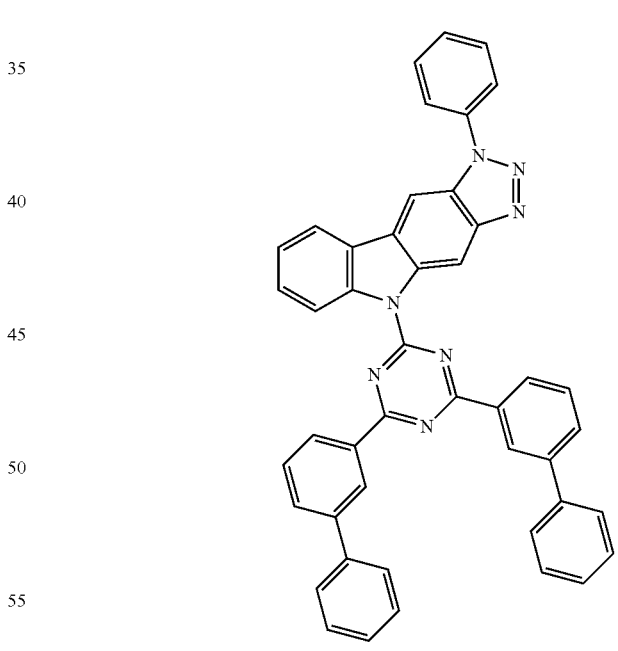

Inv-30

Compound Inv-30 (5.28 g, yield: 66%) was obtained by performing the same method as in Synthesis Example 18, except that 3.4 g of Compound Core6B synthesized in Preparation Example 6 was used instead of Compound Core5A used in Synthesis Example 18.

GC-Mass (theoretical value: 667.76 g/mol, measured value: 667 g/mol)

SYNTHESIS EXAMPLE 31

Synthesis of Compound Inv-31

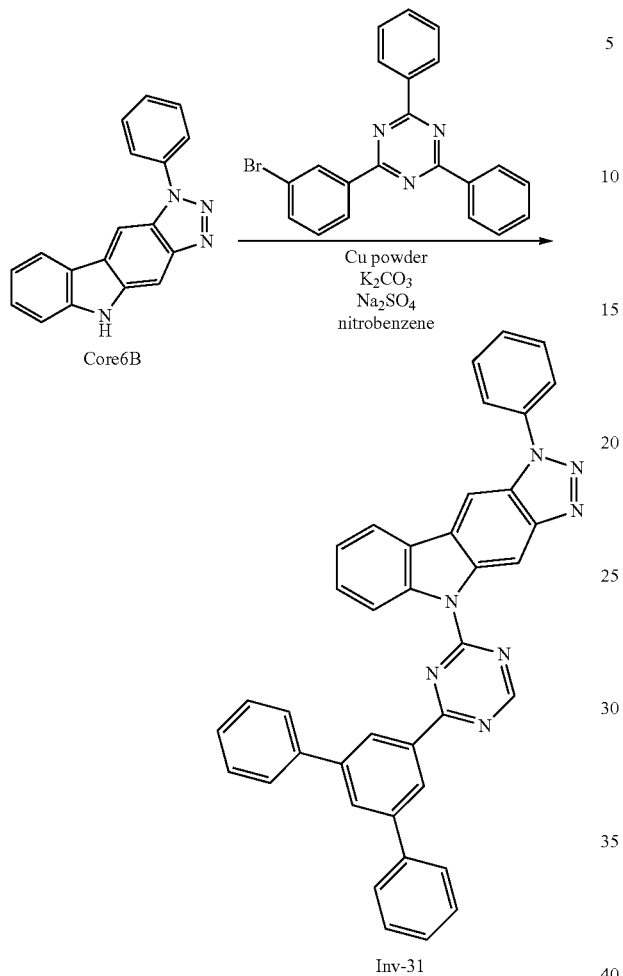

Inv-31

Compound Inv-31 (4.89 g, yield: 69%) was obtained by performing the same method as in Synthesis Example 10, except that 3.4 g of Compound Core6B synthesized in Preparation Example 6 was used instead of Compound Core3A used in Synthesis Example 10.

GC-Mass (theoretical value: 591.66 g/mol, measured value: 591 g/mol)

SYNTHESIS EXAMPLE 32

Synthesis of Compound Inv-32

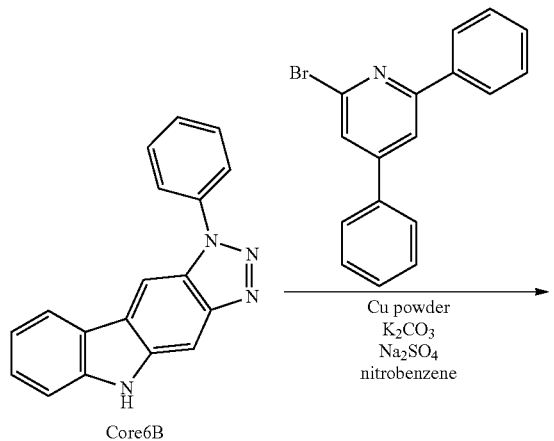

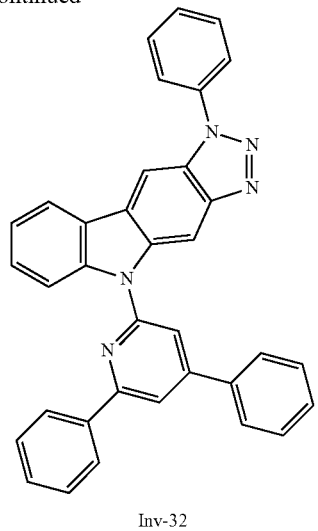

Inv-32

Compound Inv-32 (4.31 g, yield: 70%) was obtained by performing the same method as in Synthesis Example 20, except that 3.4 g of Compound Core6B synthesized in Preparation Example 6 was used instead of Compound Core5A used in Synthesis Example 20.

GC-Mass (theoretical value: 513.59 g/mol, measured value: 513 g/mol)

SYNTHESIS EXAMPLE 33

Synthesis of Compound Inv-33

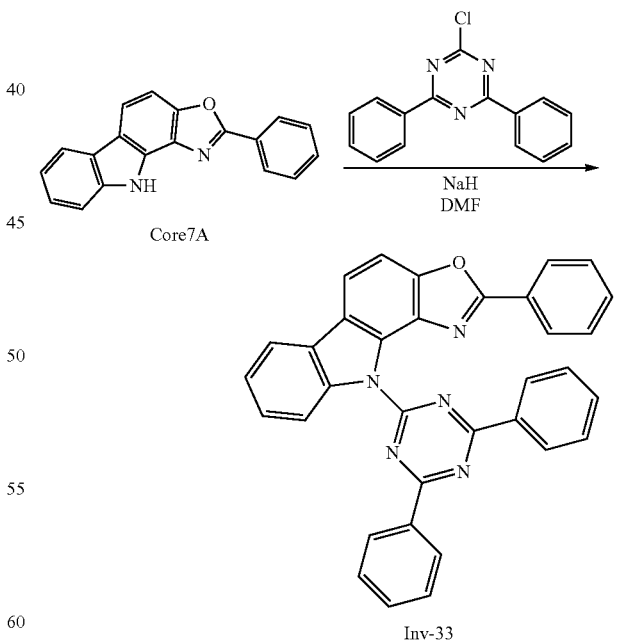

Inv-33

Compound Inv-33 (4.07 g, yield: 66%) was obtained by performing the same method as in Synthesis Example 9, except that 3.4 g of Compound Core7A synthesized in Preparation Example 7 was used instead of Compound Core3A synthesized in Synthesis Example 9.

GC-Mass (theoretical value: 515.56 g/mol, measured value: 515 g/mol)

SYNTHESIS EXAMPLE 34

Synthesis of Compound Inv-34

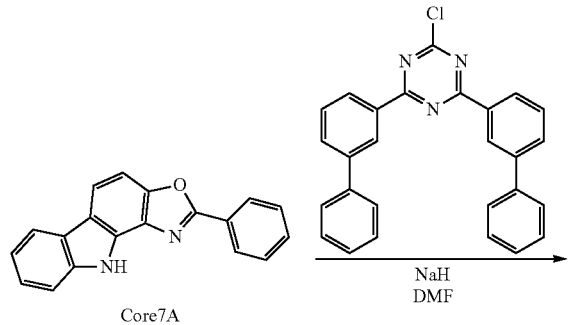

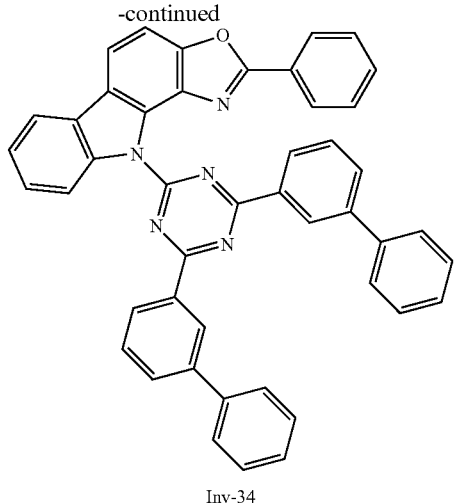

Inv-34

Compound Inv-34 (5.12 g, yield: 64%) was obtained by performing the same method as in Synthesis Example 9, except that 3.4 g of Compound Core7A synthesized in Preparation Example 7 was used instead of Compound Core5A used in Synthesis Example 18.

GC-Mass (theoretical value: 667.76 g/mol, measured value: 667 g/mol)

SYNTHESIS EXAMPLE 35

Synthesis of Compound Inv-35

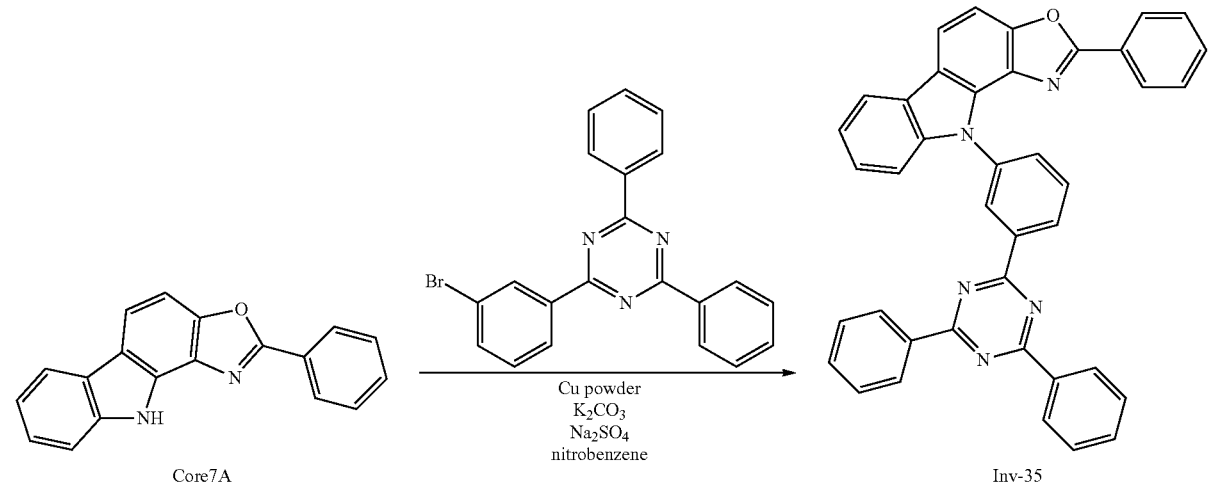

Compound Inv-35 (4.60 g, yield: 65%) was obtained by performing the same method as in Synthesis Example 10, except that 3.4 g of Compound Core7A synthesized in Preparation Example 7 was used instead of Compound Core3A used in Synthesis Example 10.

GC-Mass (theoretical value: 591.66 g/mol, measured value: 591 g/mol)

SYNTHESIS EXAMPLE 36

Synthesis of Compound Inv-36

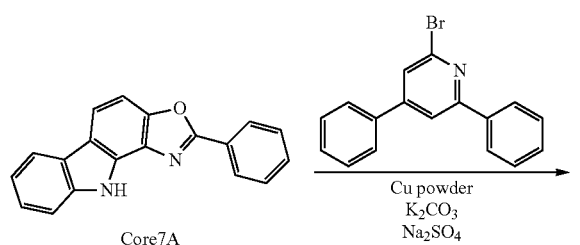

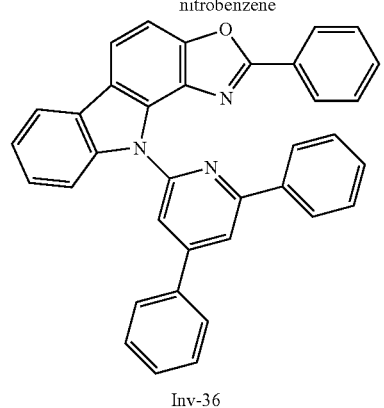

Inv-36

Compound Inv-36 (3.69 g, yield: 60%) was obtained by performing the same method as in Synthesis Example 20, except that 3.4 g of Compound Core7A synthesized in Preparation Example 7 was used instead of Compound Core5A used in Synthesis Example 20.

GC-Mass (theoretical value: 513.59 g/mol, measured value: 513 g/mol)

SYNTHESIS EXAMPLE 37

Synthesis of Compound Inv-37

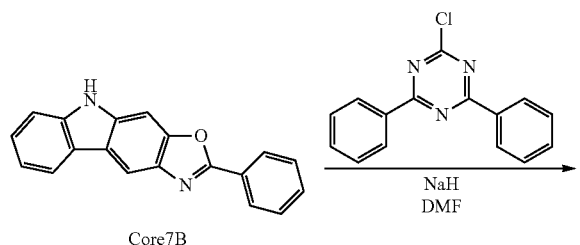

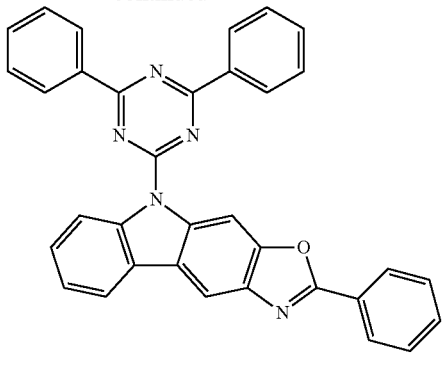

Inv-37

Compound Inv-37 (4.14 g, yield: 67%) was obtained by performing the same method as in Synthesis Example 9, except that 3.4 g of Compound Core7B synthesized in Preparation Example 7 was used instead of Compound Core3A used in Synthesis Example 9.

GC-Mass (theoretical value: 515.56 g/mol, measured value: 515 g/mol)

SYNTHESIS EXAMPLE 38

Synthesis of Compound Inv-38

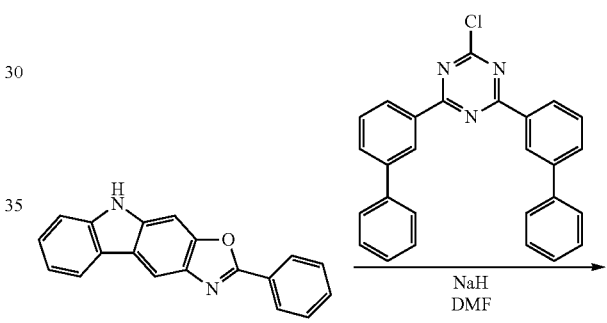

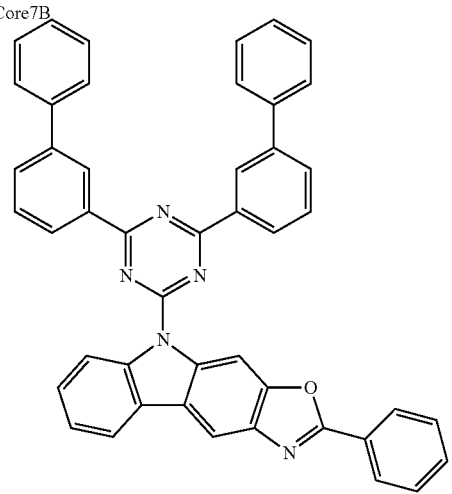

Inv-38

Compound Inv-38 (4.96 g, yield: 62%) was obtained by performing the same method as in Synthesis Example 18, except that 3.4 g of Compound Core7B synthesized in Preparation Example 7 was used instead of Compound Core5A used in Synthesis Example 18.

GC-Mass (theoretical value: 667.76 g/mol, measured value: 667 g/mol)

SYNTHESIS EXAMPLE 39

Synthesis of Compound Inv-39

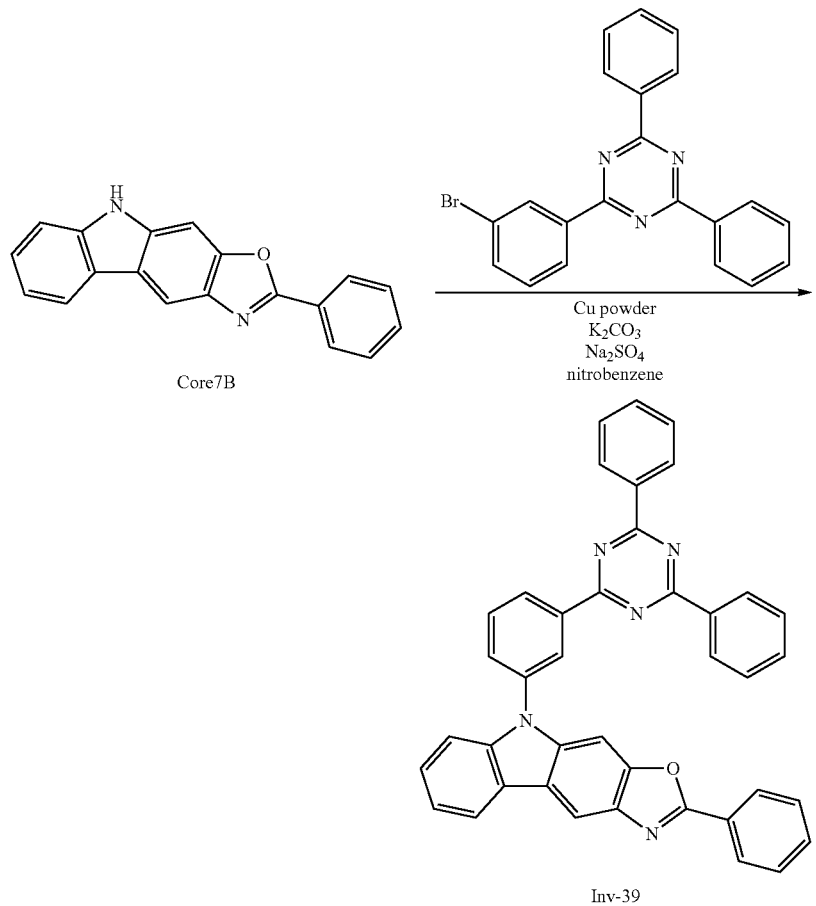 [SMILES: c1ccc(-c2nc3cc4c(cc3o2)[nH]c2ccccc24)cc1 ; Brc1cccc(-c2nc(-c3ccccc3)nc(-c3ccccc3)n2)c1 ; c1ccc(-c2nc(-c3ccccc3)nc(-c3cccc(-n4c5ccccc5c5cc6nc(-c7ccccc7)oc6cc54)c3)n2)cc1]

Compound Inv-39 (4.82 g, yield: 68%) was obtained by performing the same method as in Synthesis Example 10, except that 3.4 g of Compound Core7B synthesized in Preparation Example 7 was used instead of Compound Core3A used in Synthesis Example 10.

GC-Mass (theoretical value: 591.66 g/mol, measured value: 591 g/mol)

SYNTHESIS EXAMPLE 40

Synthesis of Compound Inv-40

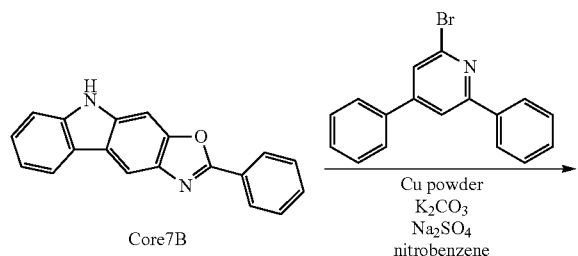

-continued

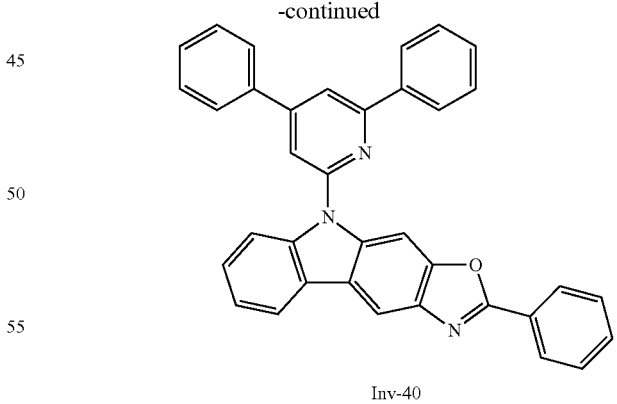

Compound Inv-40 (4.00 g, yield: 65%) was obtained by performing the same method as in Synthesis Example 20, except that 3.4 g of Compound Core7B synthesized in Preparation Example 7 was used instead of Compound Core5A used in Synthesis Example 20.

GC-Mass (theoretical value: 513.59 g/mol, measured value: 513 g/mol)

SYNTHESIS EXAMPLE 41

Synthesis of Compound Inv-41

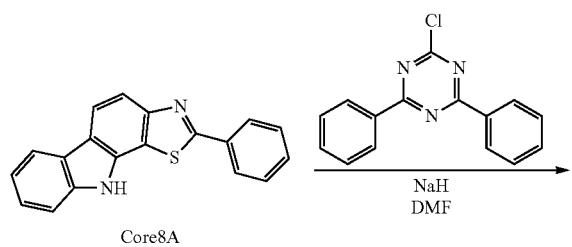

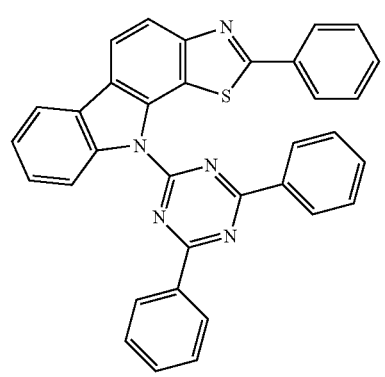

Inv-41

Compound Inv-41 (4.07 g, yield: 64%) was obtained by performing the same method as in Synthesis Example 9, except that 3.6 g of Compound Core8A synthesized in Preparation Example 8 was used instead of Compound Core3A used in Synthesis Example 9.

GC-Mass (theoretical value: 531.63 g/mol, measured value: 531 g/mol)

SYNTHESIS EXAMPLE 42

Synthesis of Compound Inv-42

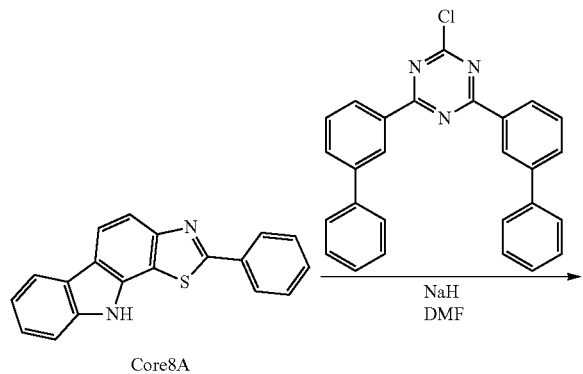

-continued

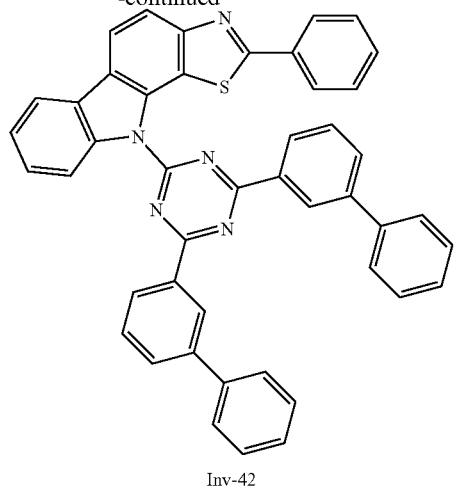

Inv-42

Compound Inv-42 (4.99 g, yield: 61%) was obtained by performing the same method as in Synthesis Example 18, except that 3.6 g of Compound Core8A synthesized in Preparation Example 8 was used instead of Compound Core5A used in Synthesis Example 18.

GC-Mass (theoretical value: 683.82 g/mol, measured value: 683 g/mol)

SYNTHESIS EXAMPLE 43

Synthesis of Compound Inv-43

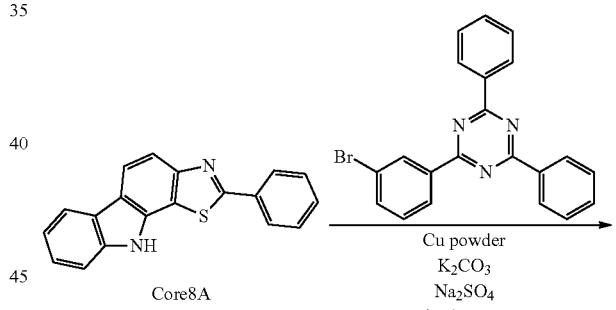

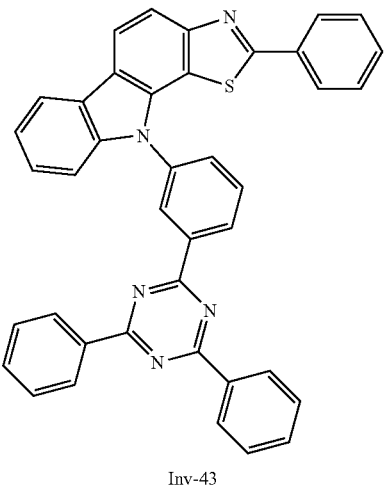

Inv-43

Compound Inv-43 (4.51 g, yield: 62%) was obtained by performing the same method as in Synthesis Example 10, except that 3.6 g of Compound Core8A synthesized in Preparation Example 8 was used instead of Compound Core3A used in Synthesis Example 10.

GC-Mass (theoretical value: 607.73 g/mol, measured value: 607 g/mol)

SYNTHESIS EXAMPLE 44

Synthesis of Compound Inv-44

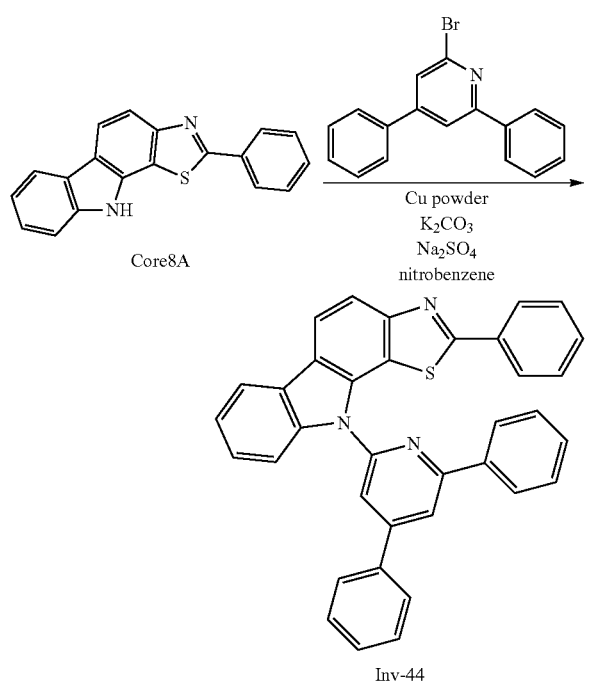

Inv-44

Compound Inv-44 (4.12 g, yield: 65%) was obtained by performing the same method as in Synthesis Example 20, except that 3.6 g of Compound Core8A synthesized in Preparation Example 8 was used instead of Compound Core5A used in Synthesis Example 20.

GC-Mass (theoretical value: 529.65 g/mol, measured value: 529 g/mol)

SYNTHESIS EXAMPLE 45

Synthesis of Compound Inv-45

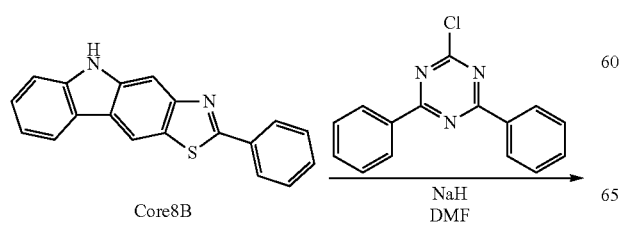

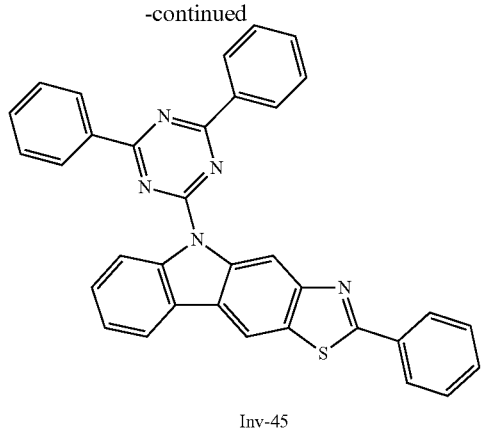

Inv-45

Compound Inv-45 (4.33 g, yield: 66%) was obtained by performing the same method as in Synthesis Example 9, except that 3.6 g of Compound Core8B synthesized in Preparation Example 8 was used instead of Compound Core3A used in Synthesis Example 9.

GC-Mass (theoretical value: 531.63 g/mol, measured value: 531 g/mol)

SYNTHESIS EXAMPLE 46

Synthesis of Compound Inv-46

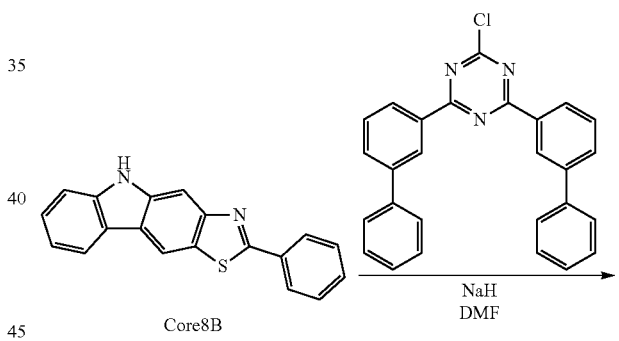

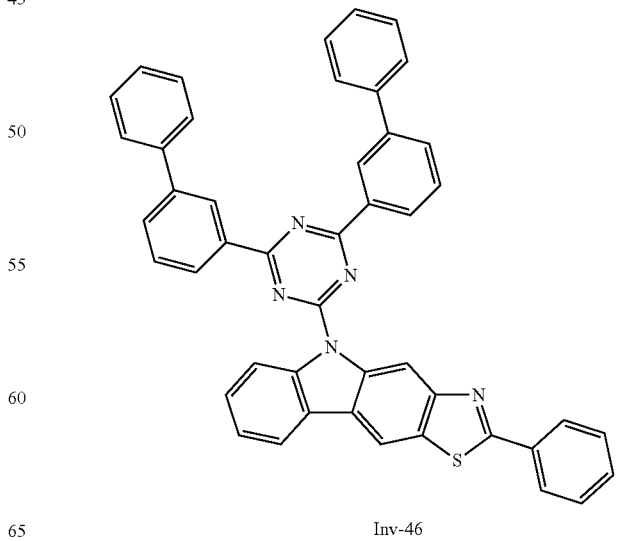

Inv-46

Compound Inv-46 (5.41 g, yield: 66%) was obtained by performing the same method as in Synthesis Example 18, except that 3.6 g of Compound Core8B synthesized in Preparation Example 8 was used instead of Compound Core5A used in Synthesis Example 18.

GC-Mass (theoretical value: 683.82 g/mol, measured value: 683 g/mol)

SYNTHESIS EXAMPLE 47

Synthesis of Compound Inv-47

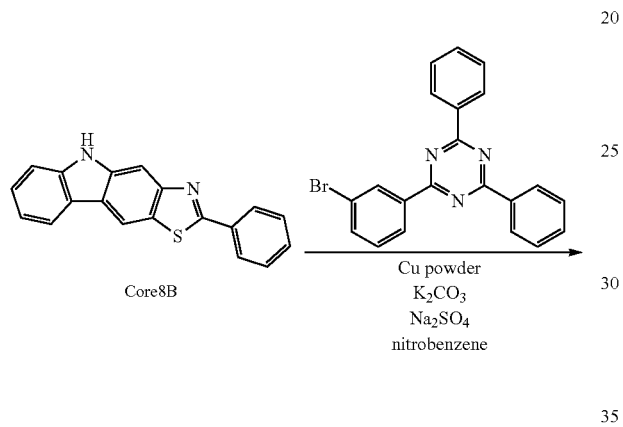

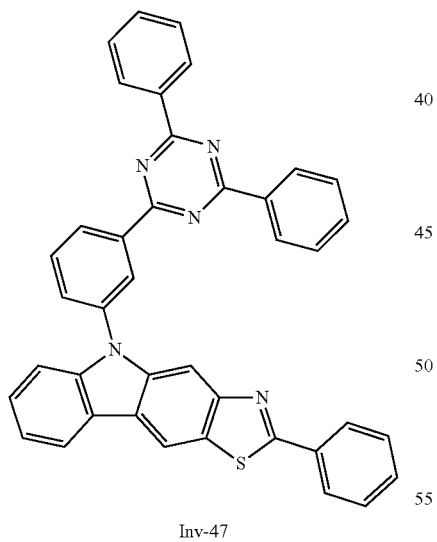

Inv-47

Compound Inv-47 (4.59 g, yield: 63%) was obtained by performing the same method as in Synthesis Example 10, except that 3.6 g of Compound Core8B synthesized in Preparation Example 8 was used instead of Compound Core3A used in Synthesis Example 10.

GC-Mass (theoretical value: 607.73 g/mol, measured value: 607 g/mol)

SYNTHESIS EXAMPLE 48

Synthesis of Compound Inv-48

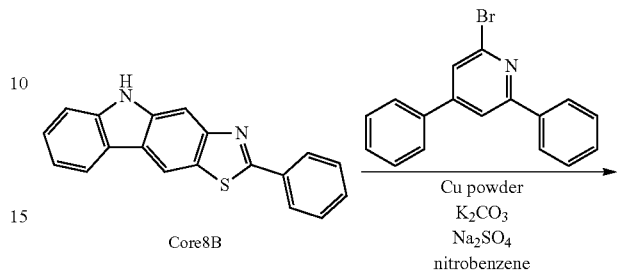

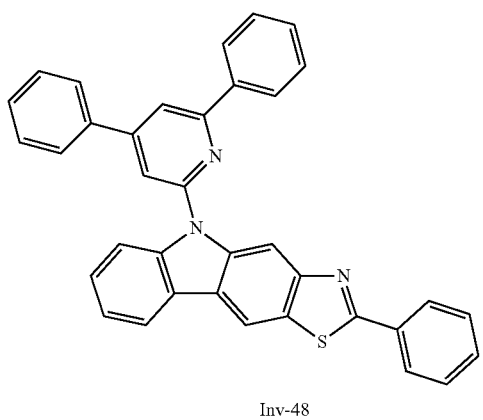

Inv-48

Compound Inv-48 (4.25 g, yield: 67%) was obtained by performing the same method as in Synthesis Example 20, except that 3.6 g of Compound Core8B synthesized in Preparation Example 8 was used instead of Compound Core5A used in Synthesis Example 20.

GC-Mass (theoretical value: 529.65 g/mol, measured value: 529 g/mol)

SYNTHESIS EXAMPLE 49

Synthesis of Compound Inv-49

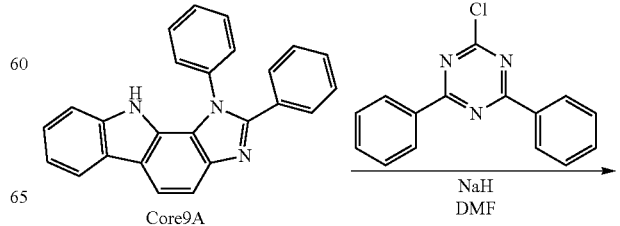

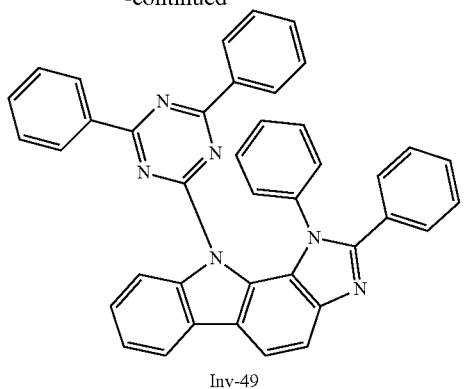

Inv-49

Compound Inv-49 (4.60 g, yield: 65%) was obtained by performing the same method as in Synthesis Example 9, except that 4.3 g of Compound Core9A synthesized in Preparation Example 9 was used instead of Compound Core3A used in Synthesis Example 9.

GC-Mass (theoretical value: 590.67 g/mol, measured value: 590 g/mol)

SYNTHESIS EXAMPLE 50

Synthesis of Compound Inv-50

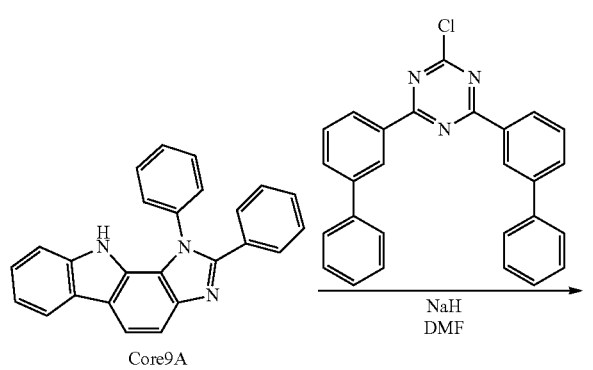

Inv-50

Compound Inv-50 (5.34 g, yield: 60%) was obtained by performing the same method as in Synthesis Example 18, except that 4.3 g of Compound Core9A synthesized in Preparation Example 9 was used instead of Compound Core5A used in Synthesis Example 18.

GC-Mass (theoretical value: 742.87 g/mol, measured value: 742 g/mol)

SYNTHESIS EXAMPLE 51

Synthesis of Compound Inv-51

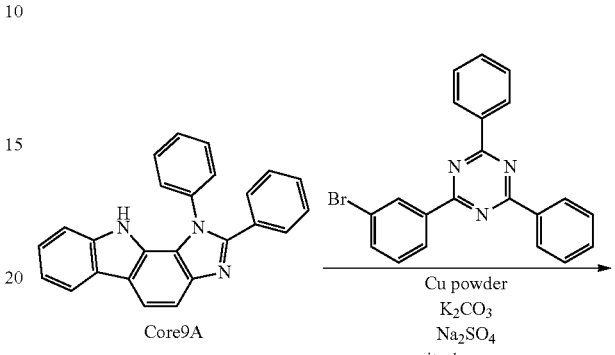

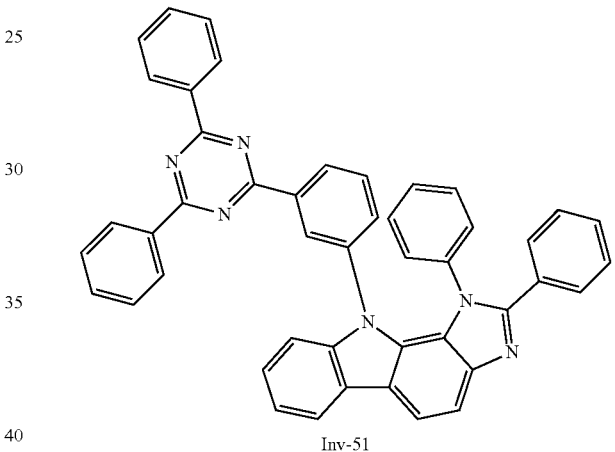

Inv-51

Compound Inv-51 (5.11 g, yield: 64%) was obtained by performing the same method as in Synthesis Example 10, except that 4.3 g of Compound Core9A synthesized in Preparation Example 9 was used instead of Compound Core3A used in Synthesis Example 10.

GC-Mass (theoretical value: 666.77 g/mol, measured value: 666 g/mol)

SYNTHESIS EXAMPLE 52

Synthesis of Compound Inv-52

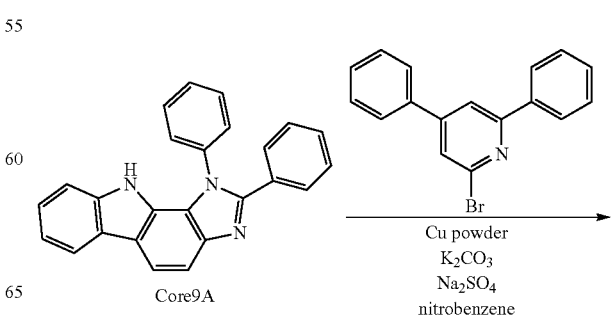

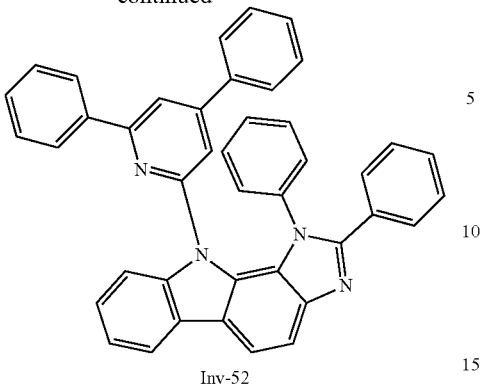

Inv-52

Compound Inv-52 (4.58 g, yield: 65%) was obtained by performing the same method as in Synthesis Example 20, except that 4.3 g of Compound Core9A synthesized in Preparation Example 9 was used instead of Compound Core5A used in Synthesis Example 20.

GC-Mass (theoretical value: 588.70 g/mol, measured value: 588 g/mol)

SYNTHESIS EXAMPLE 53

Synthesis of Compound Inv-53

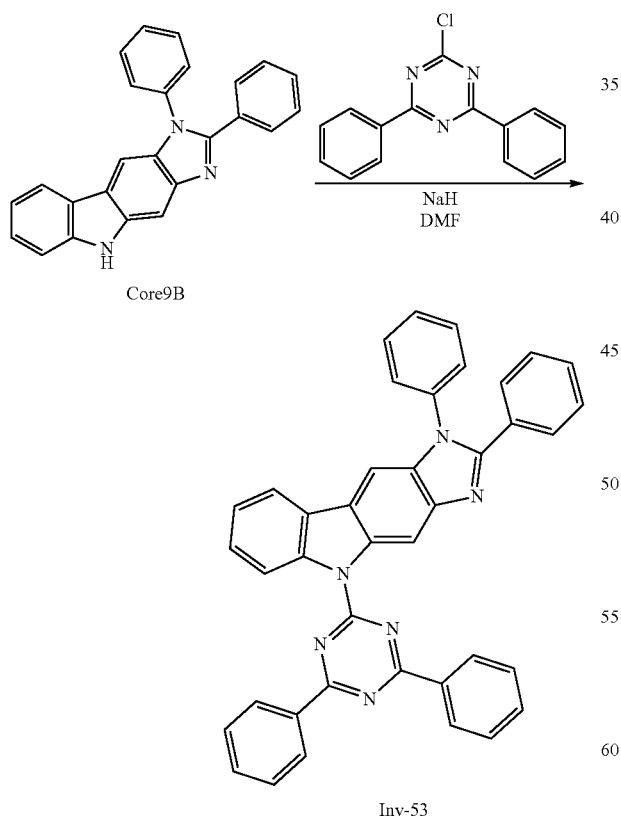

Inv-53

Compound Inv-53 (4.60 g, yield: 65%) was obtained by performing the same method as in Synthesis Example 9, except that 4.3 g of Compound Core9B synthesized in Preparation Example 9 was used instead of Compound Core3A used in Synthesis Example 9.

GC-Mass (theoretical value: 590.67 g/mol, measured value: 590 g/mol)

SYNTHESIS EXAMPLE 54

Synthesis of Compound Inv-54

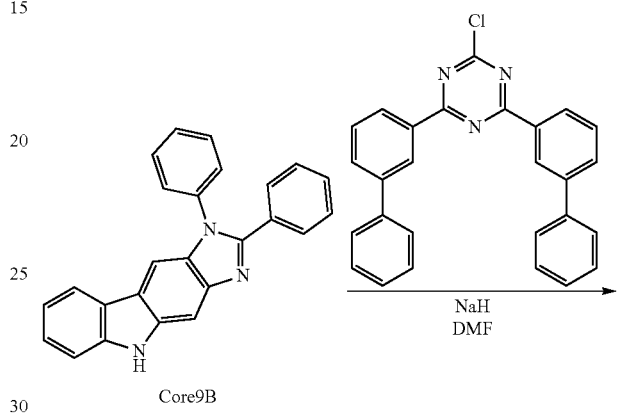

Core9B

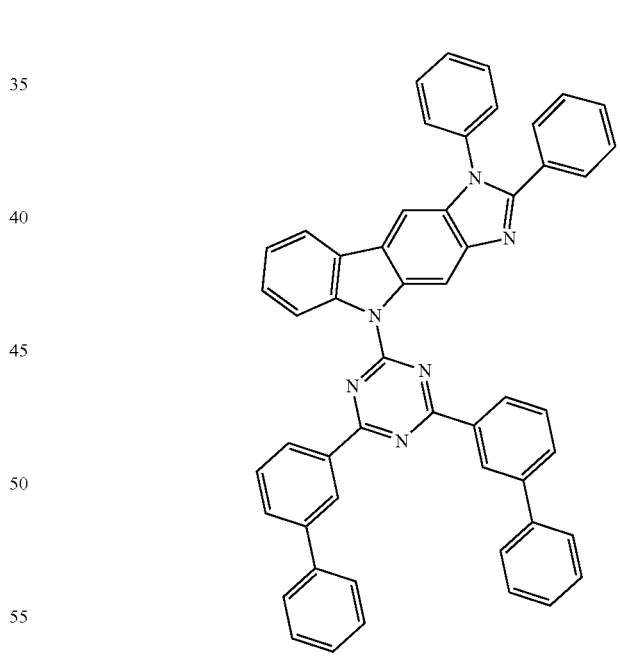

Inv-54

Compound Inv-54 (5.43 g, yield: 61%) was obtained by performing the same method as in Synthesis Example 18, except that 4.3 g of Compound Core9B synthesized in Preparation Example 9 was used instead of Compound Core5A used in Synthesis Example 18.

GC-Mass (theoretical value: 742.87 g/mol, measured value: 742 g/mol)

SYNTHESIS EXAMPLE 55

Synthesis of Compound Inv-55

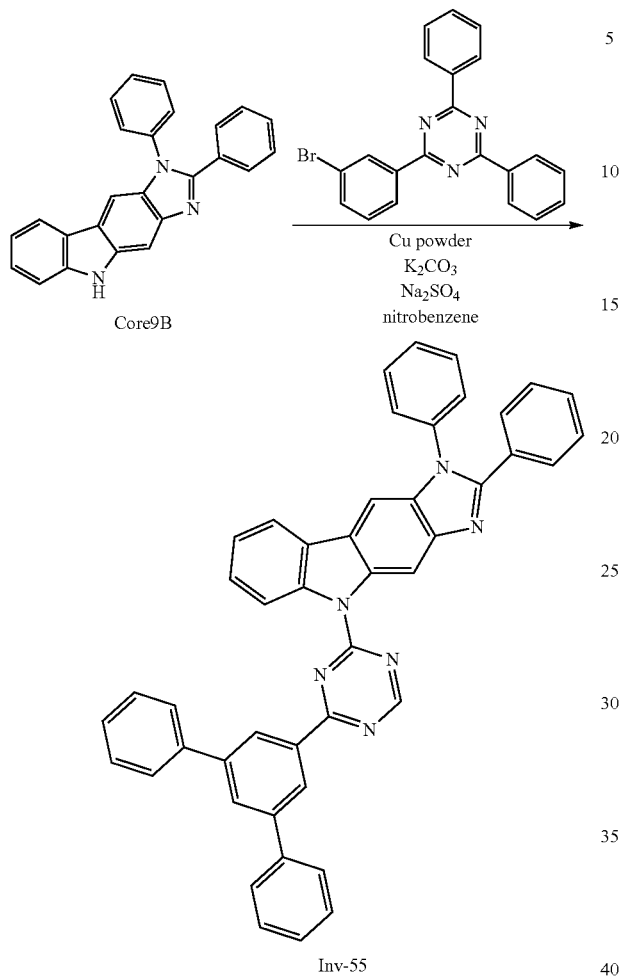

Inv-55

Compound Inv-55 (5.11 g, yield: 64%) was obtained by performing the same method as in Synthesis Example 10, except that 4.3 g of Compound Core9B synthesized in Preparation Example 9 was used instead of Compound Core3A used in Synthesis Example 10.

GC-Mass (theoretical value: 666.77 g/mol, measured value: 666 g/mol)

SYNTHESIS EXAMPLE 56

Synthesis of Compound Inv-56

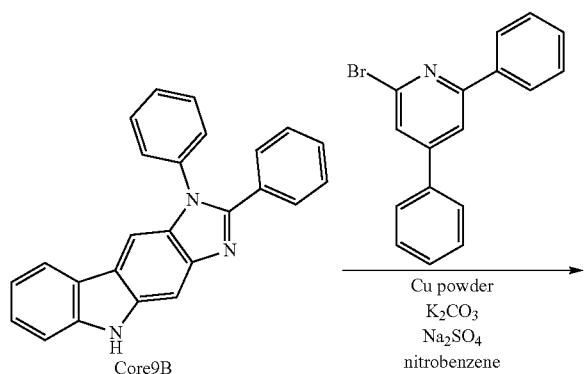

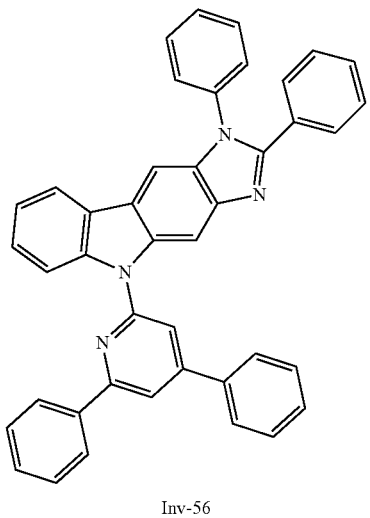

Inv-56

Compound Inv-56 (4.44 g, yield: 63%) was obtained by performing the same method as in Synthesis Example 20, except that 4.3 g of Compound Core9B synthesized in Preparation Example 9 was used instead of Compound Core5A used in Synthesis Example 20.

GC-Mass (theoretical value: 588.70 g/mol, measured value: 588 g/mol)

EXAMPLE 1

Manufacture of Organic EL Device

Compound Inv-1 synthesized in Synthesis Example 1 was subjected to highly-pure sublimation purification by a typically known method, and then an organic EL device was manufactured according to the following procedure.

A glass substrate on which a thin film of indium tin oxide (ITO) was coated to a thickness of 1500 Å was subjected to ultrasonic wave washing by distilled water. After with the washing by distilled water was finished, the glass substrate was ultrasonically washed with a solvent such as isopropyl alcohol, acetone and methanol, dried, and then transferred to a UV ozone cleaner (Power sonic 405, Hwashin Technology Co., Ltd.), and then the substrate was cleaned for 5 minutes by using UV rays, and transferred to a vacuum deposition system.

m-MTDATA (60 nm)/TCTA (80 nm)/Compound Inv-1+ 10% Ir(ppy)$_3$ (300 nm)/BCP (10 nm)/Alq$_3$ (30 nm)/LiF (1 nm)/Al (200 nm) were sequentially laminated on the ITO transparent electrode prepared as described above to form an organic EL device.

The structures of m-MTDATA, TCTA, Ir(ppy)$_3$, CBP, and BCP used are as follows.

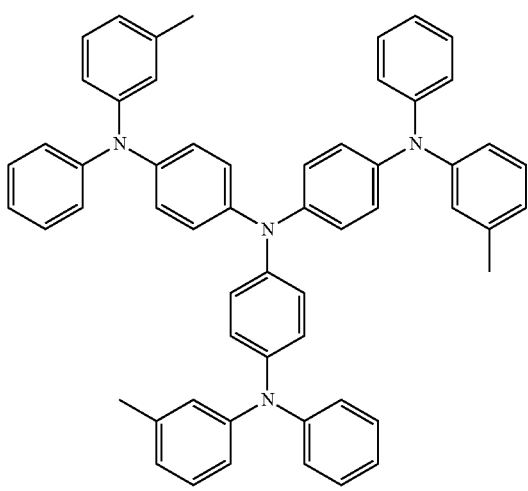

m-MTDATA

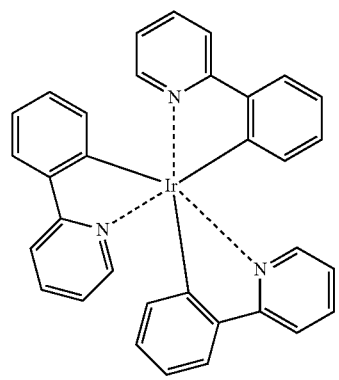

TCTA

Ir(ppy)₃

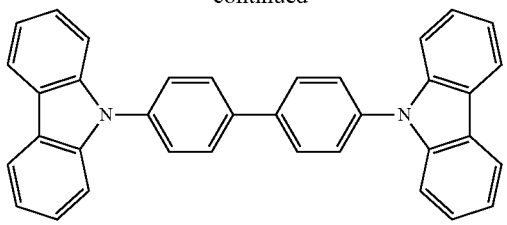

CBP

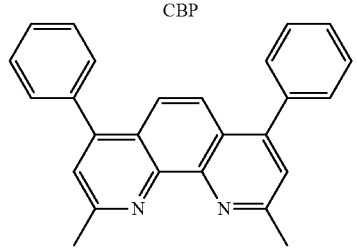

BCP

EXAMPLES 2 to 56

Manufacture of Organic EL Devices

Organic EL devices were manufactured in the same manner as in Example 1, except that Compounds Inv-2 to Inv-56 synthesized in Synthesis Examples 2 to 56, respectively, were used instead of Compound Inv-1 used as a host material when a light-emitting layer was formed in Example 1.

COMPARATIVE EXAMPLE 1

Manufacture of Organic EL Device

An organic EL device was manufactured in the same manner as in Example 1, except that CBP (4,4-dicarbazolybiphenyl) was used instead of Compound Inv-1 used as a light-emitting host material when a light-emitting layer was formed in Example 1. The structure of CBP used is the same as that described in Example 1.

EVALUATIVE EXAMPLE

For each of the organic EL devices manufactured in Examples 1 to 56 and Comparative Example 1, the driving voltage, current efficiency, and light-emitting peak were measured at a current density of 10 mA/cm², and the results are shown in the following Table 1.

TABLE 1

| Sample | Host | Driving voltage (V) | Current efficiency (cd/A) |
|---|---|---|---|
| Example 1 | Inv-1 | 6.60 | 42.4 |
| Example 2 | Inv-2 | 6.55 | 42.3 |
| Example 3 | Inv-3 | 6.60 | 42.5 |
| Example 4 | Inv-4 | 6.62 | 41.2 |
| Example 5 | Inv-5 | 6.68 | 41.6 |
| Example 6 | Inv-6 | 6.70 | 42.0 |
| Example 7 | Inv-7 | 6.59 | 41.5 |
| Example 8 | Inv-8 | 6.60 | 41.6 |
| Example 9 | Inv-9 | 6.70 | 41.3 |
| Example 10 | Inv-10 | 6.65 | 42.2 |

TABLE 1-continued

| Sample | Host | Driving voltage (V) | Current efficiency (cd/A) |
|---|---|---|---|
| Example 11 | Inv-11 | 6.71 | 41.1 |
| Example 12 | Inv-12 | 6.60 | 42.3 |
| Example 13 | Inv-13 | 6.65 | 43.2 |
| Example 14 | Inv-14 | 6.63 | 41.5 |
| Example 15 | Inv-15 | 6.60 | 43.2 |
| Example 16 | Inv-16 | 6.58 | 42.3 |
| Example 17 | Inv-17 | 6.50 | 41.5 |
| Example 18 | Inv-18 | 6.55 | 41.6 |
| Example 19 | Inv-19 | 6.60 | 41.3 |
| Example 20 | Inv-20 | 6.65 | 40.8 |
| Example 21 | Inv-21 | 6.66 | 40.2 |
| Example 22 | Inv-22 | 6.72 | 42.5 |
| Example 23 | Inv-23 | 6.60 | 41.2 |
| Example 24 | Inv-24 | 6.63 | 41.1 |
| Example 25 | Inv-25 | 6.65 | 40.9 |
| Example 26 | Inv-26 | 6.51 | 40.1 |
| Example 27 | Inv-27 | 6.59 | 41.5 |
| Example 28 | Inv-28 | 6.51 | 40.9 |
| Example 29 | Inv-29 | 6.60 | 41.1 |
| Example 30 | Inv-30 | 6.65 | 40.2 |
| Example 31 | Inv-31 | 6.70 | 42.0 |
| Example 32 | Inv-32 | 6.65 | 42.3 |
| Example 33 | Inv-33 | 6.62 | 41.2 |
| Example 34 | Inv-34 | 6.63 | 42.3 |
| Example 35 | Inv-35 | 6.61 | 41.7 |
| Example 36 | Inv-36 | 6.60 | 41.5 |
| Example 37 | Inv-37 | 6.55 | 40.6 |
| Example 38 | Inv-38 | 6.60 | 41.3 |
| Example 39 | Inv-39 | 6.65 | 41.8 |
| Example 40 | Inv-40 | 6.58 | 40.2 |
| Example 41 | Inv-41 | 6.70 | 41.5 |
| Example 42 | Inv-42 | 6.60 | 42.2 |
| Example 43 | Inv-43 | 6.63 | 41.1 |
| Example 44 | Inv-44 | 6.65 | 40.9 |
| Example 45 | Inv-45 | 6.53 | 40.1 |
| Example 46 | Inv-46 | 6.55 | 41.5 |
| Example 47 | Inv-47 | 6.50 | 40.9 |
| Example 48 | Inv-48 | 6.70 | 41.1 |
| Example 49 | Inv-49 | 6.60 | 41.2 |
| Example 50 | Inv-50 | 6.72 | 42.0 |
| Example 51 | Inv-51 | 6.70 | 41.3 |
| Example 52 | Inv-52 | 6.62 | 42.2 |
| Example 53 | Inv-53 | 6.63 | 41.3 |
| Example 54 | Inv-54 | 6.60 | 42.7 |
| Example 55 | Inv-55 | 6.65 | 41.5 |
| Example 56 | Inv-56 | 6.60 | 41.9 |
| Comparative Example 1 | CBP | 6.93 | 38.2 |

As shown in Table 1, it could be seen that the green organic EL devices (the organic EL devices manufactured in Examples 1 to 56) using the compounds (Compound Inv-1 to Compound Inv-56) according to the present invention as a material for a light-emitting layer (a host material) exhibit excellent performances in terms of current efficiency and driving voltage as compared to the known green organic EL device (the organic EL device in Comparative Example 1) using a CBP as a host material.

The invention claimed is:

1. A compound of the Formula selected from the group consisting of the following Formulae 9 to 12:

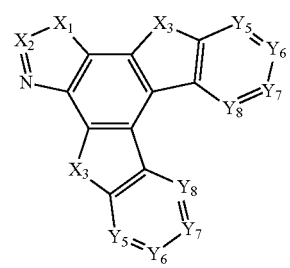

Formula 9

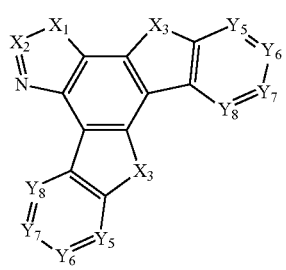

Formula 10

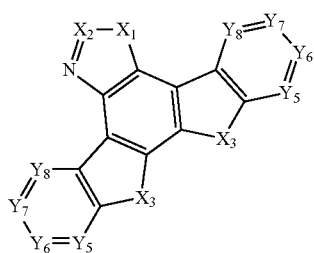

Formula 11

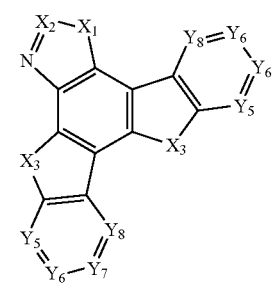

Formula 12 in Formulae 9 to 12, $X_1$ is selected from the group consisting of $NR_1$, O, S, Se, $SiR_2R_3$, and $CR_4R_5$;

$X_2$ is N or $CR_6$;

$Y_1$ to $Y_4$ are each independently N or $CR_7$, and in this case, a plurality of $CR_7$'s are the same as or different from each other;

$R_1$ to $R_7$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring, and in this case, the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_7$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group;

$X_3$ is selected from the group consisting of O, S, Se, $N(Ar_1)$, $C(Ar_2)(Ar_3)$, and $Si(Ar_4)(Ar_5)$, with the proviso that in Formula 10, $X_3$ is not S, and in this case, a plurality of $X_3$'s are the same as or different from each other;

$Ar_1$ to $Ar_5$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_3$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group;

$Y_5$ to $Y_8$ are each independently N or $CR_8$, and in this case, a plurality of $CR_8$'s is the same as or different from each other;

$R_8$ is selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_8$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

2. A compound of the formula selected from the group consisting of the following Formulae 3 to 8:

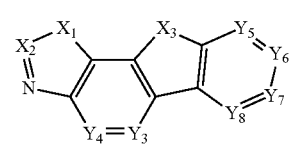

Formula 3

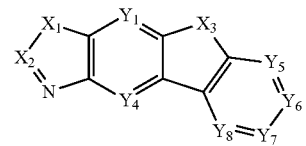

Formula 4

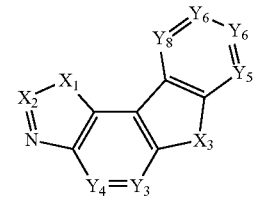

Formula 5

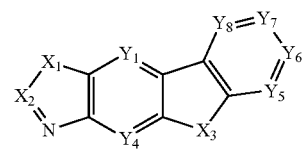

Formula 6

-continued

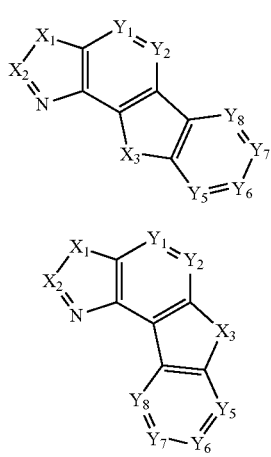

Formula 7

Formula 8 in Formula 3 to 8, $X_1$ is selected from the group consisting of $NR_1$, O, S, Se, $SiR_2R_3$, and $CR_4R_5$;

$X_2$ is N or $CR_6$;

$X_3$ is $N(Ar_1)$;

$Y_1$ to $Y_4$ are each independently N or $CR_7$, and in this case, a plurality of $CR_7$'s are the same as or different from each other, $R_1$ to $R_7$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring, with the proviso that in Formulae 4, $R_6$ is not hydrogen, cyano, and an unsubstituted $C_1$ to $C_{40}$ alkyl group, and that in Formulae 5, $R_6$ is not hydrogen and cyano;

$Ar_1$ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_3$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group;

$Y_5$ to $Y_8$ are each independently N or $CR_8$, and in this case, a plurality of $CR_8$'s are the same as or different from each other;

$R_8$ is selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group; and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_1$ to $R_8$ and $Ar_1$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

3. The compound as claimed in claim 1, wherein $X_3$ is $N(Ar_1)$, and $Ar_1$ is the same as that defined in claim 1.

4. The compound as claimed in claim 1, wherein $X_1$ is $NR_1$, $X_3$ is $N(Ar_1)$, and $R_1$ and $Ar_1$ are each the same as that defined in claim 1.

5. The compound as claimed in claim 1, wherein $R_1$ to $R_8$ and $Ar_1$ to $Ar_5$ are each independently selected from the group consisting of hydrogen, a substituted or unsubstituted $C_1$ to $C_{40}$ alkyl group, a substituted or unsubstituted $C_6$ to $C_{60}$ aryl group, a substituted or unsubstituted heteroaryl group having 5 to 60 nuclear atoms, and a substituted or unsubstituted $C_6$ to $C_{60}$ arylamine group; and the alkyl group, the aryl group, the heteroaryl group, and the arylamine group of $R_1$ to $R_8$ and $Ar_1$ to $Ar_5$ may be substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

6. The compound as claimed in claim 1, wherein $R_1$ to $R_8$ and $Ar_1$ to $Ar_5$ are each independently selected from the group consisting of hydrogen, and the following substituents A1 to A40:
A1
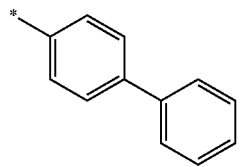
A2
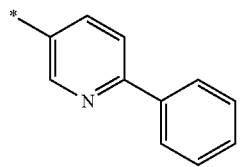
A3
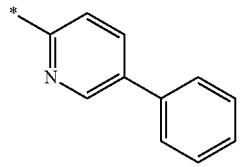
A4
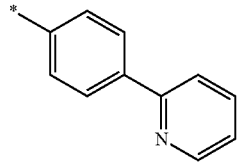
A5
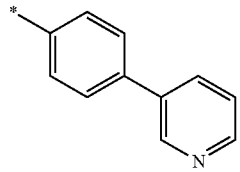
A6
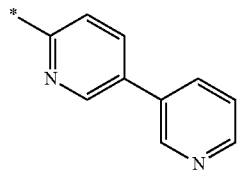
A7
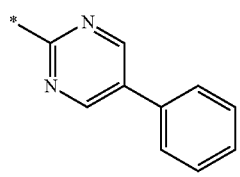
A8
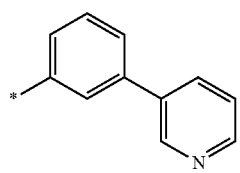
-continued
A9
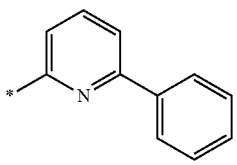
A10
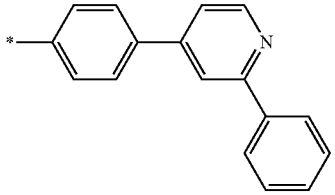
A11
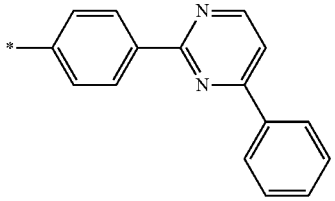
A12
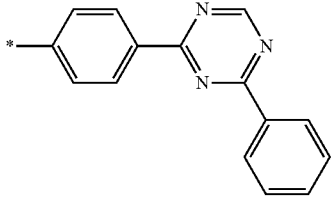
A13
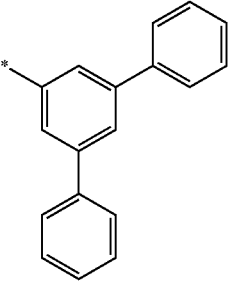
A14
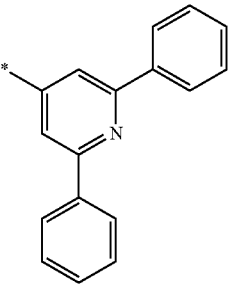

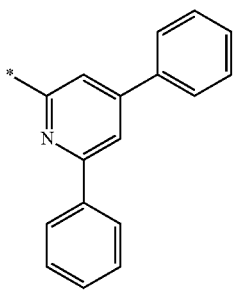
A15
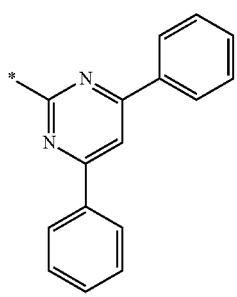
A16
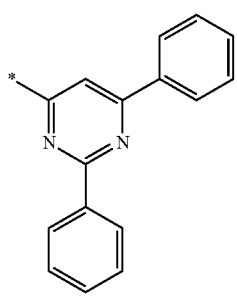
A17
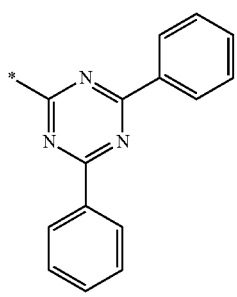
A18
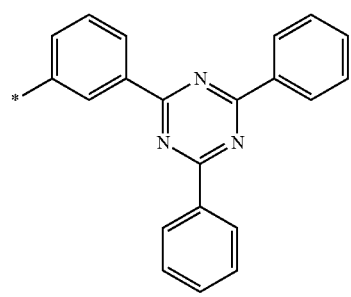
A19
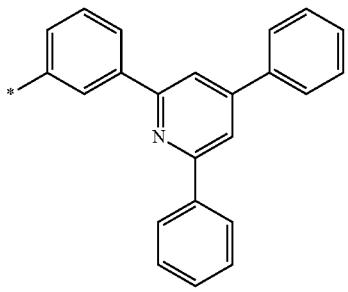
A20
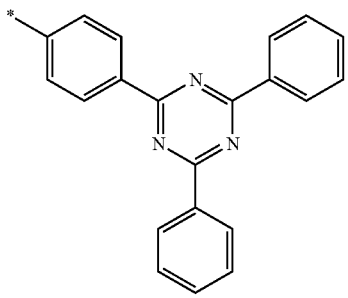
A21
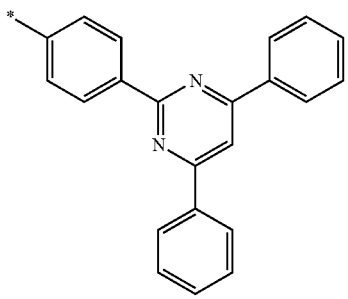
A22
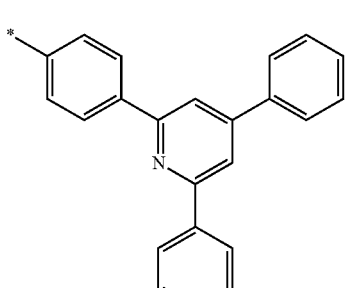
A23
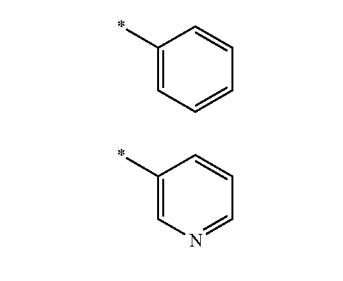
A24
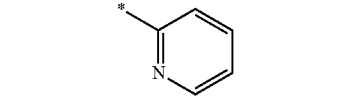
A25
A26

-continued
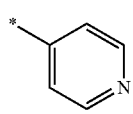
A27
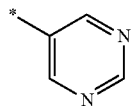
A28
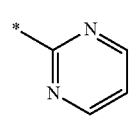
A29
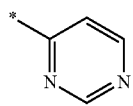
A30
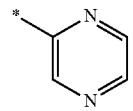
A31
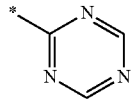
A32
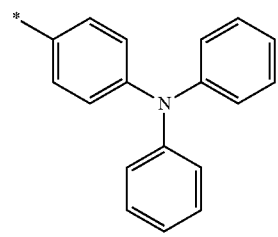
A33
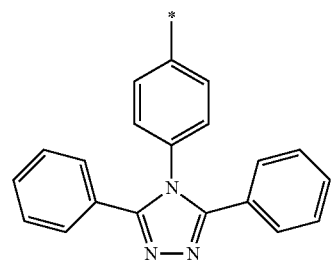
A34
-continued
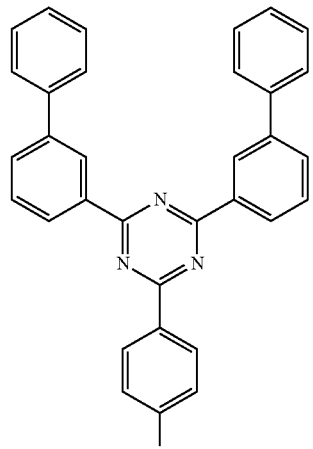
A35
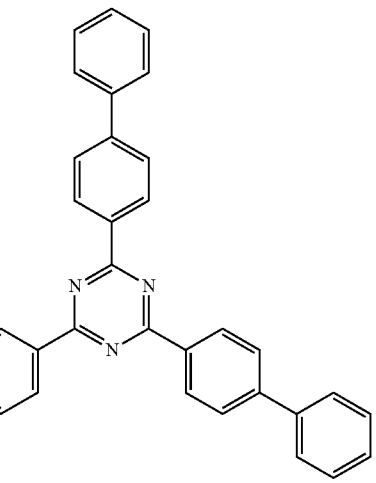
A36
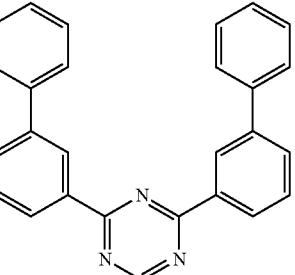
A37
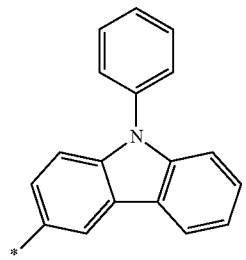
A38

-continued

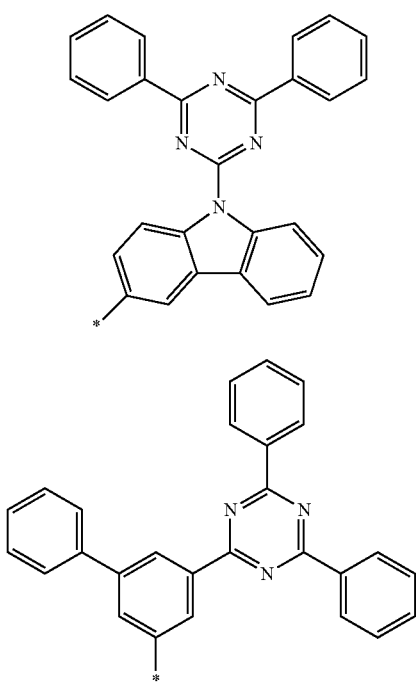

A39

A40

7. An organic electroluminescent device comprising:
an anode;
a cathode; and
one or more organic material layers interposed between the anode and the cathode,
wherein at least one of the organic material layers comprises a compound the formula selected from the group consisting of the following Formulae 9 to 12:

Formula 9

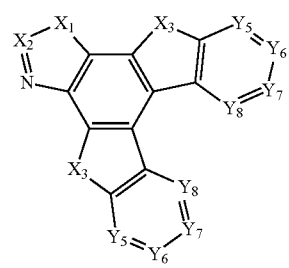

Formula 10

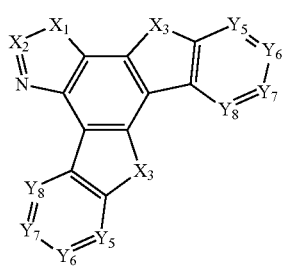

-continued

Formula 11

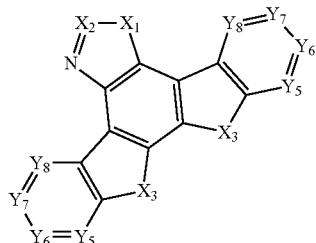

Formula 12

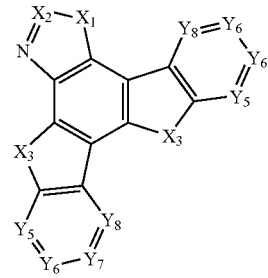

in Formulae 9 to 12,
$X_1$ is selected from the group consisting of $NR_1$, O, S, Se, $SiR_2R_3$, and $CR_4R_5$;
$X_2$ is N or $CR_6$;
$Y_1$ to $Y_4$ are each independently N or $CR_7$, and in this case, a plurality of $CR_7$'s are the same as or different from each other;
$R_1$ to $R_7$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring, and
in this case, the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_7$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group;

$X_3$ is selected from the group consisting of O, S, Se, $N(Ar_1)$, $C(Ar_2)(Ar_3)$, and $Si(Ar_4)(Ar_5)$, and in this case, a plurality of $X_3$'s are the same as or different from each other;

$Ar_1$ to $Ar_5$ are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_3$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $Ar_1$ to $Ar_5$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group;

$Y_5$ to $Y_8$ are each independently N or $CR_8$, and in this case, a plurality of $CR_8$'s are the same as or different from each other;

$R_8$ is selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring, and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_8$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

8. The organic electroluminescent device as claimed in claim 7, wherein the one or more organic material layers, which comprise the compound, are selected from the group consisting of a hole injection layer, a hole transporting layer, and a light-emitting layer.

9. The organic electroluminescent device as claimed in claim 8, wherein the compound is a host of the light-emitting layer.

10. An organic electroluminescent device comprising:

an anode;

a cathode; and one or more organic material layers interposed between the anode and the cathode, wherein at least one of the organic material layers comprises a compound of the formula selected from the group consisting of the following Formulae 3 to 8:

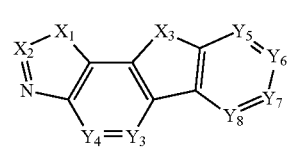

Formula 3

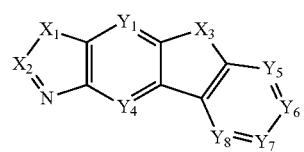

Formula 4

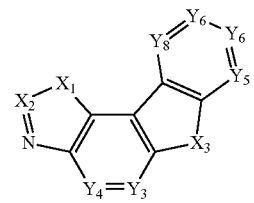

Formula 5

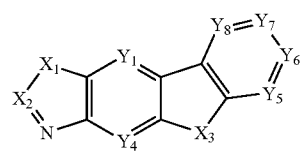

Formula 6

-continued

Formula 7

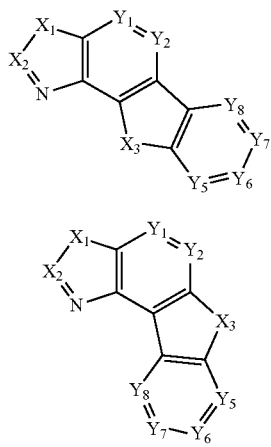

Formula 8 in Formulae 3 to 8, $X_1$ is selected from the group consisting of $NR_1$, O, S, Se, $SiR_2R_3$, and $CR_4R_5$;

$X_2$ is N or $CR_6$;

$X_3$ is $N(Ar_1)$;

$Y_1$ to $Y_4$ are each independently N or $CR_7$, and in this case, a plurality of $CR_7$'s are the same as or different from each other, $R_1$ to $R_7$ are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, or may be fused with an adjacent group to form a fused ring;

$Ar_1$ is selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_3$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group;

$Y_5$ to $Y_8$ are each independently N or $CR_8$, and in this case, a plurality of $CR_8$'s are the same as or different from each other;

$R_8$ is selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkylboron group, a substituted or unsubstituted $C_6$ to $C_{60}$ arylboron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group; and the alkyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group, and the arylamine group of $R_1$ to $R_8$ and $Ar_1$ may be each independently substituted with one or more substituents selected from the group consisting of deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_6$ to $C_{60}$ arylborane group, a $C_6$ to $C_{60}$ arylsilyl group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group, and a $C_6$ to $C_{60}$ arylamine group.

* * * * *